(12) United States Patent
Yaghi et al.

(10) Patent No.: US 9,102,609 B2
(45) Date of Patent: Aug. 11, 2015

(54) FUNCTIONALIZATION OF ORGANIC MOLECULES USING METAL-ORGANIC FRAMEWORKS (MOFS) AS CATALYSTS

(75) Inventors: Omar M. Yaghi, Berkeley, CA (US); Alexander U. Czaja, Freinsheim (DE); Anh Thi Phuong Phan, Beaverton, OR (US)

(73) Assignees: The Regents of the University of California, Oakland, CA (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/810,448

(22) PCT Filed: Jul. 20, 2011

(86) PCT No.: PCT/US2011/044625
§ 371 (c)(1),
(2), (4) Date: Sep. 16, 2013

(87) PCT Pub. No.: WO2012/012495
PCT Pub. Date: Jan. 26, 2012

(65) Prior Publication Data
US 2014/0012039 A1    Jan. 9, 2014

Related U.S. Application Data

(60) Provisional application No. 61/365,901, filed on Jul. 20, 2010.

(51) Int. Cl.
*C07C 51/16* (2006.01)
*B01J 31/02* (2006.01)
(Continued)

(52) U.S. Cl.
CPC .............. *C07C 51/16* (2013.01); *B01J 31/02* (2013.01); *C01B 39/00* (2013.01); *C07F 9/005* (2013.01)

(58) Field of Classification Search
CPC ......... C01B 39/00; C07C 51/16; C07F 9/005; B01J 31/02
USPC ........................................ 562/512.2
See application file for complete search history.

(56) References Cited

U.S. PATENT DOCUMENTS 2,684,967 A    7/1954    Berg
4,532,225 A    7/1985    Tsao et al.
(Continued)

FOREIGN PATENT DOCUMENTS

CN    1910191 A    2/2007
DE    102005023856 A1    11/2006
(Continued)

OTHER PUBLICATIONS

Di Nicola ("Supramolecular Assemblies of Trinuclear Triangular Copper (II) Secondary Building Units through Hydrogen Bonds. Generation of Different Metal-Organic Frameworks, Valuable Catalyst for Peroxidative Oxidation of Alkanes" Inorganic Chemistry, 2007, 46, 221-230).*

(Continued)

*Primary Examiner* — Jafar Parsa
*Assistant Examiner* — Amy C Bonaparte
(74) *Attorney, Agent, or Firm* — Joseph R. Baker, Jr.; Gavrilovich, Dodd & Lindsey LLP

(57) ABSTRACT

The disclosure provides for catalytic multivariate metal organic frameworks and methods of use thereof.

20 Claims, 3 Drawing Sheets

MIL-47

MOF-V150

(51) Int. Cl.
*C07F 9/00* (2006.01)
*C01B 39/00* (2006.01)

(56) References Cited

U.S. PATENT DOCUMENTS

| | | | |
|---|---|---|---|
| 5,064,804 A | 11/1991 | Soo et al. | |
| 5,160,500 A | 11/1992 | Chu et al. | |
| 5,208,335 A | 5/1993 | Ramprasad et al. | |
| 5,648,508 A | 7/1997 | Yaghi | |
| 5,733,505 A | 3/1998 | Goldstein et al. | |
| 6,479,447 B2 | 11/2002 | Bijl et al. | |
| 6,501,000 B1 | 12/2002 | Stibrany et al. | |
| 6,617,467 B1 | 9/2003 | Muller et al. | |
| 6,624,318 B1 | 9/2003 | Mueller et al. | |
| 6,686,428 B2 | 2/2004 | Zhang et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2* | 4/2007 | Mueller et al. | 568/679 |
| 7,279,517 B2* | 10/2007 | Mueller et al. | 524/199 |
| 7,309,380 B2 | 12/2007 | Mueller et al. | |
| 7,343,747 B2 | 3/2008 | Mueller et al. | |
| 7,411,081 B2* | 8/2008 | Mueller et al. | 556/118 |
| 7,524,444 B2 | 4/2009 | Hesse et al. | |
| 7,582,798 B2 | 9/2009 | Yaghi et al. | |
| 7,637,983 B1 | 12/2009 | Liu et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 | 10/2010 | Mueller et al. | |
| 8,480,955 B2 | 7/2013 | Yaghi et al. | |
| 8,709,134 B2 | 4/2014 | Yaghi et al. | |
| 8,735,161 B2 | 5/2014 | Yaghi et al. | |
| 8,742,152 B2 | 6/2014 | Yaghi et al. | |
| 2003/0004364 A1 | 1/2003 | Yaghi et al. | |
| 2003/0078311 A1 | 4/2003 | Mueller et al. | |
| 2003/0148165 A1 | 8/2003 | Mueller et al. | |
| 2003/0222023 A1 | 12/2003 | Mueller et al. | |
| 2004/0081611 A1 | 4/2004 | Mueller et al. | |
| 2004/0225134 A1 | 11/2004 | Yaghi et al. | |
| 2004/0249189 A1 | 12/2004 | Mueller et al. | |
| 2004/0265670 A1 | 12/2004 | Mueller et al. | |
| 2005/0004404 A1 | 1/2005 | Mueller et al. | |
| 2005/0014371 A1 | 1/2005 | Tsapatsis | |
| 2005/0124819 A1 | 6/2005 | Yaghi et al. | |
| 2005/0154222 A1 | 7/2005 | Muller | |
| 2005/0192175 A1 | 9/2005 | Yaghi et al. | |
| 2006/0057057 A1 | 3/2006 | Mueller et al. | |
| 2006/0135824 A1 | 6/2006 | Mueller et al. | |
| 2006/0154807 A1 | 7/2006 | Yaghi et al. | |
| 2006/0185388 A1 | 8/2006 | Mueller et al. | |
| 2006/0252641 A1 | 11/2006 | Yaghi et al. | |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |
| 2007/0202038 A1 | 8/2007 | Yaghi et al. | |
| 2007/0248575 A1 | 10/2007 | Connor et al. | |
| 2008/0017036 A1 | 1/2008 | Schultink et al. | |
| 2008/0184883 A1 | 8/2008 | Zhou et al. | |
| 2009/0155588 A1 | 6/2009 | Hesse et al. | |
| 2010/0132549 A1 | 6/2010 | Yaghi et al. | |
| 2010/0143693 A1 | 6/2010 | Yaghi et al. | |
| 2010/0186588 A1 | 7/2010 | Yaghi et al. | |
| 2010/0286022 A1 | 11/2010 | Yaghi et al. | |
| 2011/0137025 A1 | 6/2011 | Yaghi et al. | |
| 2012/0130113 A1* | 5/2012 | Yaghi et al. | 558/360 |

FOREIGN PATENT DOCUMENTS

| | | | |
|---|---|---|---|
| DE | 102005054523 A1 | 5/2007 | |
| EP | 1674555 A1 | 6/2006 | |
| JP | 2007534658 A | 11/2007 | |
| WO | 03035717 A1 | 5/2003 | |
| WO | 2004101575 A2 | 11/2004 | |
| WO | 2006072573 A2 | 7/2006 | |
| WO | 2006116340 A1 | 11/2006 | |
| WO | 2007007113 A2 | 1/2007 | |
| WO | 2007101241 A2 | 9/2007 | |
| WO | 2007111739 A2 | 10/2007 | |
| WO | 2008091976 A1 | 7/2008 | |
| WO | 2008138989 A1 | 11/2008 | |
| WO | 2008140788 A1 | 11/2008 | |
| WO | 2009020745 A9 | 2/2009 | |
| WO | 2009042802 A1 | 4/2009 | |
| WO | 2009056184 A1 | 5/2009 | |
| WO | 2009149381 A3 | 12/2009 | |
| WO | 2010056092 A9 | 5/2010 | |
| WO | 2010078337 A1 | 7/2010 | |
| WO | 2010080618 A1 | 7/2010 | |
| WO | 2010083418 A1 | 7/2010 | |
| WO | 2010088629 A1 | 8/2010 | |
| WO | 2010090683 A1 | 8/2010 | |
| WO | 2010148276 A3 | 12/2010 | |
| WO | 2010148296 A3 | 12/2010 | |
| WO | 2010148374 A3 | 12/2010 | |
| WO | 2011014503 A2 | 2/2011 | |
| WO | 2011038208 A2 | 3/2011 | |
| WO | 2011146155 A9 | 11/2011 | |
| WO | 2012012495 A3 | 1/2012 | |
| WO | 2012082213 A2 | 6/2012 | |
| WO | 2012100224 A3 | 7/2012 | |
| WO | 2012106451 A2 | 8/2012 | |

OTHER PUBLICATIONS

Costa ("Chemical Modification of a Bridging Ligand Inside a Metal-Organic Framework while Maintaining the 3D Structure" Eur. J. Inorg. Chem (2008) 10, 1551-1554).*

Kirillova ("Direct and Remarkably Efficient Conversion of Methane into Acetic Acid Catalyzed by Amavadine and Related Vanadium Complexes. A Synthetic and a Theoretical DFT Mechanistic Study" J. Am. Chem. Soc., 129 (2007), 10531-10545).*

Dhakshinamoorthy et al., "Metal Organic Frameworks as Efficient Heterogeneous Catalysts for the Oxidation of Benzylic Compounds with t-Butylhydroperoxide," In: J. Catal., 2009, pp. 1-4, vol. 267.

Dhakshinomoorthy et al., "Metal Organic Frameworks (MOFs) as Heterogeneous Catalysts for the Chemoselective Reduction of Carbon-Carbon Multiple Bonds with Hydrazine," In: Adv. Synth. Catal., 2009, pp. 2271-2276, vol. 351.

Young, Jung Doo, International Search Report & Written Opinion, Korean Intellectual Property Office, PCT/US2011/044625, Feb. 24, 2012.

Rinkel, Bert. Extended European Search Report for European Patent Application EP08713961, European Patent Office, Mail Date Jan. 2, 2012.

Rosi et al., "Infinite Secondary Building Units and Forbidden Catenation in Metal-Organic Frameworks," Angew. Chem. Int. Ed. 41:294-297 (2002).

Rosi et al., "Advances in the Chemistry of Metal-Organic Frameworks," CrystEngComm 4:401-404 (2002).

Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.

Rosi et al., "Rod-Packings and Metal-Organic Frameworks Constructed from Rod-Shaped Secondary Building Units," J. Am. Chem. Soc. 127:1504-1518 (2005).

Rouseau-Jager, Nadia, International Search Report and Written Opinion, PCT/US2011/024671, European Patent Office, Dec. 13, 2011.

Rowsell et al., "Hydrogen Sorption in Functionalized Metal-Organic Frameworks," J. Am. Chem. Soc.126: 5666-5667 (2004).

Rowsell et al., "Metal-Organic Frameworks: A New Class of Porous Materials," Microporous Mesoporous Mater. 73:3-14 (2004).

Rowsell et al., "Strategies for Hydrogen Storage in Metal-Organic Frameworks," Angew. Chem. Int. Ed. 44: 4670-4679 (2005).

Rowsell et al., "Gas Adsorption Sites in a Large-Pore Metal-Organic Framework," Science 309:1350-1354 (2005).

(56) References Cited

OTHER PUBLICATIONS

Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Seo et al., "A homochiral metal-organic porous material for enantioselective separation and catalysis," Nature 404:982-986 (2000).
Siberio-Perez, "Raman Spectroscopic Investigation of CH4 and N2 Adsorption in Metal-Organic Frameworks," Chem. Mater. 19:3681-3685 (2007).
Sigma-Aldrich, Basolite C300 (MOF-199), catalog No. 688614; http://www.sigmaaldrich.com/catalog/ProductDetail.do?D7=0 &N5=SEARCH_CONCAT_PNO%7CBRAND_KEY &N4=688614%7CALDRICH&N25=0&QS=ON&F=SPEC, obtained online in 2014.
Sines, Brian J. Non-Final Office Action for U.S. Appl. No. 13/142,564, United States Patent and Trademark Office, Mail Date Jul. 9, 2012.
Smaldone et al., "Metal-Organic Frameworks from Edible Nature Products," Angew. Chem. Int. Ed. 49:8630-8634 (2010).
Song et al., "Hydrothermal Synthesis and Structural Characterization of Three-dimensional Metal-organic Framework [Zn3(C2H2N3)2(C7H5O2)4]," Chem. Res. Chinese Universities 25(1):1-4 (2009).
Song et al., "A Multiunit Catalyst with Synergistic Stability and Reactivity: A PolyoxometalateMetal Organic Framework for Aerobic Decontamination," J. Am. Chem. Soc. 133(42):16839-16846 (Sep. 13, 2011).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Spitler et al., "Lewis Acid Catalyzed Formation of Two-Dimensional Phthalocyanine Covalent Organic Framewokrs." Nature Chem. 2:672-677 (Jun. 20, 2010).
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., "Systematic Functionalization of a Metal-Organic Framework via a Postsynthetic Modification Approach," J. Am. Chem. Soc. 130(26):8508-8517 (2008).
Tilford et al., "Facile Synthesis of a Highly Crystalline, Covalently Porous Boronate Network," 18(22):5296-5301 (Oct. 11, 2006).
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Tranchemontagne et al., "Hydrogen Storage in New Metal-Organic Frameworks," J. Phys. Chem. C 116 (24):13143-13151 (May 24, 2012).
Truang et al., Hydrocarbon adsorption in the Isostructural metal organic frameworks MIL-53(Cr) and MIL-47(V) Microporous and Mesoporous Materials, 140, Apr. 2011, 114-119.
Uribe-Romo et al., "A Crystalline Imine-Linked 3-D Porous Covalent Organic Framework," J. Am. Chem. Soc. 131:4570-4571 (2009).
37 Uribe-Romo et al., "Crystalline Covalent Organic Frameworks with Hydrazone Linkages," J. Am. Chem. Soc. 133: 11478-11481 (2011).
Vairaprakash et al., "Synthesis of Metal-Organic Complex Arrays," J. Am. Chem. Soc. 133:759-761 (2011).
Valente et al., "Metal-organic Frameworks with Designed Chiral Recognition Sites," Chem. Commun. 46: 4911-4913 (2010).
Vitillo et al., "Role of Exposed Metal Sites in Hydrogen Storage in MOFs," J. Am. Chem. Soc. 130(26):8386-8396 (2008).
Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)," J. Am. Chem. Soc.124 (18):4942-4943 (2002).
Vodak et al., " Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wan et al, "A Belt-Shaped, Blue Luminescent, and Semiconducting Covalent Organic Framework." Angew. Chem. Int. Ed. 47:8826-8830 (2008).
Wan et al., "Covalent Organic Frameworks with High Charge Carrier Mobility," Chem. Mater. 23:4094-4097 (Aug. 22, 2011).
Wang et al., "Postsynthetic Covalent Modification of a Neutral Metal-Organic Framework," J. Am. Chem. Soc. 129 (41):12368-12369 (2007).
Wang et al., "Tandem Modification of Metal-Organic Frameworks by a Postsynthetic Approach," Angew. Chem. Int. 47:4699-4702 (2008).
Wang et al., "Colossal Cages in Zeolitic Imidazolate Frameworks as Selective Carbon Dioxide Reservoirs," Nature 453:207-211 (2008).
Wong-Foy, Ag et al., "Exceptional H2 saturation uptake in microporous metal-organic frameworks" J. Am. Chem. Soc., 2006, 128, pp. 3494-3495.
Wu et al., "Structural Study of New Hydrocarbon Nano-Crystals by Energy-Filtered Electron Diffraction," Ultramicroscopy 98:145-150 (2004).
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extend Structure of Cu(4,4'-Bipyridine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks,"Mater. Res. Soc. Symp. Proc., 1995, 371, 15.
Yaghi et al., "Hydrothermal Synthesis of a Metal-Organic Framework Containing Large Rectangular Channels," J. Chem. Soc., 1995, 117, 10401-10402.

(56) References Cited

OTHER PUBLICATIONS

Yaghi et al., "T-Shaped Molecular Building Units in the Porous Structure of Ag(4,4'-bpy) NO3," J. Am. Chem. Soc., 1996, 118, 295-296.

Yaghi et al., "Construction of Porous Solids from Hydrogen-Bonded Metal Complexes of 1,3,5-Benzenetricarboxylic Acid," J. Am. Chem. Soc., 1996, 118, 9096-9101.

Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).

Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.

Yaghi et al., "Crystal Growth of Extended Solids by Nonaqueous Gel Diffusion," Chem. Mater., 1997, 9, 1074-1076.

Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.

Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).

Yaghi et al., "Synthesis and Structure of a Metal-Organic Solid Having the Cadmium (II) Sulfate Net," Mater. Res. Soc. Symp. Proc. 453:127, (1997).

Yaghi et al., "Designing Microporosity in Coordination Solids," Modular Chemistry, J. Michl, Ed., Kluwer: Boston, p. 663 (1997).

Yaghi et al., "Synthetic Strategies, Structure Patterns, and Emerging Properties in the Chemistry of Modular Porous Solids," Acc. Chem. Res. 31:474-484 (1998).

Yaghi et al., "Transformation of Germanium Dioxide to 4-Connected Porous Germanate Net," J. Am. Chem. Soc., 20:10569-10570 (1998).

Yaghi et al., "Design of Solids from Molecular Building Blocks: Golden Opportunities for Solid State Chemistry," J. Solid State Chem. 152, 1-2 (2000).

Yaghi et al., "Reticular Synthesis and the Design of New Materials," Nature 423:705-714 (2003).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi et al., "Metal-Organic Frameworks: A Tale of Two Entanglements," Nature materials 6:92-93 (2007).

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Reticular Chemistry and Metal-Organic Frameworks for Clean Energy," MRS Bulletin 34:682-690 (2009).

Yang et al., "Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties," Crystal Growth Design 7(10):2009-2015 (2007).

Yang et al. "Two Novel Triazole-Based Metal-Organic Frameworks Consolidated by a Flexible Dicarboxylate Co-ligand: Hydrothermal Synthesis, Crystal Structure, and Luminescence Properties," Australian Journal of Chemistry 61(10):813-820 (2008).

Young, Lee W., International Search Report and Written Opinion, Date of Mailing of Report: May 7, 2008, International Application No: PCT/US08/51859.

Young, Lee W., "International Search Report and Written Opinion," PCT/US08/06008, United States Patent & Trademark Office, Aug. 20, 2008.

Young, Lee W., International Search Report and Written Opinion, Date of Mailing: Dec. 2, 2008, International Application Number: PCT/US08/77741.

Young, Lee W., International Search Report and Written Opinion, Date of Mailing: Jan. 12, 2009, International Application Number: PCT/US08/70149.

Young, Jung Doo. International Search Report for PCT/US2010/050170. Date of Mailing: Jun. 8, 2011.

Jung Doo, International Search Report and Written Opinion for PCT/US2011/053423. Date of mailing of ISR Jul. 23, 2012.

Young, Jung Doo, International Search Report and Written Opinion for PCT/US2012/022114. Date of mailing of ISR Aug. 22, 2012.

Zhang et al., "Crystal engineering of binary metal imidazolate and triazolate frameworks," Chem. Comm. 1689-1699 (2006).

Zhang, J. et al., "Exceptional Framework Flexibility and Sorption Behavior of a Multifunctional Porous Cuprous Triazolate Framework," J. Am. Chem. Soc. 130:6010-6017 (2008).

Zhang et al., "Docking in Metal-Organic Frameworks," Science 325:855-859 (2009).

Zhang et al., "Syntheses, Structures, and Porous/Luminescent Properties of Silver 3-Alkyl-1,2,4-Triazolate Frameworks with Rare 3-Connected Topologies," Crystal Growth and Design 11:796-802 (2011).

Zhao et al., "Rigid-Strut-Containing Crown Ethers and [2]Catenanes for Incorporation into Metal-Organic Frameworks," Chem. Eur. J. 15:13356-13380 (2009).

Zhao, Wei. The First Office Action for Chinese Application No. 200880003157.2. The State Intellectual Property Office of the People's Republic of China. Issue Date: Aug. 5, 2011.

Zhou, X et al., "Hydrothermal Syntheses and Structures of Three Novel Coordination Polymers Assembled from 1,2,3-Triazolate Ligands," CrystEngComm. 11:1964-1970 (2009).

Zhou et al., "Introduction to Metal-Organic Frameworks," Chemical Reviews 112:673-674 (Jan. 26, 2012).

Zhu, A. et al., "Isomeric Zinc(II) Triazolate Frameworks with 3-Connected Networks: Syntheses, Structures, and Sorption Properties," Inorg. Chem. 48:3882-3889 (2009).

First Office Action issued in Chinese Patent Application No. 201180045210.8, Sep. 28, 2014.

Demessence, A et al., "Strong CO2 Bnding in a Water-Stable, Triazolate-Bridged Metal-Organic Framework Functionalized with Ethylenediamine," J. Am. Chem. Soc. 131:8784-8786 (2009).

Demir A.S. et al., "Role of Copper Species in the Oxidation Dimerization of Arylbornonic Acids: Synthesis of Symmetrical Biaryls," J. Of Organic Chemistry, Dec. 26, 2003, vol. 68, No. 26, pp. 10130-10134.

Deng et al., "Multiple Functional Groups of Varying Ratios in Metal-Organic Frameworks," Science 327:846-850 (2010).

Deng et al., "Robust dynamics" Nature Chem. 2:439-443 (2010).

Deng et al., "Large-Pore Apertures in a Series of Metal-Organic Frameworks," Science 336:1018-1023 (May 25, 2012).

Dhakshinamoorthy et al., "Metal-organic frameworks as heterogeneous catalysts for oxidation reactions", Catal. Sci. Technol., Apr. 28, 2011, 1, 856-867.

Doonan et al., "Isoreticular Metalation of Metal-Organic Frameworks," J. Am. Chem. Soc. 131:9492-9493 (2009).

Doonan, C., "Hydrogen Storage in Metal-Organic Frameworks," Annual Merit Review Proceedings of DOE Hydrogen Program, May 22, 2009.

Doonan et al., "Exceptional ammonia uptake by a covalent organic framework," Nature Chem. 2:235-238 (2010).

Dugan et al., "Covalent modification of a metal-organic framework with isocyanates: probing substrate scope and reactivity," 29:3366-3368 (2008).

Duren et al., "Design of New Materials for Methane Storage," Langmuir 20:2683-2689 (2004).

Eberhard, Michael, Extended European Search Report, EP11810321, Jan. 14, 2014.

Eddaoudi et al., "Design and Synthesis of Metal-Organic Frameworks with Permanent Porosity," In Topics in Catalysis, G. A. Somorjai and J. M. Thomas, Eds., 9:105 (1999).

Eddaoudi et al., "Highly Porous and Stable Metal-Organic Framework: Structure Design and Sorption Properties," J. Am. Chem. Soc. 121:1391-1397 (2000).

(56) References Cited

OTHER PUBLICATIONS

Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o—Br—C6H3(CO2)2]2(H2O)2•(DMF)8(H2O)2: A Framework Deliberately Designed to have the NbO Structure Type," J. Am. Chem. Soc.124:376-377 (2002).
Fei et al., "A Nearly Planar Water Sheet Sndwiched between Strontium-Imidazolium Carboxylate Coordination Polymers," Inorg. Chem., 2005, pp. 5200-5202, vol. 44.
Ferragut et al., "Positronium Formation in Porous Materials for Antihydrogen Production,"J. Phys. Conf. Ser. 225:1-8 (2010).
Finger, Gabriela, International Search Report and Written Opinion, PCT/US2010/043373, European Patent Office, Date of Mailing: Oct. 6, 2010.
Fracaroli et al., "Isomers of Metal-Organic Complex Arrays," Inorg. Chem. 51: 6437-6439 (Jun. 5, 2012).
Furukawa et al., "Crystal Structure, Dissolution, and Deposition of a 5 nm Functionalized Metal-Organic Great Rhombicuboctahedron," J. Am. Chem. Soc. 128:8398-8399 (2006).
Furukawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Furukawa et al., "Isoreticular Expansion of MetalOrganic Frameworks with Triangular and Square Building Units and the Lowest Calculated Density for Porous Crystals," Inorg. Chem. 50:9147-9152 (2011).
Gadzikwa, T. et al., "Selective Bifunctional Modification of a Non-catenated Metal-Organic Framework Material via Click Chemistry," J. Am. Chem. Soc. 131:13613-13615 (2009).
Galli et al., "Adsorption of Harmful Organic Vapors by Flexible Hydrophobic Bis-pyrazolate Based MOFs," Chem. Mater. 22(5):1664-1672 (2010).
Gandara et al., "Porous, Conductive Metal-Triazolates and Their Structural Elucidation by the Charge-Flipping Method," Chem. Eur. J. 18:10595-10601 (2012).
Gassensmith et al., "Strong and Reversible Binding of Carbon Dioxide in a Green Metal-Organic Framework," J. Am. Chem. Soc. 133:15312-15315 (Aug. 30, 2011).
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Gonzales-Arellano C. et al., "Homogeneous and heterogenized Au(III) Schiff base-complexes as selective and general catalysts for self-coupling of aryl boronic acids," Chemical Communications, Apr. 21, 2005, No. 15, pp. 1990-1992.
Goto, Y et al., "Clickable Metal-Organic Framework," J. Am. Chem. Soc. 130:14354-14355 (2008).
Grzesiak et al., "Polymer-Induced Heteronucleation for the Discovery of New Extended Solids," Angew. Chem. Int. Ed. 45:2553-2556 (2006).
Halper et al., "Topological Control in Heterometallic Metal-Organic Frameworks by Anion templating and Metalloligand Design," J. Am. Chem. Soc., 2006, pp. 15255-15268, vol. 128.
Han, Ss et al., "Improved designs of metal-organic frameworks for hydrogen storage" Angew. Chem. Int. Ed. 2007, 46, pp. 6289-6292.
Han et al., "Covalent Organic Frameworks as Exceptional Hydrogen Storage Materials," J. Am. Chem. Soc. 130: 11580-11581(2008).
Hassan et al., "Aryl-Aryl Bond Formation One Century After the Discovery of the Ullmann Reaction", Chem. Rev., Mar. 8, 2002, 102, 1359-1460.
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Hmadeh et al., "New Porous Crystals of Extended Metal-Catecholates," J. Chem. Mater. 24:3511-3513 (Aug. 28, 2012).
Holler et al., "The first dinitrile frameworks of the rare earth elements: [LnCl3(1,4-Ph(CN)2] and [Ln2Cl6(1,4Ph(CN)2], Ln=Sm, Gd, Tb, Y; Access to novel metal-organic frameworks by solvent free synthesis in molten 1,4-benodinitrile," Inorganic Chemistry 47(21): 10141-9 (2008).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: Jun. 4, 2010.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Hunt et al., "Reticular Synthesis of Covalent Organic Borosilicate Frameworks," J. Am. Chem. Soc. 130: 11872-11873 (2008).
Ingleson et al., "Framework fractionalization triggers metal complex binding," Chem. Comm. 23:2680-2682 (2008).
Isaeva et al., "Metal-organic frameworks-new materials for hydrogen storage," Russian Journal of General Chemistry 77(4):721-739 (2007).
Jeong et al., "Asymmetric Catalytic Reactions by NbO-Type Chiral Metal-Organic Frameworks," Chem. Sci. 2:877-882 (2011).
Jones, Christopher, Non-Final Office Action for U.S. Appl. No. 12/598,855, United States Patent and Trademark Office, Mail Date Jun. 14, 2012.
Jones, Christopher, Non-Final Office Action for U.S. Appl. No. 12/598,855, United States Patent and Trademark Office, Mail Date Oct. 12, 2012.
Kaderi et al., "Designed Synthesis of 3D Covalent Organic Frameworks," Science 316:268-272 (2007).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion, Date of Mailing: Feb. 24, 2010, International Application Number: PCT/US09/46463.
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Kim et al., "Isoreticular MOFs based on a rhombic dodecahedral MOP as a tertiary building unit", CrystEngComm, Mar. 3, 2014, Paper, DOI: 10.1039/o4ce00017.

(56) References Cited

OTHER PUBLICATIONS

Kirai, N., et al., "Homocoupling of arylboronic acids catalysed by 1,10-phenanthroline-ligated copper complexes in air," European J. of Organic Chemistry, Mar. 16, 2009, pp. 1864-1867.
Klaes, Daphne. International Search Report and Written Opinion for PCT/US2010/021201. Date of Mailing: Apr. 27, 2010.
Koh et al., "A Crystalline Mesoporous Coordination Copolymer with High Microporosity," Angew Chem Int'l, 2008, vol. 47, pp. 677-680.
Koza, D.J. et al., "An Efficient High Yielding Approach For The Homocoupling of Aryl Boronic Acids," Synthesis, Nov. 1, 2002, No. 15, pp. 2183-2186.
Kyoungmoo et al., "A Crystalline Mesoporous Coordination Copolymer with High Microporosity," Angew. Chem. Int. Ed. 47(4):677-680 (2008).
Lakmini et al., "Pd-Catalyzed Homocoupling Reaction of Arylboronic Acid: Insights from Density Functional Theory", J. Phys. Chem. A, Jul. 2, 2008, 112, 12896-12903.
Lawrence, Frank M., Non-Final Office Action for U.S. Appl. No. 12/699,616, United States Patent and Trademark Office, Date of Mailing: Apr. 10, 2012.
Lawrence, Frank M., Non-Final Office Action for U.S. Appl. No. 12/699,616, United States Patent and Trademark Office, Date of Mailing: Aug. 3, 2012.
Lee et al., "Metal-organic framework materials as catalysts", Chem. Soc. Rev., Mar. 17, 2009, 38, 1450-1459.
Lee et al., "Synthesis and Gas Sorption Properties of a Metal-Azolium Framework (MAF) Material," Inorganic Chemistry, Nov. 2, 2009, pp. 9971-9973, vol. 48, No. 21.
Lee, Ji Min. International Search Report for PCT/US2010/039284, Korean Intellectual Property Office, Date of Mailing: Feb. 22, 2011.
Leus et al., "The remarkable catalytic activity of the saturated metal organic framework V-MIL-47 in the cyclohexene oxidation", Chem. Comm., Jun. 18, 2010, 46, 5085-5087.
Li et al., "Coordinatively Unsaturated Metal Centers in the Extended Porous Framewokr of Zn3(BDC)3—6CH3OH (BDC= 1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of Ge7O4.5F2—[(CH3)2NH2]3(H2O) 0.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Famework," J. Am. Chem. Soc. 121:6096-6097 (1999).
Li et al., "Design and Synthesis of an Exceptionally Stable and Highly Porous Metal-Organic Framework," 402:276-279 (1999); Featured in (1) Chemical and Engineering News (Nov. 22, 19999) and (2) Science News (Nov. 20, 1999).
Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).
Li et al., "20 A [Cd4ln16S35]14- Supertetrahedral T4 Clusters as Building Units in Decorated Cristobalite Frameworks," J. Am. Chem Soc. 123:4867-4868 (2001).
Li et al., "[Cd16In64S134]44-: 31-Å Tetrahedron with a Large Cavity," Angew. Chem. Int. Ed., 42:1819-1821 (2003).
Li, Y et al., "Hydrogen Storage in Metal-Organic and Covalent-Organic Frameworks by Spillover," AIChe Journal 54 (1):269-279 (2008).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).

Li et al., "Synthesis and Structural Characterization of a New 3D Lead Coordination Polymer with a Tetrazole-1-acetate Ligand," Chinese J. Struct. Chem. 30(7):1049-1053 (2011).
Linder, Nora. International Preliminary Report on Patentability for PCT/US2010/022777. Date of Mailing: Aug. 11, 2011.
Lindner, Nora, International Preliminary Report on Patentability and Written Opinion, The International Bureau of WIPO, PCT/US2011/044625, Jan. 31, 2013.
Ling et al., "A zinc(II) metal-organic framework based on triazole and dicarboxylate ligands for selective adsorption of hexane isomers," Chem. Comm. 47:7197-7199 (2011).
Liu, Lei, First Office Action, Chinese Patent Application No. 201180009370.6,The State Intellectual Property Office of the People's Republic of China, Issue Date: Mar. 3, 2014.
Llabres et al., "MOFs as catalysts: Activity, reusability and shape-selectivity of a Pd-containing MOF", Journal of Catalysis, 250, Jul. 27, 2007, 294-298.
Loeb, Sj, "Rotaxanes as ligands: from molecules to materials" Chemical Society Reviews, 2007, 36, pp. 226-235.
Long et al., "The Pervasive Chemistry of Metal-Organic Frameworks," Chem. Soc. Rev. 38:1213-1214 (2009).
Adamo et al., "Mechanism of the Palladium-Catalyzed Homocoupling of Arylboronic Acids: Key Involvement of a Palladium Peroxo Complex", J. Am. Chem. Soc., May 31, 2006, 128, 6829-6836.
Adkins, Chinessa T. Nonfinal Office Action for U.S. Appl. No. 12/524,205. Mail Date Apr. 17, 2012.
Adkins, Chinessa T. Final Office Action for U.S. Appl. No. 12/524,205. Mail Date Sep. 27, 2012.
Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
Baharlou, Simin. International Preliminary Report on Patentability for PCT/US2009/046463. Date of Mailing: Dec. 16, 2010.
Baharlou, Simin. International Preliminary Report on Patentability for PCT/US2010/043373. Date of Mailing: Feb. 9, 2012.
Baharlou, Simin, International Preliminary Report on Patentability for PCT/US2011/024671, The International Bureau of WIPO, Date of Mailing: Aug. 23, 2012.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barman et al., "Incorporation of active metal sites in MOFs via in situ generated ligand deficient metal-linker complexes" Chem. Commun. 47:11882-11884 (Oct. 11, 2011).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions Within Metal-Organic Frameworks," Inorg. Chem. 49:6387-6389 (2010).
Burrows et al., "Post-Synthetic Modification of Tagged MOFs," Angew. Chem. Int. Ed. 47:8482-8486 (2008).
Carlucci et al., "Nanoporous three-dimensional networks topologically related to cooperite from the self-assembly of copper(I)centres and teh 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.

(56) References Cited

OTHER PUBLICATIONS

Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 2004, (3) New Scientist, Feb. 2004.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Chen et al., "Noncovalently Netted, Photoconductive Sheets with Extremely High Carrier Mobility and Conduction Anisotropy from Triphenylene-Fused Metal Trigon Conjugates", In. J. Am. Chem. Soc., 131:7287-7297 (2009).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Choi et al., "Reversible Interpenetration in a Metal-Organic Framework Triggered by Ligand Removal and Addition," Angew. Chem. Int. Ed. 51:8791-8795 (2012).
Chun et al., "Concomitant Formation of N-Heterocyclic Carbene-Copper Comlexies within a Supramolecular Network in the Self-Assembly of Immidzolium Dicarboxylate with Metal Ions," Inorganic Chemistry, Jul. 20, 2009, pp. 6353-6355, vol. 48, No. 14.
Chun et al., "Cu2O: A versatile Reagent for Base-Free Direct Synthesis of NHC-Copper Complexes and Decoration of 3D-MOF with Coordinatively Unsaturated NHC-Copper Species," Organometallics, Mar. 16, 2010, pp. 1518-1521, vol. 29, No. 7.
Coskun et al., "Metal-Organic Frameworks Incorporating Copper-Complexed Rotaxanes," Angew. Chem. Int. Ed., 51:2160-2163 (2012).
Cordero Garcia, Marcela M. Nonfinal Office Action for U.S. Appl. No. 12/680,141, United States Patent and Trademark Office,Date of Mailing: Nov. 2, 2012.
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Cui et al., "In Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).
Czaja et al., "Industrial applications of metal-organic frameworks", Chem. Soc. Rev., Mar. 16, 2009, 38, 1284-1293.
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Ociel Esau Andrade Meneses, First Office Action, Application No. MX/E/20131089991, Mexican Institute of Industrial Property (IMPI), Jan. 26, 2015.
Lu et al., "Synthesis and Structure of Chemically Stable Metal-Organic Polyhedra," J. Am. Chem. Soc. 131:(35) 12532-12533 (2009).
Luo et al., "Two new metal-triazole-benzenedicarboxylate frameworks affording an uncommon 3,4-connected net and unique 4,6-connected rod packing: hydrothermal synthesis, structure, thermostability and luminescence studies," CrystEngComm 11(6):1097-1102 (2009).
Ma et al., "Enantioselective catalysis with homochiral metal-organic frameworks", Chem. Soc. Rev., Feb. 23, 2009, 38, 1248-1256.
Mashiyama, Shinya, Office Action issued in Japanese Patent Application No. 2012-522962, Japanese Patent Office, Date of Mailing: May 27, 2014.
McKeown et al., "Phthalocyanine-Based Nanoporous Network Polymers," Chem. Comm. 23:2780-2781 (Oct. 31, 2002).
McKeown et al., "Porphyrin-Based Nanoporous Network Polymers," Chem. Comm. 23:2782-2783 (Oct. 31, 2002).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Moreno-Manas et al., "Palladium-Catalyzed Suzuki-Type Self-Coupling of Arylboronic Acids. A Mechanistic Study", J. Org. Chem., Apr. 1996, 61, 2346-2351.
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).
Morris et al., "Framework mobility in the metal-organic framework crystal IRMOF-3: Evidence for aromatic ring and amine rotation," Journal of Molecular Structure 1004:94-101 (2011).
Morris et al., "Postsynthetic Modification of a Metal-Organic Framework for Stabilization of a Hemiaminal and Ammonia Uptake," Inorg. Chem. 50:6853-6855 (2011).
Morris et al., "NMR and X-ray Study Revealing the Rigidity of Zeolitic Imidazolate Frameworks," J. Phys. Chem. 116 (24):13307-13312 (Jun. 1, 2012).
Morris et al., "Synthesis, Structure, and Metalation of Two New Highly Porous Zirconium Metal-Organic Frameworks," Inorg. Chem. 51:6443-6445 (Jun. 7, 2012).
Moyse, Ellen, International Preliminary Report on Patentability and Written Opinion, Date of Issuance of Report: Nov. 17, 2009, International Application No: PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing 28 Jul. 2011.

(56) References Cited

OTHER PUBLICATIONS

Muller et al., "Chemistry and Applications of Porous Metal-Organic Frameworks", Handbook of Heterogeneous Catalysis, Jan. 1, 2008, vol. 16, pp. 247-262.

Natarajan et al., "Non-carboxylate based metal-organic frameworks (MOFs) and related aspects," Current Opinion in Solid State and Materials Science 13(3-4):46-53 (2009).

Ni et al,. "Porous Metal-Organic Truncated Octahedron Constructed from Paddle-Wheel Squares and Terthiophene Links," J. Am. Chem. Soc. 127:12752-12753 (2005).

Nickitas-Etienne, Athina, International Preliminary Report on Patentability and Written Opinion, Date of Issuance of Report: Jan. 19, 2010, International Application No: PCT/US08/70149.

Nickitas-Etienne, Athina. International Preliminary Report on Patentability for PCT/US2008/07741. Date of issuance of this report: Mar. 30, 2010.

Nickitas-Etienne, Athina. International Preliminary Report on Patentability for PCT/US2009/068849. Date of Mailing: Jun. 30, 2011.

Niu et al., "Synthesis and structural characterization of the one dimensional polymers [Rh2(OAc)4(NCPhCN)S, S=CH3COCH3, CH3OH, C2H5OH, C4H8O, and C6H6," Polyhedron 17(23-24):4079-89 (1998).

Novoa, Carlos, International Search Report and Written Opinion for PCT/US2010/021201, European Patent Office. Date of Mailing: Apr. 27, 2010.

Ockwig et al., "Reticular Chemistry: Occurrence and Taxonomy of Nets, and Grammar for the Design of Frameworks," Acc. Chem. Res. 38:176-182 (2005).

Oisaki et al., "A Metal-Organic Framework with Covalently Bound Organometallic Complexes," J. Am. Chem. Soc. 132:9262-9264 (2010).

O'Keeffe et al., "Germanate Zeolites: Contrasting the Behavior of Germanate and Silicate Structures Built from Cubic T8O20 units (T=Si or Ge)," Chem. Eur. J. 5:2796-2801 (1999).

O'Keeffe et al., "Frameworks for Extended Solids: Geometrical Design Principles," J. Solid State Chem. 152:3-20 (2000).

Okeeffe et al., "Reticular Chemistry—Present and Future Prospects—Introduction,"J. Solid State Chem.178:V-VI (2005).

O'Keeffe et al., "The Reticular Chemistry Structure Resource (RCSR) Database of, and Symbols for, Crystal Nets," Acc. Chem. Res. 41:1782-1789 (2008).

O'Keeffe et al., "Deconstructing the Crystal Structures of Metal-Organic Frameworks and Related Materials into Their Underlying Nets", Chem. Rev. 112(2):675-702 (Feb. 8, 2012).

Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.

Park, H. et al., "Synthesis, Structure Determination and Hydrogen Sorption Studies of New Metal-Organic Frameworks Using Triazole and Naphthalenedicarboxylic Acid," Chem. Natur. 19:1302-1308 (2007).

Park, Jae Woo. International Search Report for PCT/US2010/039123. Date of Mailing: Feb. 24, 2011.

Pawsey et al., "Hyperpolarized 129Xe Nuclear Magnetic Resonance Studies of Isoreticular Metal-Organic Frameworks," Phys. Chem. 111:6060-6067 (2007).

Peterson et al., "Ammonia Vapor Removal by Cu3(BTC)2 and Its Characterization by MAS NMR," J. Phys. Chem. C. 113(32):13906-13917 (2009).

Phan et al., "Synthesis, Structure, and Carbon Dioxide Capture Properties of Zeolitic Imidazolate Frameworks," Acc. Chem. Res 43:58-67 (2009).

Phan et al., "Metal-Organic Frameworks of Vanadium as Catalysts for Conversion of Methane to Acetic Acid," Inorg. Chem. 50:7388-7390 (2011).

Plevert et al., "A Flexible Germanate Structure Containing 24-Ring Channels With Very Low Framework Density," J. Am. Chem. Soc. 123:12706-12707 (2001).

Plevert et al., "Layered Structures Constructed from New Linkages of Ge7(O,OH,F)19 Clusters," Chem. Mater. 15:714-718 (2003).

Plevert et al., "Synthesis and Characterization of Zirconogermanates," Inorg. Chem., 42:5954-5959 (2003).

Queen et al., "Site-Specific CO2 Adsorption and Zero Thermal Expansion in an Anisotropic Pore Network," J. Phys. Chem. C, 115:24915-24919 (Nov. 8, 2011).

Reineke et al., "From Condensed Lanthanide Coordination Solids to Microporous Frameworks Having Accessible Metal Sites," J. Am. Chem. Soc 121:1651-1657 (1999).

Reineke et al., "A Microporosity of Lanthanide-Organic Frameworks," Angew. Chem. Int. Ed. 38:2590-2594 (1999).

Reineke et al., "Large Free Volume In Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).

* cited by examiner

MIL-47

MOF-V150

FUNCTIONALIZATION OF ORGANIC MOLECULES USING METAL-ORGANIC FRAMEWORKS (MOFS) AS CATALYSTS

CROSS REFERENCE TO RELATED APPLICATIONS

This application is a U.S. National Stage Application filed under 35 U.S.C. §371 and claims priority to International Application No. PCT/US2011/044625, filed Jul. 20, 2011, which application claims priority under 35 U.S.C. §119 from Provisional Application Ser. No. 61/365,901, filed Jul. 20, 2010, the disclosures of which are incorporated herein by reference in their entirety.

TECHNICAL FIELD

The disclosure provides organic frameworks for catalyzing the functionalization of organic molecules.

BACKGROUND

The oxidization of alkanes has the important practical implication of providing valuable intermediates for chemical synthesis. Nevertheless, selective oxyfunctionalization of hydrocarbons remains one of the great challenges for contemporary chemistry. Many chemical methods for oxidizing alkanes require severe conditions of temperature or pressure, and the reactions are prone to over-oxidation, producing a range of products, many of which are not desired. In addition, other methods to functionalize hydrocarbons, require using environmentally harmful agents, such as halide gases.

SUMMARY

The disclosure provides a method to replace at least one atom of an organic molecule with another atom or group of atoms by contacting it with a metal organic framework. In one embodiment, the organic molecule is a hydrocarbon. In another embodiment, a hydrogen of the organic molecule is replaced with an oxygen containing functional group. In another embodiment, the method is carried out in the presence of CO. In yet another embodiment, the method is carried out in the presence of an oxidant. In yet another embodiment, the organic molecule is an alkane that is converted to a carboxylic acid. In one embodiment, the metal organic framework comprises a metal or a metal ion comprising an alkali metal, alkaline earth metal, transition metal, lanthanoid, actinoid, metalloid, or post transition metal. In any of the foregoing embodiments, the metal organic framework comprises a metal or a metal ion selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3-}$, $V^{5+}$, $V^{4-}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2-}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $R^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4-}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2-}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $C^{2+}$, $Cu^+$, $Ag^{3+}$, $Ag^{2+}$, $Ag^+$, $Au^{5-}$, $Au^{4+}$, $Au^{3+}$, $Au^{2+}$, $Au^+$, $Zn^{2+}$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4-}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4-}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3-}$, $Yb^{2+}$, and $Lu^3$. In another embodiment, the metal organic framework has a metal or metal ion with a molecular geometry selected from the group consisting of trigonal planar, tetrahedral, square planar, trigonal bipyramidal, square pyramidal, octahedral, trigonal prismatic, pentagonal bipyramidal, paddle-wheel, and square antiprismatic. In yet another embodiment of any of the foregoin the metal organic framework has one or more metals or metal ions with a coordination number selected from the group consisting of 2, 4, 6, and 8. In yet another embodiment, the metal organic framework comprises a plurality of metals or metal ions selected from the group consisting of alkali metal, alkaline earth metal, transition metal, lanthanoid, actinoid, metalloid, and post transition metal. In another embodiment, the metal organic framework has a linking moiety with a parent chain selected from the group consisting of hydrocarbon, hetero-alkane, hetero-alkene, hetero-alkyne, and heterocycle; and wherein the parent chain is functionalized with at least one linking cluster. In another embodiment, the metal organic framework is generated from a linking moiety comprising structural Formula I, II, III, IV, V, VI, VII, VIII, IX and X:

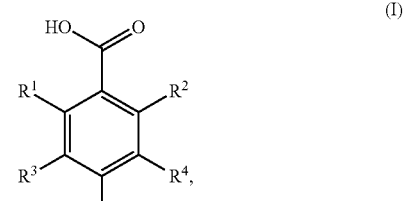

(I)

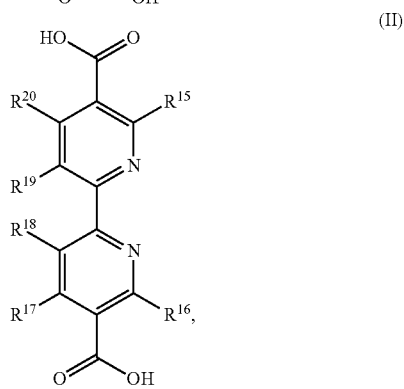

(II)

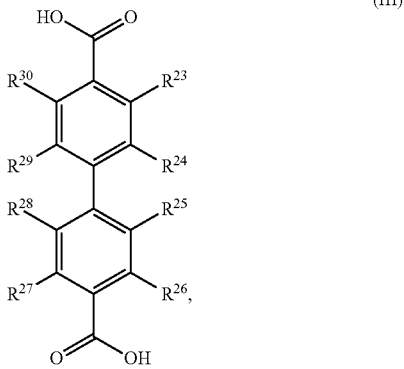

(III)

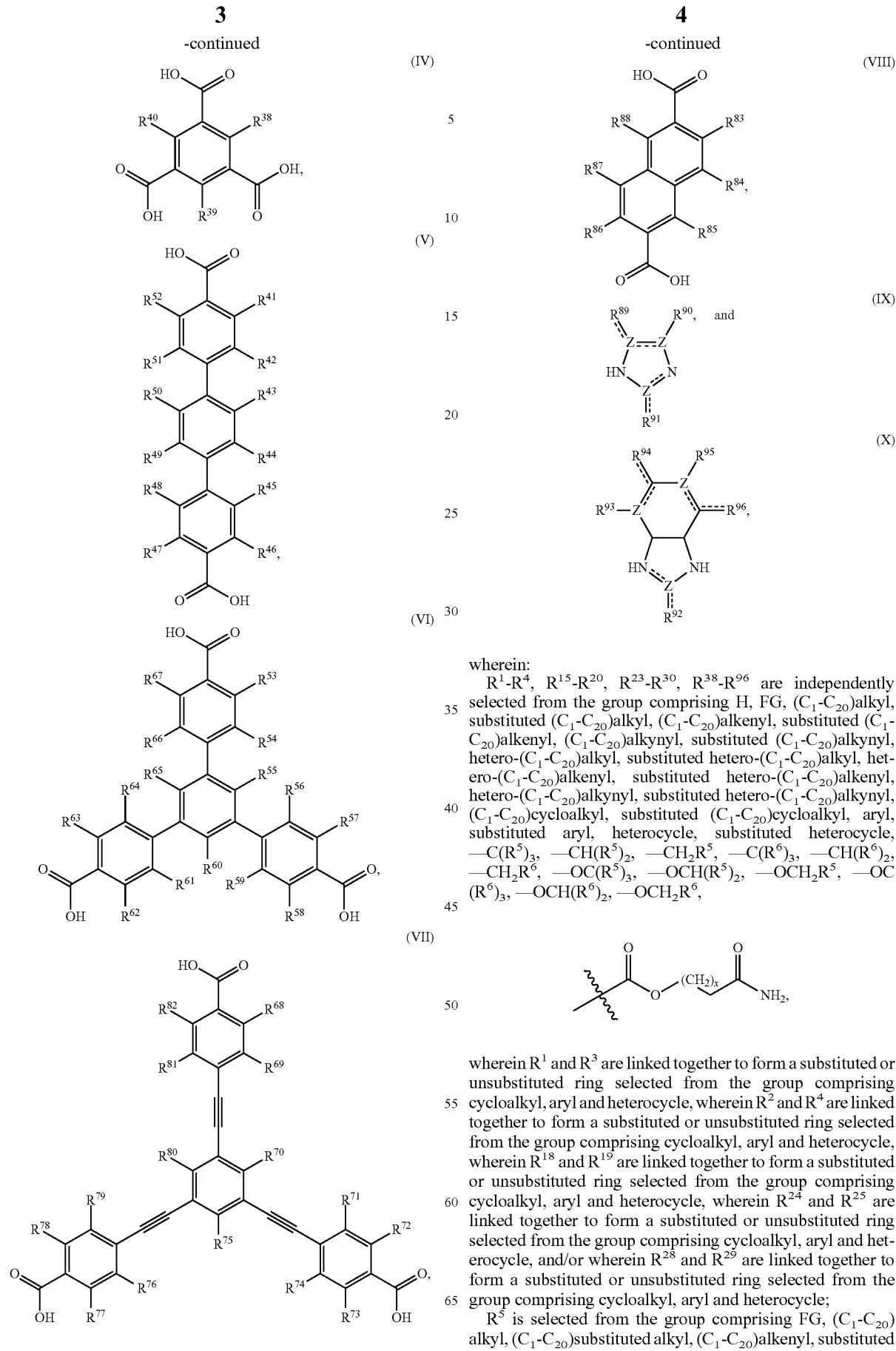

wherein:
R$^1$-R$^4$, R$^{15}$-R$^{20}$, R$^{23}$-R$^{30}$, R$^{38}$-R$^{96}$ are independently selected from the group comprising H, FG, (C$_1$-C$_{20}$)alkyl, substituted (C$_1$-C$_{20}$)alkyl, (C$_1$-C$_{20}$)alkenyl, substituted (C$_1$-C$_{20}$)alkenyl, (C$_1$-C$_{20}$)alkynyl, substituted (C$_1$-C$_{20}$)alkynyl, hetero-(C$_1$-C$_{20}$)alkyl, substituted hetero-(C$_1$-C$_{20}$)alkyl, hetero-(C$_1$-C$_{20}$)alkenyl, substituted hetero-(C$_1$-C$_{20}$)alkenyl, hetero-(C$_1$-C$_{20}$)alkynyl, substituted hetero-(C$_1$-C$_{20}$)alkynyl, (C$_1$-C$_{20}$)cycloalkyl, substituted (C$_1$-C$_{20}$)cycloalkyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$, wherein R$^1$ and R$^3$ are linked together to form a substituted or unsubstituted ring selected from the group comprising cycloalkyl, aryl and heterocycle, wherein R$^2$ and R$^4$ are linked together to form a substituted or unsubstituted ring selected from the group comprising cycloalkyl, aryl and heterocycle, wherein R$^{18}$ and R$^{19}$ are linked together to form a substituted or unsubstituted ring selected from the group comprising cycloalkyl, aryl and heterocycle, wherein R$^{24}$ and R$^{25}$ are linked together to form a substituted or unsubstituted ring selected from the group comprising cycloalkyl, aryl and heterocycle, and/or wherein R$^{28}$ and R$^{29}$ are linked together to form a substituted or unsubstituted ring selected from the group comprising cycloalkyl, aryl and heterocycle;
R$^5$ is selected from the group comprising FG, (C$_1$-C$_{20}$)alkyl, (C$_1$-C$_{20}$)substituted alkyl, (C$_1$-C$_{20}$)alkenyl, substituted ($C_1$-$C_{20}$)alkenyl, ($C_1$-$C_{20}$)alkynyl, substituted ($C_1$-$C_{20}$)alkynyl, hetero-($C_1$-$C_{20}$)alkyl, substituted hetero-($C_1$-$C_{20}$)alkyl, hetero-($C_1$-$C_{20}$)alkenyl, substituted hetero-($C_1$-$C_{20}$)alkenyl, hetero-($C_1$-$C_{20}$)alkynyl, substituted hetero-($C_1$-$C_{20}$)alkynyl, hemiacetal, hemiketal, acetal, ketal, and/or orthoester;

$R_6$ is one or more substituted or unsubstituted rings selected from the group comprising cycloalkyl, aryl, and/or heterocycle; and X is a number from 0 to 10.

In one embodiment, the metal organic framework is generated from a plurality of linking moieties comprising structural Formula I, II, III, IV, V, VI, VII, VIII, IX and X:

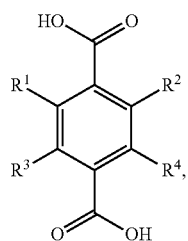
(I)

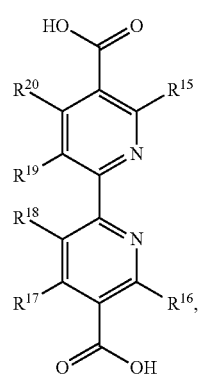
(II)

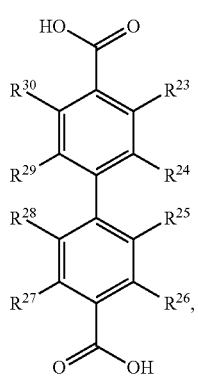
(III)

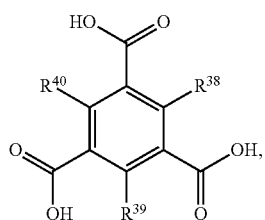
(IV)

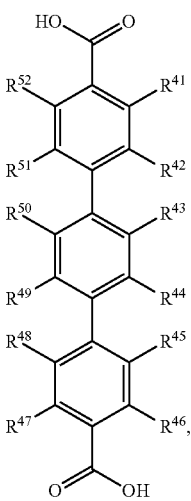
(V)

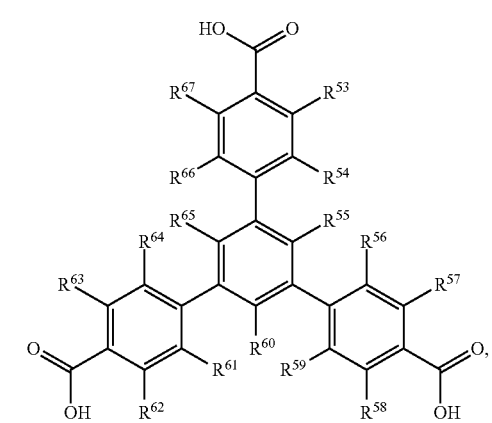
(VI)

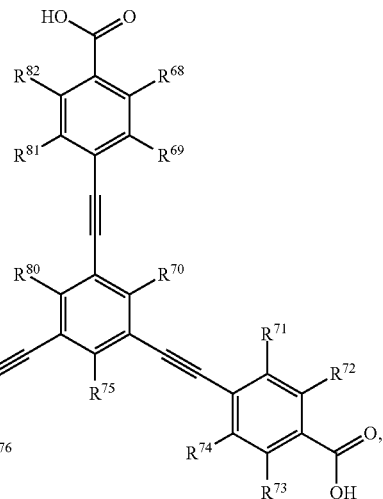
(VII)

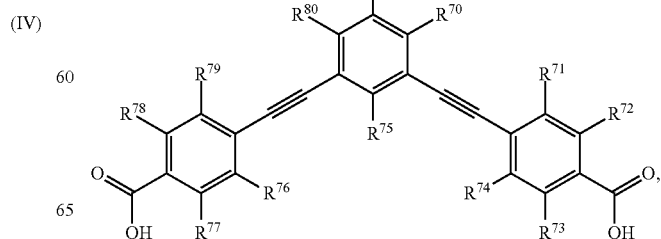

-continued

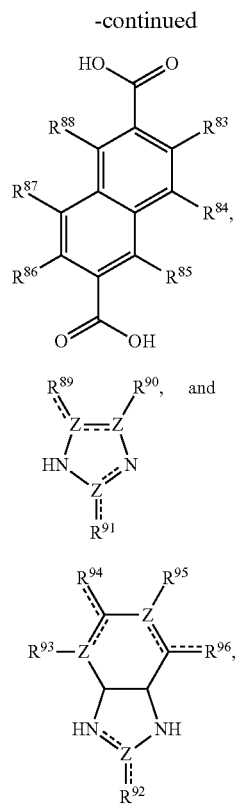

wherein:

$R^1$-$R^4$, $R^{15}$-$R^{20}$, $R^{23}$-$R^{30}$, $R^{38}$-$R^{96}$ are independently selected from the group comprising H, FG, $(C_1$-$C_{20})$alkyl, substituted $(C_1$-$C_{20})$alkyl, $(C_1$-$C_{20})$alkenyl, substituted $(C_1$-$C_{20})$alkenyl, $(C_1$-$C_{20})$alkynyl, substituted $(C_1$-$C_{20})$alkynyl, hetero-$(C_1$-$C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, $(C_1$-$C_{20})$cycloalkyl, substituted $(C_1$-$C_{20})$cycloalkyl, aryl, substituted aryl, heterocycle, substituted heterocycle, —C($R^5$)$_3$, —CH($R^5$)$_2$, —CH$_2$$R^5$, —C($R^6$)$_3$, —CH($R^6$)$_2$, —CH$_2$$R^6$, —OC($R^5$)$_3$, —OCH($R^5$)$_2$, —OCH$_2$$R^5$, —OC($R^6$)$_3$, —OCH($R^6$)$_2$, —OCH$_2$$R^6$,

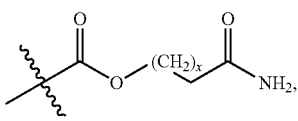

wherein $R^1$ and $R^3$ are linked together to form a substituted or unsubstituted ring selected from the group comprising cycloalkyl, aryl and heterocycle, wherein $R^2$ and $R^4$ are linked together to form a substituted or unsubstituted ring selected from the group comprising cycloalkyl, aryl and heterocycle, wherein $R^{18}$ and $R^{19}$ are linked together to form a substituted or unsubstituted ring selected from the group comprising cycloalkyl, aryl and heterocycle, wherein $R^{24}$ and $R^{25}$ are linked together to form a substituted or unsubstituted ring selected from the group comprising cycloalkyl, aryl and heterocycle, and/or wherein $R^{28}$ and $R^{29}$ are linked together to form a substituted or unsubstituted ring selected from the group comprising cycloalkyl, aryl and heterocycle;

$R^5$ is selected from the group comprising FG, $(C_1$-$C_{20})$alkyl, $(C_1$-$C_{20})$substituted alkyl, $(C_1$-$C_{20})$alkenyl, substituted $(C_1$-$C_{20})$alkenyl, $(C_1$-$C_{20})$alkynyl, substituted $(C_1$-$C_{20})$alkynyl, hetero-$(C_1$-$C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, hemiacetal, hemiketal, acetal, ketal, and/or orthoester;

$R_6$ is one or more substituted or unsubstituted rings selected from the group comprising cycloalkyl, aryl, and/or heterocycle; and X is a number from 0 to 10.

In another embodiment, the metal organic framework is generated from a linking moiety comprising structural Formula I, II, III, IV, V, VI, VII, and VIII:

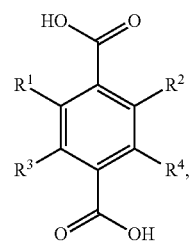

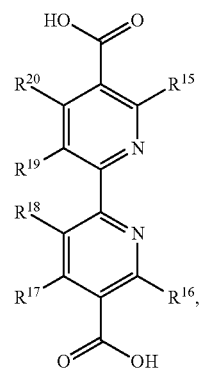

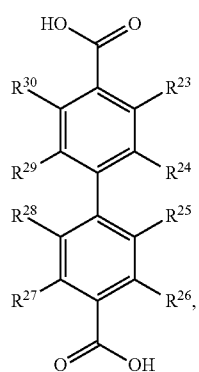

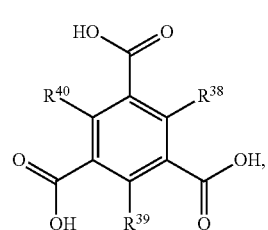

-continued (V)

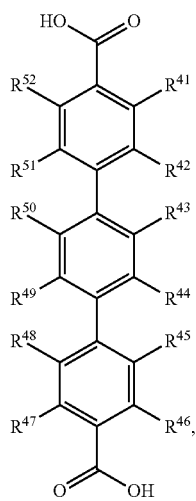

(VI)

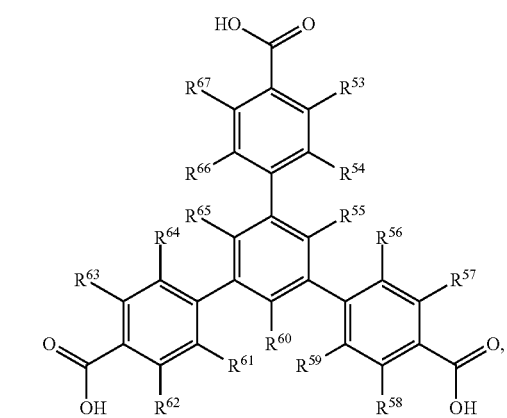

(VII)

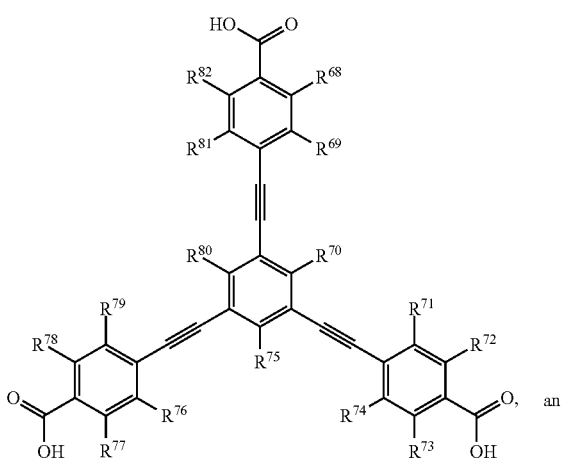

-continued (VIII)

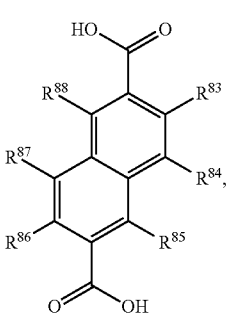

wherein:

$R^1$-$R^4$, $R^{15}$-$R^{20}$, $R^{23}$-$R^{30}$, $R^{38}$-$R^{88}$ are independently selected from the group comprising H, FG, ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, ($C_1$-$C_6$)cycloalkyl, substituted ($C_1$-$C_6$)cycloalkyl, aryl, substituted aryl, heterocycle, substituted heterocycle, —C($R^5$)$_3$, —CH($R^5$)$_2$, —CH$_2$$R^5$, —C($R^6$)$_3$, —CH($R^6$)$_2$, —CH$_2$$R^6$, —OC($R^5$)$_3$, —OCH($R^5$)$_2$, —OCH$_2$$R^5$, —OC($R^6$)$_3$, —OCH($R^6$)$_2$, —OCH$_2$$R^6$,

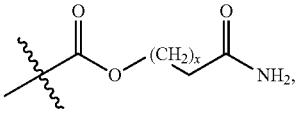

wherein $R^1$ and $R^3$ are linked together to form a substituted or unsubstituted ring selected from the group comprising cycloalkyl, aryl and heterocycle, wherein $R^2$ and $R^4$ are linked together to form a substituted or unsubstituted ring selected from the group comprising cycloalkyl, aryl and heterocycle, wherein $R^{18}$ and $R^{19}$ are linked together to form a substituted or unsubstituted ring selected from the group comprising cycloalkyl, aryl and heterocycle, wherein $R^{24}$ and $R^{25}$ are linked together to form a substituted or unsubstituted ring selected from the group comprising cycloalkyl, aryl and heterocycle, and/or wherein $R^{28}$ and $R^{29}$ are linked together to form a substituted or unsubstituted ring selected from the group comprising cycloalkyl, aryl and heterocycle;

$R^5$ is selected from the group comprising FG, ($C_1$-$C_6$)alkyl, ($C_1$-$C_6$)substituted alkyl, ($C_1$-$C_6$)alkenyl, substituted ($C_1$-$C_6$)alkenyl, ($C_1$-$C_6$)alkynyl, substituted ($C_1$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_1$-$C_6$)alkenyl, hetero-($C_1$-$C_6$)alkynyl, substituted hetero-($C_1$-$C_6$)alkynyl, hemiacetal, hemiketal, acetal, ketal, and/or orthoester;

$R_6$ is one or more substituted or unsubstituted rings selected from the group comprising cycloalkyl, aryl, and/or heterocycle; and X is a number from 0 to 3.

In yet another embodiment, the metal organic framework is generated from a plurality of linking moieties comprising structural Formula I, II, III, IV, V, VI, VII, and VIII:

(I) 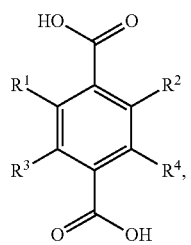
(II) 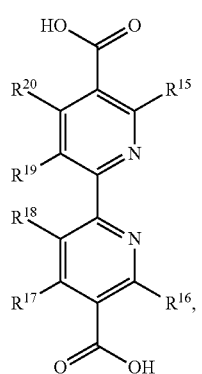
(III) 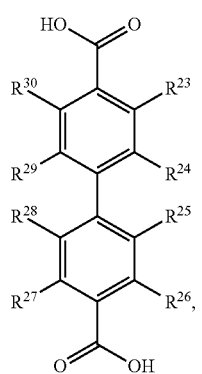
(IV) 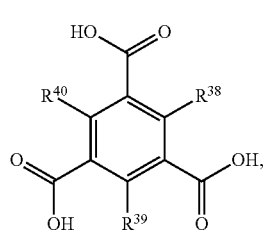
-continued
(V) 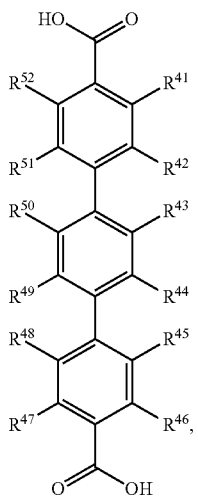
(VI) 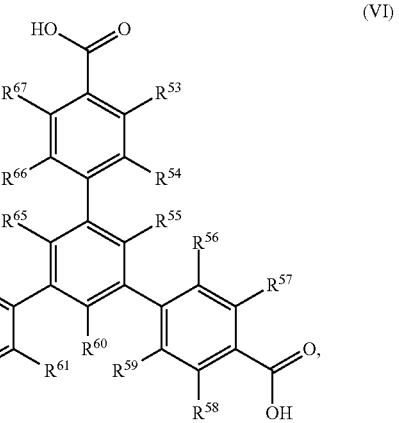
(VII) 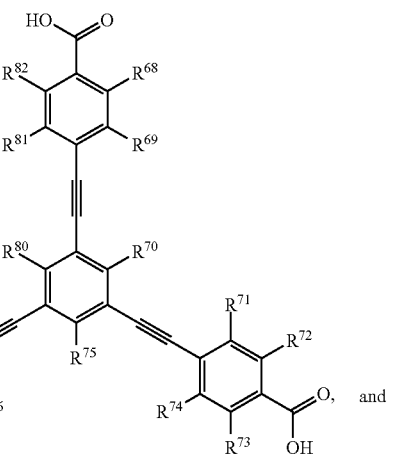
and

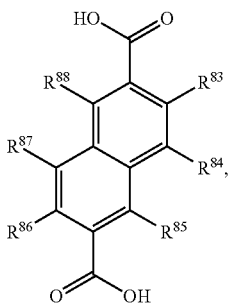

(VIII)

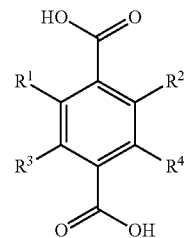

(I)

wherein:

$R^1$-$R^4$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$) alkynyl, hetero-(C$_1$-C$_6$)alkyl, substituted hetero-(C$_1$-C$_6$) alkyl, hetero-(C$_1$-C$_6$)alkenyl, substituted hetero-(C$_2$-C$_6$) alkenyl, hetero-(C$_2$-C$_6$)alkynyl, substituted hetero-(C$_2$-C$_6$) alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$.

wherein:

$R^1$-$R^4$, $R^{15}$-$R^{20}$, $R^{23}$-$R^{30}$, $R^{38}$-$R^{88}$ are independently selected from the group comprising H, FG, (C$_1$-C$_6$)alkyl, substituted (C$_1$-C$_6$)alkyl, (C$_1$-C$_6$)alkenyl, substituted (C$_1$-C$_6$) alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, (C$_1$-C$_6$)cycloalkyl, substituted (C$_1$-C$_6$)cycloalkyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$,

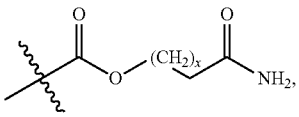

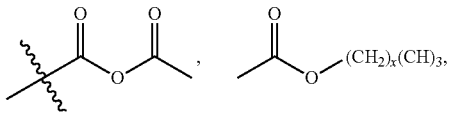

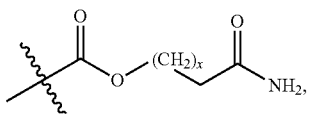

wherein R$^1$ and R$^3$ are linked together to form a substituted or unsubstituted ring selected from the group comprising cycloalkyl, aryl and heterocycle, and/or wherein R$^2$ and R$^4$ are linked together to form a substituted or unsubstituted ring selected from the group comprising cycloalkyl, aryl and heterocycle;

R$^5$ is selected from the group comprising hydroxyl, amine, thiol, cyano, carboxyl, (C$_1$-C$_6$)alkyl, (C$_1$-C$_6$)substituted alkyl, (C$_1$-C$_6$)alkenyl, substituted (C$_2$-C$_6$)alkenyl, (C$_2$-C$_6$) alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, hemiacetal, hemiketal, acetal, ketal, and/or orthoester;

R$_6$ is one or more substituted or unsubstituted rings selected from the group comprising cycloalkyl, aryl, and/or heterocycle; and X is a number from 0 to 3.

In another embodiment, the linking moiety is generated from the group consisting of wherein R$^1$ and R$^3$ are linked together to form a substituted or unsubstituted ring selected from the group comprising cycloalkyl, aryl and heterocycle, wherein R$^2$ and R$^4$ are linked together to form a substituted or unsubstituted ring selected from the group comprising cycloalkyl, aryl and heterocycle, wherein R$^{18}$ and R$^{19}$ are linked together to form a substituted or unsubstituted ring selected from the group comprising cycloalkyl, aryl and heterocycle, wherein R$^{24}$ and R$^{25}$ are linked together to form a substituted or unsubstituted ring selected from the group comprising cycloalkyl, aryl and heterocycle, and/or wherein R$^{28}$ and R$^{29}$ are linked together to form a substituted or unsubstituted ring selected from the group comprising cycloalkyl, aryl and heterocycle;

R$^5$ is selected from the group comprising FG, (C$_1$-C$_6$)alkyl, (C$_1$-C$_6$)substituted alkyl, (C$_1$-C$_6$)alkenyl, substituted (C$_1$-C$_6$) alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, hemiacetal, hemiketal, acetal, ketal, and/or orthoester;

R$_6$ is one or more substituted or unsubstituted rings selected from the group comprising cycloalkyl, aryl, and/or heterocycle; and X is a number from 0 to 3. In another embodiment, the metal organic framework is generated from a linking moiety comprising structural Formula I:

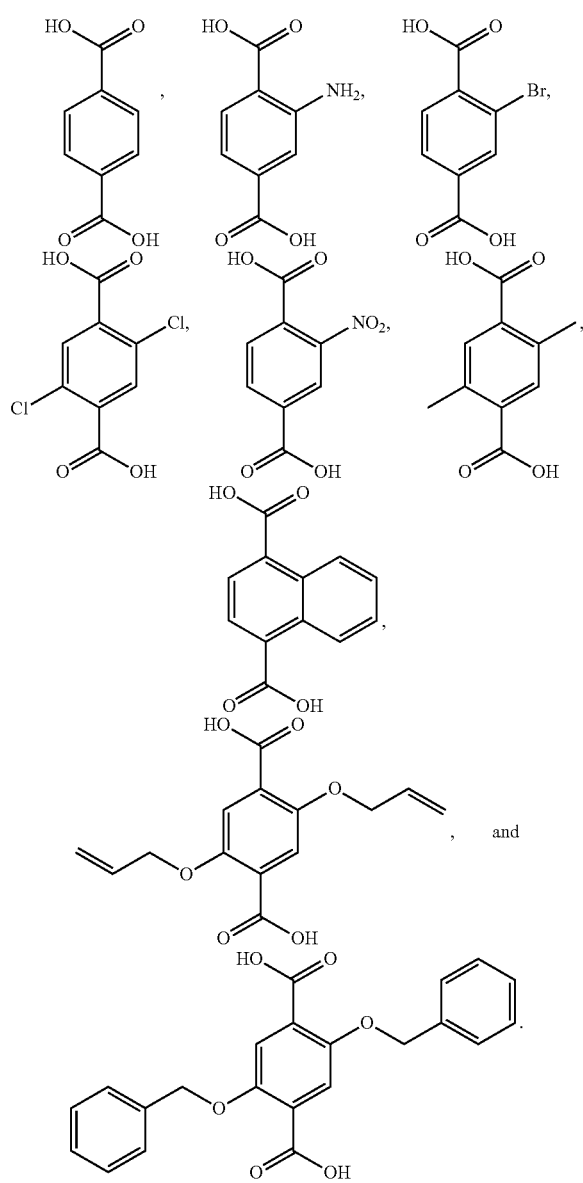

, and

In another embodiment, at least one of the functional groups of the metal organic framework is further modified, substituted, or eliminated with a different functional group post-synthesis of the framework. In one embodiment, the metal organic framework is further modified by adding a functional group post synthesis of the framework that has one or more properties selected from the group consisting of: binds a metal ion, increases the hydrophobicity of the framework, modifies the gas sorption of the framework, modifies the pore size of the framework, and tethers a catalyst to the framework. In yet another embodiment, the metal organic framework is a composition comprising a vanadium containing metal organic framework.

This disclosure describes a heterogeneous and efficient route to functionalize various types of organic molecules by replacing an atom from an organic molecule with another atom or a group of atoms. It was surprisingly found that metal organic frameworks (MOFs), e.g., vanadium containing MOFs, and other MOFs catalyze the oxidation of various types of alkanes, in the presence or absence of carbon monoxide, to form oxidized products, including alcohols, homologous carboxylic acids, and carboxylic acids. In one embodiment, the reaction is carried out in trifluoroacetic acid (TFA), wherein the desired alcohol is trapped as the corresponding TFA ester. Potassium persulfate (KPS) is used as an oxidant, although water and hydrogen peroxide can alternatively be used as the solvent and oxidant, respectively. In one embodiment, the disclosure provides a method to convert methane to acetic acid and ethane to propanoic acid by contacting with a MOF disclosed herein. Further transformations, however, are possible by using the appropriate linker molecule and/or appropriate post synthesized framework reactant.

MOF-V150 was obtained by reacting 2,5-dimethyl-benzen-dicarboxylic and vanadium (IV) oxide ($VO_2$) in hydrochloric acid and water at 220° C. for 3 days.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
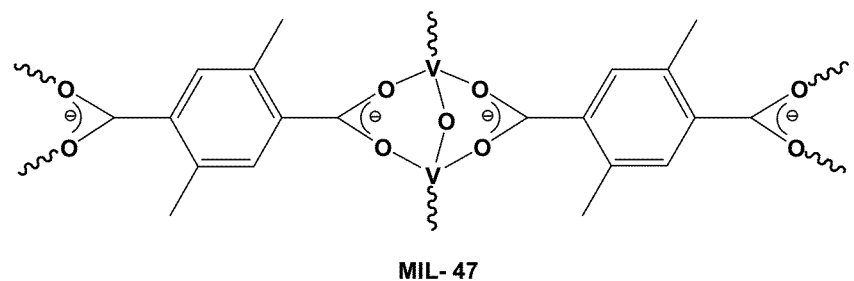
FIG. 1 shows the coordination complex of MIL-47 and MOF-V150, wherein each V is coordinated by four $\mu^2$-carboxylate moieties and two $\mu^2$-oxo groups forming an octahedral coordination sphere.
Figure 1:
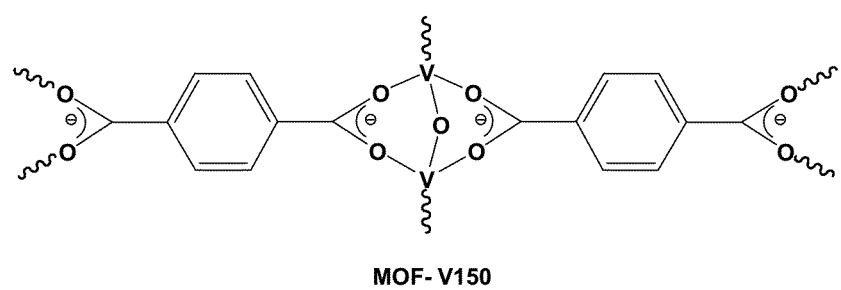

As used herein and in the appended claims, the singular forms "a," "and," and "the" include plural referents unless the context clearly dictates otherwise. Thus, for example, reference to "a framework" includes a plurality of such frameworks and reference to "the metal" includes reference to one or more metals and equivalents thereof known to those skilled in the art, and so forth.

Unless defined otherwise, all technical and scientific terms used herein have the same meaning as commonly understood to one of ordinary skill in the art to which this disclosure belongs. Although many methods and reagents similar or equivalent to those described herein can be used in the practice of the disclosed methods and compositions, the exemplary methods and materials are disclosed herein.

Also, the use of "and" means "and/or" unless stated otherwise. Similarly, "comprise," "comprises," "comprising"

"include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of metal. Metal ions are generally Lewis Acids and can form coordination complexes. Typically, the metal ions used for forming a coordination complex in a framework are ions of transition metals.

A "ligand" refers to an atom, or a group of atoms, that have denticity and are therefore able to form at least one bond with at least one metal or metal ion from a parental chain (e.g., a linking moiety substructure).

The term "cluster" refers to identifiable associations of 2 or more atoms. Such associations are typically established by some type of bond-ionic, covalent, Van der Waal, coordinate and the like. A cluster can be a ligand, except when the cluster is a linking cluster.

The term "linking cluster" refers to one or more reactive species capable of condensation comprising an atom capable of forming a bond between a linking moiety parent chain (e.g., substructure) and a metal group or between a linking moiety and another linking moiety. A linking cluster would include a coordination complex defined herein. A linking cluster can be part of the parent chain itself, e.g. imidiazoles, or alternatively can arise from functionalizing the parent chain, e.g. adding carboxylic acid groups to aryls. Examples of such reactive species include, but is not limited to, boron, oxygen, carbon, nitrogen, silicon, tin, germanium, arsenic, and phosphorous. In certain embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Typically linking clusters for binding metals in the generation of MOFs contain carboxylic acid functional groups. Linking clusters are generally Lewis bases, and therefore have lone pair electrons available and/or can be deprotonated to form stronger Lewis bases. The deprotonated version of the linking clusters, therefore, is encompassed by invention and anywhere a linking cluster that is depicted in a nondeprotenated form, the deprotenated form should be presumed to be included, unless stated otherwise. For example, although the structural Formulas presented herein are illustrated as having carboxylic acid ligands, for the purposes of this invention, these illustrated structures should be interpreted as including both carboxylic acid and/or carboxylate ligands.

The term "coordination number" refers to the number of atoms, groups of atoms, or linking clusters that bind to a central metal or metal ion where only the sigma bond between each atom, groups of atoms, or linking cluster and the central atom counts.

The term "coordination complex" refers to a metal or a metal ion that is coordinated by one or more linking clusters and/or ligands of one or more linking moieties and/or ions by forming coordinate bonds with a central metal or metal ion. For purposes of this invention a "coordination complex" includes complexes arising from linking moieties that have mono-dentate and/or polydentate ligands.

The term "denticity" or "dentate" with respect to mono-dentate or polydentate, refers to the number of atoms of a ligand, which can form a bond to a metal and/or metal ion in a coordination complex. Examples of polydentate functional groups, include, but are not limited to, carboxylic acids, diamines, diimines, dithiolates, diketonates, bipyrimidinyls, diphosphinos, oxalates, tri-aza-based compounds, and tetra-aza-based compounds. It is understood that ligands possessing monodentate and/or polydentate functional groups bring with them corresponding counter cations, such as $H^+$, $Na^+$, $K^+$, $Mg^{2-}$, $Ca^{2+}$, $Sr^{2+}$, ammonium ions, alkyl substituted ammonium ions, and aryl substituted ammonium ions; or with corresponding counter anions, such as $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^-$, $SO_3^-$, $PO_3^-$, $CO_3^-$, $PF_6^-$, and organic counter ions such as acetate $CH_3CO_2^-$, triflates $CF_3SO_3-$, mesylates $CH_3SO_3^-$, tosylates $CH_3C_6H_4SO_3$, and the like.

A "linking moiety" refers to an organic compound which can form a coordination complex with one or more metal and/or metal ions. Generally, a linking moiety comprises a parent chain of a hydrocarbon, hetero-alkane, hetero-alkene, hetero-alkyne, or heterocycles; where this parent chain may be substituted with one or more functional groups, including additional substituted or unsubstituted hydrocarbons, and heterocycles, or a combination thereof; and wherein the linking moiety contains at least one linking cluster. In the case of heterocycles, hetero-alkanes, hetero-alkenes, and hetero-alkynes, one or more heteroatoms can function as linking clusters or alternatively as ligands. Examples of such heteroatoms include, but are not limited to, nitrogen, oxygen, sulfur, boron, phosphorus, silicon or aluminum atoms making up the ring. Moreover, a heterocycle, hetero-alkane, hetero-alkene, or hetero-alkyne, can also be functionalized with one or more linking clusters. Moreover, a heterocycle, hetero-alkane, hetero-alkene, or hetero-alkyne, can also be functionalized with one or more ligands to add or increase denticity of the hetero-based parent chain. In the case of hydrocarbons, typically one or more of the linking clusters of the hydrocarbon-based linking moiety can arise from functionalizing the hydrocarbon parent chain with one or more functional groups that can then act as a linking cluster. Examples of such groups, include, but are not limited to, carboxylic acids, hydroxyls, amines, imines, thiols, phosphines, ketones, aldehydes, halides, cyanos, and nitros. In certain cases, portions of a hydrocarbon itself can function as ligand, for example by forming carbenes and carbocations. It is also well known that functional groups that can be ligands are generally Lewis bases, and therefore have lone pair electrons available and/or can be deprotonated to form stronger Lewis bases. The deprotonated version of the ligand, therefore, is encompassed by invention and anywhere a ligand that is depicted in a non-deprotenated form, the deprotenated form should be presumed to be included, unless stated otherwise. For example, although the structural Formulas presented herein are illustrated as having carboxylic acid ligands, for the purposes of this invention, those illustrated structures should be interpreted as including both carboxylic acid and/or carboxylate ligands.

The term "alkyl" refers to an alkyl group that contains 1 to 30 carbon atoms. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl" refers to an alkenyl group that contains 1 to 30 carbon atoms. While a $C_1$ alkenyl can form a double bond to a carbon of a parent chain, an alkenyl group of three or more carbons can contain more than one double bond. it certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl" refers to an alkynyl group that contains 1 to 30 carbon atoms. While a $C_1$ alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl" refers to an alkyl that contains at least 3 carbon atoms but no more than 12 carbon atoms connected so that it forms a ring. A "cycloalkyl" for the purposes of this invention encompass from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstitued, one or more rings may be substituted, or a combination thereof.

The term "aryl" refers to a conjugated planar ring system with delocalized pi electron clouds that contain only carbon as ring atoms. An "aryl" for the purposes of this invention encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle" refers to ring structures that contain at least 1 noncarbon ring atom. A "heterocycle" for the purposes of this invention encompass from 1 to 7 heterocycle rings wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is either N, O, S, Si, Al, B, or P. In case where there is more than one noncarbon ring atom, these noncarbon ring atoms can either be the same atom, or combination of different elements, such as N and O. Examples of heterocycles include, but is not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing one hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but is not limited to, quinuclidinyl, diazabicyclo[2.2.1]heptyl; and 7-oxabicyclo[2.2.1]heptyl.

The term "hetero-aryl" used alone or as a suffix or prefix, refers to a heterocyclyl having aromatic character. Examples of heteroaryls include, but is not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this invention refers to the specified hydrocarbon having one or more carbon atoms replaced by non carbon atoms as part of the parent chain. Examples of such noncarbon atoms include, but is not limited to, N, O, S, Si, Al, B, and P. If there is more than one noncarbon atom in the hetero-hydrocarbon chain then this atom may be the same element or may be a combination of different elements, such as N and O.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this invention, a substituent would include deuterium atoms.

The term "hydrocarbons" refers to groups of atoms that contain only carbon and hydrogen. Examples of hydrocarbons that can be used in this invention include, but is not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this invention, include, but is not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted heteroaryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

As used herein, a "core" refers to a repeating unit or units found in a framework. Such a framework can comprise a homogenous repeating core, a heterogeneous repeating core or a combination of homogenous and heterogeneous cores. A core comprises a metal and/or metal ion or a cluster of metal and/or metal ions and a linking moiety.

As used herein, a "framework" refers to crystalline structure consisting of plurality of cores to form one-, two-, or three-dimensional structures that may or may not be porous. In some cases, the pores are stable to elimination of the guest molecules (often solvents).

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise a plurality of linking moieties linking together polydentate cores such that the spatial structure of the network is a polyhedron. Typically, the polyhedra of this variation are 2 or 3 dimensional structures.

The term "post framework reactants" refers to all known substances that are directly involved in a chemical reaction. Post framework reactants typically are substances, either elemental or compounds, which have not reached the optimum number of electrons in their outer valence levels, and/or have not reached the most favorable energetic state due to ring strain, bond length, low bond dissociation energy, and the like. Some examples of post framework reactants include, but are not limited to:

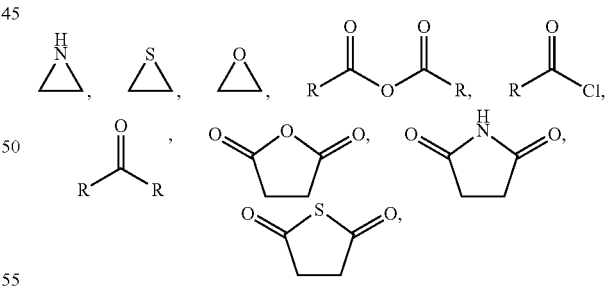

I—R, Br—R, $CR_3$—Mg—Br, $CH_2R$—Li, $CR_3$, Na—R, and K—R; and wherein each R is independently selected from the group comprising: H, sulfonates, tosylates, azides, triflates, ylides, alkyl, aryl, OH, alkoxy, alkenes, alkynes, phenyl and substitutions of the foregoing, sulfur-containing groups (e.g., thioalkoxy, thionyl chloride), silicon-containing groups, nitrogen-containing groups (e.g., amides and amines), oxygen-containing groups (e.g., ketones, carbonates, aldehydes, esters, ethers, and anhydrides), halogen, nitro, nitrile, nitrate, nitroso, amino, cyano, ureas, boron-containing groups (e.g., sodium borohydride, and catecholborane), phosphorus-containing groups (e.g., phosphorous tribromide), and aluminum-containing groups (e.g., lithium aluminum hydride).

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates a bond that may be a single covalent bond or alternatively a double covalent bond. But in the case where an R group defines an atom that is connected to another atom by a straight line and a dashed line which would exceed its maximum valence if the bond was a double covalent bond then the bond would only be a single covalent bond. For example, where R can be hydrogen and is connected to another atom by a straight line and a dashed line, then hydrogen would only form a single bond even though such a bond is indicated as being a single or double bond.

Methane, the main component of natural gas, is an abundant, clean burning, but relatively potent greenhouse gas. A long existing challenge, due to the strong C—H bonds of methane (435 kJ mol$^{-1}$), is to directly convert this inexpensive carbon source to other useful molecules. Many potential catalysts for the transformation of methane to useful raw materials for the chemical industry, including acetic acid (AcOH), have been investigated. Currently, the production of acetic acid on an industrial scale involves three steps: the partial-oxidation of methane to syn-gas using metal catalysts at high temperatures, followed by the conversion of the derived syn-gas to methanol, and finally, the carbonylation of methanol to obtain acetic acid. These processes use expensive catalyst systems containing either Rh or Ir compounds and require huge inputs of energy and capital.

Many efforts have been made to identify potential catalysts and oxidative processes to convert methane directly to acetic acid at low temperatures in an efficient and inexpensive manner. However, most existing catalytic systems and oxidative processes to convert methane to acetic acid suffer from high costs and low yields. Furthermore, these catalyst systems are homogeneous. For a large scale process like the acetic acid synthesis, a heterogeneous catalyst is preferable. Reported heterogeneous catalysts like copper-cobalt-based materials, palladium on carbon or alumina, rhodium on silica and ZrSO$_4$ show even lower product yield and use higher temperatures (>200° C.) than the homogeneous catalyst systems. Some progress has been made with homogeneous catalysts. Recently, Periana et al. demonstrated that Pd$^{II}$ catalyzed the oxidative carbonylation of methane to acetic acid at 180° C. in sulfuric acid, with an approximate yield of 10%. Also, vanadium complexes (e.g, Amavandin complexes or V(O)(acac)$_2$) have been reported to be catalytically active in the conversion of methane to acetic acid at 80° C. in trifluoroacetic acid (TFA) as the solvent and potassium peroxydisulfate (KPS) as the oxidant. These are homogeneous catalysts that generate low absolute yields corresponding with high TON or vice versa, and lack selectivity. However, no effective heterogeneous catalyst providing high yields, low TON, and selectivity has yet been discovered.

The disclosure provides for a method to replace at least one atom of an organic molecule with another atom or group of atoms by contacting the organic molecule with a metal organic framework disclosed herein. Examples of organic molecules that can be modified or acted on, include, but are not limited to, hydrocarbons, hetero-alkanes, hetero-alkenes, hetero-alkynes, heterocycles, alkyl halides, alcohols, carbonyls, amines, aldehydes, ketones, esters, ethers, carboxylic acids, amides, thiols, heterocycles, peroxides and the like. In a certain embodiment, the organic molecule is a hydrocarbon. In a further embodiment, the organic molecule is a hydrocarbon selected from the group comprising linear alkanes, branched alkanes and cycloalkanes. In yet another embodiment, the organic molecule is a linear ($C_1$-$C_{12}$) alkane.

In another embodiment, the method homolytically cleaves a bond between the atom to be replaced and the organic molecule.

In yet another embodiment, the method heterolytically cleaves a bond between the atom to be replaced and the organic molecule.

In a certain embodiment, one or more of the atoms being replaced are hydrogen atoms. In a further embodiment, one or more of the hydrogen atoms being replaced are connected to carbon atoms. In another embodiment, one or more of the hydrogen atoms being replaced are connected to primary carbon atoms. In yet a further embodiment, one or more of the hydrogen atoms being replaced are connected to a carbon atom of a hydrocarbon molecule. In another embodiment, one or more of the hydrogen atoms being replaced are connected to a carbon atom of an alkane. In a certain embodiment, one or more of the hydrogen atoms being replaced are connected to a carbon atom of an n-alkane. In yet another embodiment, one or more of the hydrogen atoms being replaced are connected to a carbon atom of a ($C_1$-$C_{12}$)alkane. In a further embodiment, one or more of the hydrogen atoms being replaced are connected to a carbon atom of a linear ($C_1$-$C_{12}$)-alkane. In another embodiment, one or more of the hydrogen atoms being replaced are from a methane molecule. In yet another embodiment, one or more of the hydrogen atoms being replaced are from an ethane molecule.

In a certain embodiment, one or more of the organic molecule's atoms are being replaced with hydrogen, a deuterium, a nonmetal atom or a metalloid atom. In a further embodiment, one or more of the organic molecule's atoms are replaced with a nonmetal atom. In a yet further embodiment, one or more of the organic molecule's atoms are replaced with a nonmetal atom selected from the following: N, O, F, S, Cl, Se, Br, and I. In another embodiment, one or more of the organic molecule's atoms are replaced with a O, F, Cl, Br or I. In a further embodiment, a hydrogen atom of an alkane is replaced with an O.

In another embodiment, one or more of the organic molecule's atoms are replaced with a group of atoms containing one or more hydrogens, deuteriums, nonmetal atoms, metalloid atoms, or metals. In a further embodiment, one or more of the organic molecule's atoms are replaced with a functional group which contains more than one atom. In yet a further embodiment, one or more of the organic molecule's atoms are replaced with an oxygen containing functional group. In another embodiment, one or more of the organic molecule's atoms are replaced with a hydroxyl, aldehyde, ketone, carboxylic acid, ether, ester, or anhydride. In yet another embodiment, one or more of the organic molecule's atoms are replaced with a carboxylic acid group. In a further embodiment, one or more of the organic molecule's atoms being replaced are replaced with a hydroxyl group.

The disclosure further provides for a method to replace at least one atom of an organic molecule with another atom or group of atoms in the presence of carbon monoxide by contacting the organic molecule with a metal organic framework disclosed herein. In a certain embodiment, when the method is performed in the presence of carbon monoxide, one or more of the organic molecule's atoms are replaced with carbon monoxide or a larger functional group resulting from incorporating a carbon monoxide molecule.

The disclosure further provides for a method to replace at least one atom of an organic molecule with another atom or group of atoms in the presence of oxidant by contacting the organic molecule with a metal organic framework disclosed herein. In a certain embodiment, when the method is performed in the presence of an oxidant, one or more the hydrogen atoms are replaced with an oxygen and/or an oxygen containing functional group. Examples of oxidants, include, but are not limited to hydrogen peroxide and $K_2S_2O_8$.

The disclosure further provides for a method to replace at least one atom of an organic molecule with another atom or group of atoms in the presence of oxidant and in the presence of carbon monoxide by contacting the organic molecule with a metal organic framework disclosed herein. In a certain embodiment, when the method is performed in the presence of an oxidant and in the presence of carbon monoxide, one or more of the hydrogen atoms will be replaced with carbon monoxide and/or an oxygen containing functional group which has incorporated a carbon monoxide molecule.

In a certain embodiment, the method disclosed herein results in oxidizing an organic molecule. In a further embodiment, the method disclosed herein results in converting an alkane to a carboxylic acid. In a certain embodiment, the method disclosed herein converts methane into acetic acid. In another embodiment, the method disclosed herein converts ethane into propanoic acid or acetic acid. In yet a further embodiment, the method disclosed herein converts ethane into propanoic acid.

In a further embodiment, the metal organic framework used in any of the methods above is comprised of a single type of metal or metal ion, and a single type of linking moiety.

In another embodiment, the metal organic framework is comprised of two or more different metal and/or metal ions, and a single type of linking moiety.

In another embodiment, the metal organic framework is comprised of a single type of metal or metal ion, and two or more different types of linking moieties.

In a certain embodiment, a composition comprising a metal organic framework for carrying out the methods disclosed herein. In another embodiment, a composition comprising a Formula I containing metal organic framework for carrying out the methods disclosed herein. In yet another embodiment, a composition comprising a Formula II containing metal organic framework for carrying out the methods disclosed herein. In a further embodiment, a composition comprising a vanadium containing metal organic framework for carrying out the methods disclosed herein. In a further embodiment, a composition comprising a vanadium and Formula I containing metal organic framework for carrying out the methods disclosed herein. In another embodiment, a composition comprising a vanadium and Formula II containing metal organic framework for carrying out the methods disclosed herein.

Metals and their associated ions that can be used in the synthesis of the metal organic frameworks disclosed herein are selected from the group comprising alkali metals, alkaline earth metals, transition metals, lanthanoids, actinoids, metalloids, and post transition metals. Metal and/or metal ions can be introduced into open frameworks, MOFs, ZIFs, and COFs, via forming complexes with one or more ligands in a framework or by simple ion exchange. Therefore, it is reasonable to assume that any metal and/or metal ion disclosed herein can be introduced. Moreover, post synthesis of the framework, metal and/or metal ions may be exchanged by commonly known techniques, and/or additional metal ions can be added to the framework by forming coordination complexes with functional groups arising from post framework reactants.

In an embodiment, one or more metals and/or metal ions that can be used in the (1) synthesis of frameworks, (2) exchanged post synthesis of the frameworks, and/or (3) added to framework by forming coordination complexes with post framework reactant functional group(s), include, but are not limited to, alkali metals, alkaline earth metals, transition metals, lanthanoids, actinoids, metalloids, and post transition metals.

In a certain embodiment, one or more metals and/or metal ions that can be used in the (1) synthesis of frameworks, (2) exchanged post synthesis of the frameworks, and/or (3) added to framework by forming coordination complexes with post framework reactant functional group(s), include, but are not limited to $Li^+$, $Na^+$, $K^+$, $Rb^+$, $Cs^+$, $Be^{2+}$, $Mg^{2+}$, $Ca^{2+}$, $Sr^{2+}$, $Ba^{2-}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5-}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^2$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3-}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6-}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4-}$, $Fe^{3+}$, $Fe^{2-}$, $Fe^+$, $Fe$, $Ru^{8-}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3-}$, $Co^{2+}$, $Co^+$, $Rh^{6+}$, $Rh^{5+}$, $Rh^{4-}$, $Rh^{3+}$, $Rh^{2+}$, $Rh^+$, $Ir^{6+}$, $Ir^{5+}$, $Ir^{4+}$, $Ir^{3-}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3-}$, $Db^{2+}$, $Ho^{3+}$, $Er^{3+}$, $Tm^{4+}$, $Tm^{3+}$, $Tm^{2+}$, $Yb^{3+}$, $Lu^{3+}$, and any combination thereof, along with corresponding metal salt counter-anions.

In a further embodiment, one or more metal ions that can be used in the (1) synthesis of frameworks, (2) exchanged post synthesis of the frameworks, and/or (3) added to framework by forming coordination complexes with post framework reactant functional group(s), include, but are not limited to, $Li^+$, $Na^+$, $Rb^-$, $Mg^{2+}$, $Ca^{2+}$, $Sr^{2+}$, $Ba^{2+}$, $Sc^{3-}$, $Ti^{4+}$, $Zr^{4+}$, $Hf^{4-}$, $V^{5+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3-}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2-}$, $Pd^{2+}$, $Pd^+$, $Pt^{2+}$, $Pt^+$, $Cu^{2+}$, $Cu^-$, $Ag^+$, $Au^+$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2-}$, $Ge^{4+}$, $Ge^{2+}$, $Sn^{4+}$, $Sn^{2+}$, $Pb^{2+}$, $Pb^{4+}$, $As^{5+}$, $As^{3+}$, $As^-$, $Sb^{5+}$, $Sb^{3+}$, $Sb^+$, $Bi^{5+}$, $Bi^{3+}$, and combinations thereof, along with corresponding metal salt counter-anions.

In yet a further embodiment, one or more metal ions that can be used in the (1) synthesis of frameworks, (2) exchanged post synthesis of the frameworks, and/or (3) added to framework by forming coordination complexes with post framework reactant functional group(s), include, but are not limited to, $Li^+$, $Na^+$, $Rb^-$, $Mg^{2+}$, $Ca^{2+}$, $Sr^{2+}$, $Ba^{2+}$, $Sc^{3-}$, $Ti^{4+}$, $Zr^{4+}$, $Ta^{3-}$, $V^{5+}$, $V^{4+}$, $V^{3+}$, $V^{2+}$, $Cr^{3+}$, $Mo^{3+}$, $W^{3+}$, $Mn^{3-}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3-}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and any combination thereof, along with corresponding metal salt counter-anions.

In a certain embodiment, one or more metal ions used in the (1) synthesis of frameworks, (2) exchanged post synthesis of the frameworks, and/or (3) added to framework by forming coordination complexes with post framework reactant functional group(s), include, but are not limited to, $Sc^{3+}$, $Sc^{2+}$, $Sc^+$, $Ti^{4+}$, $Ti^{3+}$, $Ti^{2+}$, $Pd^6$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Fc^{6+}$, $Fc^{4+}$, $Fc^{3+}$, $Fc^{2+}$, $Fc^+$, $Fc$, $Hg^{4+}$, $Hg^{2+}$, $Hg^+$, $Cu^{4+}$, $Cu^{3+}$, $Cu^{2+}$, $Cu^+$, $Al^{3+}$, $Al^{2+}$, $Al^+$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $V^{5+}$, $V^{4+}$, $V^{3-}$, and $V^{2+}$.

In another embodiment, one or more metal ions in the (1) synthesis of frameworks, (2) exchanged post synthesis of the frameworks, and/or (3) added to framework by forming coordination complexes with post framework reactant functional group(s), is a vanadium ion selected from the group comprising $V^{5+}$, $V^{4+}$, $V^{3+}$, and $V^{2+}$.

In a certain embodiment, the metal ion used in the synthesis of the metal organic framework is a vanadium ion selected from the group comprising $V^{5+}$, $V^{4+}$, $V^{3+}$, and $V^{2+}$.

Linking moiety ligands and/or post frameworks reactants ligands can be selected based on Hard Soft Acid Base theory (HSAB) to optimize the interaction between the ligands and a metal or metal ion disclosed herein. In certain cases the metal and ligands are selected to be a hard acid and hard base, wherein the ligands and the metals will have the following characteristics: small atomic/ionic radius, high oxidation state, low polarizability, hard electronegativity (bases), highest-occupied molecular orbitals (HOMO) of the hard base is low in energy, and lowest unoccupied molecular orbitals (LUMO) of the hard acid are of high energy. Generally hard base ligands contain oxygen. Typical hard metal and metal ions include alkali metals, and transition metals such as Fe, Cr, and V in higher oxidation states. In other cases the metal and ligands are selected to be a soft acid and a soft base, wherein the ligands and the metal or metal ions will have the following characteristics: large atomic/ionic radius, low or zero oxidation state, high polarizability, low electronegativity, soft bases have HOMO of higher energy than hard bases, and soft acids have LUMO of lower energy than hard acids. Generally soft base ligands contain sulfur, phosphorous, and larger halides. In other cases the metal and ligands are selected to be a borderline acid and a borderline base. In certain cases, the metal and ligands are selected so that they are hard and soft, hard and borderline, or borderline and soft.

In an embodiment, the metal and/or metal ion that can be used in the (1) synthesis of the metal organic frameworks, (2) exchanged post synthesis of the metal organic frameworks, and/or (3) added to the metal organic framework by forming coordination complexes with post framework reactant functional group(s) is a HSAB hard metal and/or metal ion. In yet further embodiments, the metal and/or metal ion that can be used in the (1) synthesis of frameworks, (2) exchanged post synthesis of the frameworks, and/or (3) added to framework by forming coordination complexes with post framework reactant functional group(s) is a HSAB soft metal and/or metal ion. In even further embodiments, the metal and/or metal ion that can be used in the (1) synthesis of the metal organic frameworks, (2) exchanged post synthesis of the metal organic frameworks, and/or (3) added to the metal organic framework by forming coordination complexes with post framework reactant functional group(s) is a HSAB borderline metal and/or metal ion. In the case that there is a plurality of metal and/or metal ions used in the (1) synthesis of the metal organic frameworks, (2) exchanged post synthesis of the metal organic frameworks, and/or (3) added to the metal organic framework by forming coordination complexes with post framework reactant functional group(s) then there can be any combination of hard, soft and borderline metals and/or metal ions that can be used in or attached to the metal organic framework.

In a further embodiment, one or more metals and/or metal ions that can be used in the (1) synthesis of the frameworks, (2) exchanged post synthesis of the frameworks, and/or (3) added to the frameworks by forming coordination complexes with post framework reactant functional group(s) has a coordination number selected from the following: 2, 4, 6, and 8. In another embodiment, one or more metals and/or metal ions has a coordination number of 4 and 6. In yet another embodiment, the metal and/or metal ions has a coordination number of 6.

In a further embodiment, the metal and/or metal ion used in the synthesis of the the metal organic frameworks can be coordinated with atoms, groups of atoms, or ligands so that the coordination complex or cluster has a molecular geometry including, but not limited to, trigonal planar, tetrahedral, square planar, trigonal bipyramidal, square pyramidal, octahedral, trigonal prismatic, pentagonal bipyramidal, paddle-wheel and square antiprismatic. In a further embodiment, the metal ion used in the synthesis of the metal organic frameworks can form a coordination complex or cluster that has a molecular geometry including, but not limited to, tetrahedral, paddle-wheel and octahedral molecular geometry. In a further embodiment, the metal and/or metal ion used in the synthesis of the metal organic framework can form a coordination complex or cluster that has octahedral molecular geometry. In another embodiment, the coordination complex with octahedral geometry can exist as various isomers depending on whether two or more types of ligands are coordinated to a metal ion. Examples of such isomers that can result, include, but are not limited to, cis, trans, fac, mer, and any combination thereof for coordination complexes that have three or more different ligands. In a yet further embodiment, the coordination complex or cluster disclosed herein may have chirality. In another embodiment, the coordination complex or cluster disclosed herein may not have chirality.

In one embodiment, the linking moiety comprises an organic-based parent chain comprising alkyl, hetero-alkyl, alkenyl, hetero-alkenyl, alkynyl, hetero-alkynyl, one or more cycloalkyl rings, one or more cycloalkenyl rings, one or more cycloalkynyl rings, one of more aryl rings, one or more heterocycle rings, or any combination of the preceding groups, including larger ring structures composed of linked and/or fused ring systems of different types of rings; wherein this organic-based parent chain may be further substituted with one or more functional groups, including additional substituted or unsubstituted hydrocarbons and heterocycle groups, or a combination thereof; and wherein the linking moiety contains at least one (e.g., 1, 2, 3, 4, 5, 6, . . . ) linking cluster.

In a yet further embodiment, the linking moiety of the metal organic framework has an organic-based parent chain that is comprised of one or more substituted or unsubstituted rings; wherein one or more of these rings is further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster.

In a yet further embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster that is either a carboxylic acid, amine, thiol, cyano, nitro, hydroxyl, or heterocycle ring heteroatom, such as the N in pyridine.

In another embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) linking cluster that is either a carboxylic acid, amine, hydroxyl, or heterocycle ring heteroatom, such as the N in pyridine.

In another embodiment, the linking moiety of the metal organic framework has an organic-based parent chain that is comprised of one or more substituted or unsubstituted rings; wherein one or more of these rings are further substituted with one or more functional groups, including additional substituted or unsubstituted hydrocarbons and heterocycle groups, or a combination thereof; and wherein the linking moiety contains at least one (e.g. 1, 2, 3, 4, 5, 6, . . . ) carboxylic acid linking cluster.

In another embodiment, the linking moiety of the metal organic framework has an organic-based parent chain that is comprised of one or more substituted or unsubstituted rings; wherein one or more of these rings are further substituted with two or more functional groups, including additional substituted or unsubstituted hydrocarbon and heterocycle groups, or a combination thereof; and wherein the linking moiety contains at least two (e.g. 2, 3, 4, 5, 6, . . . ) carboxylic acid linking clusters.

In certain embodiments, the metal organic framework is generated from one or more linking moieties that have a structure of Formula I, II, III, IV, V, VI, VII, VIII, IX, and X:

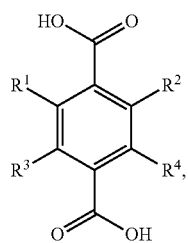
(I)

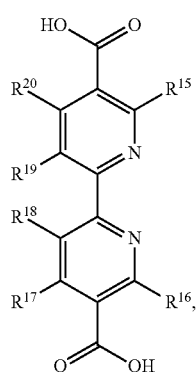
(II)

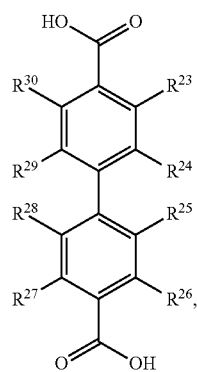
(III)

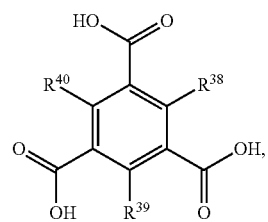
(IV)

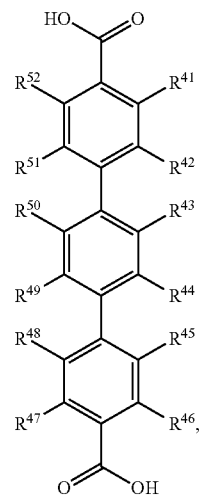
(V)

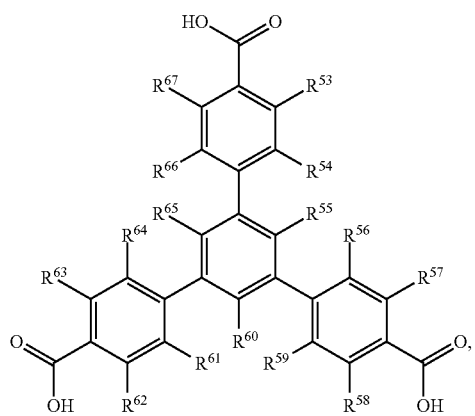
(VI)

-continued

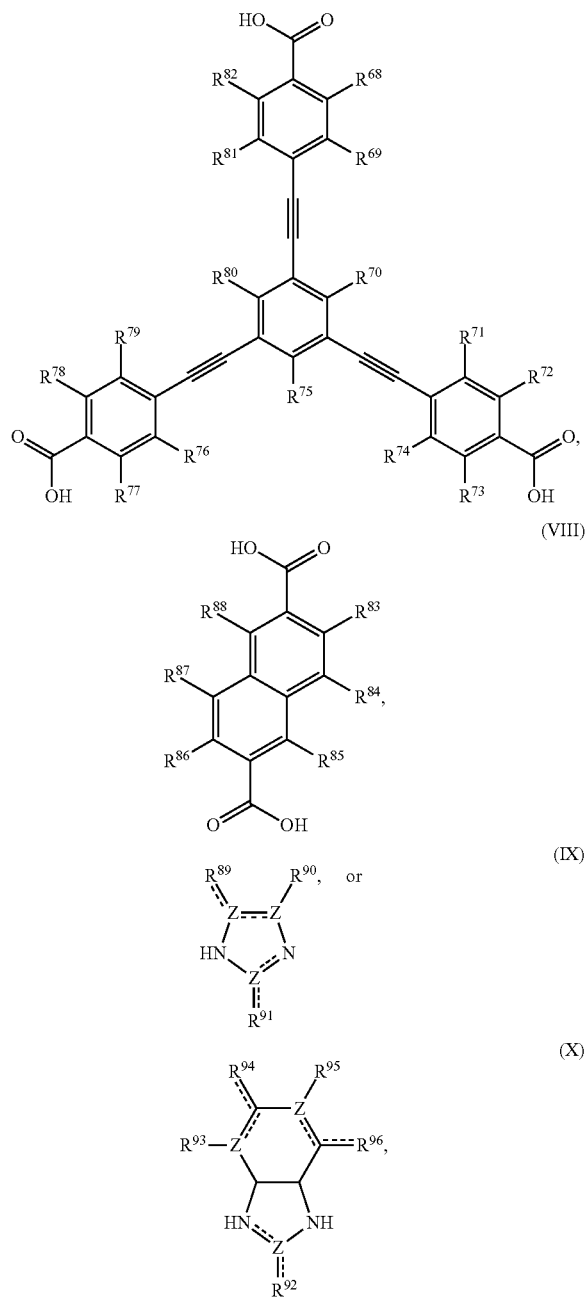

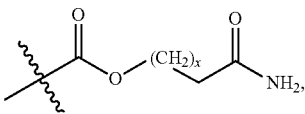

wherein:

$R^1$-$R^4$, $R^{15}$-$R^{20}$, $R^{23}$-$R^{30}$, $R^{38}$-$R^{96}$ are independently selected from the group comprising H, FG, $(C_1$-$C_{20})$alkyl, substituted $(C_1$-$C_{20})$alkyl, $(C_1$-$C_{20})$alkenyl, substituted $(C_1$-$C_{20})$alkenyl, $(C_1$-$C_{20})$alkynyl, substituted $(C_1$-$C_{20})$alkynyl, hetero-$(C_1$-$C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, $(C_1$-$C_{20})$cycloalkyl, substituted $(C_1$-$C_{20})$cycloalkyl, aryl, substituted aryl, heterocycle, substituted heterocycle, —C($R^5$)$_3$, —CH($R^5$)$_2$, —CH$_2$$R^5$, —C($R^6$)$_3$, —CH($R^6$)$_2$, —CH$_2$$R^6$, —OC($R^5$)$_3$, —OCH($R^5$)$_2$, —OCH$_2$$R^5$, —OC($R^6$)$_3$, —OCH($R^6$)$_2$, —OCH$_2$$R^6$, wherein $R^1$ and $R^3$ are linked together to form a substituted or unsubstituted ring selected from the group comprising cycloalkyl, aryl and heterocycle, wherein $R^2$ and $R^4$ are linked together to form a substituted or unsubstituted ring selected from the group comprising cycloalkyl, aryl and heterocycle, wherein $R^{18}$ and $R^{19}$ are linked together to form a substituted or unsubstituted ring selected from the group comprising cycloalkyl, aryl and heterocycle, wherein $R^{24}$ and $R^{25}$ are linked together to form a substituted or unsubstituted ring selected from the group comprising cycloalkyl, aryl and heterocycle, and wherein $R^{28}$ and $R^{29}$ are linked together to form a substituted or unsubstituted ring selected from the group comprising cycloalkyl, aryl and heterocycle;

$R^5$ is selected from the group comprising FG, $(C_1$-$C_{20})$alkyl, $(C_1$-$C_{20})$substituted alkyl, $((C_1$-$C_{20})$alkenyl, substituted $(C_1$-$C_{20})$alkenyl, $(C_1$-$C_{20})$alkynyl, substituted $(C_1$-$C_{20})$alkynyl, hetero-$(C_1$-$C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, hemiacetal, hemiketal, acetal, ketal, and orthoester;

$R_6$ is one or more substituted or unsubstituted rings selected from the group comprising cycloalkyl, aryl, and heterocycle; and X is a number from 0 to 10.

In another embodiment, the metal organic framework is generated from linking moieties that have at least two structures selected from Formula I, II, III, IV, V, VI, VII, VIII, IX, and X.

In a further embodiment, the metal organic framework is generated from a linking moiety that has the structure of Formula I, II, III, IV, V, VI, VII, and VIII. In yet a further embodiment, the metal organic framework is generated from linking moieties that have at least two structures selected from Formula I, II, III, IV, V, VI, VII, and VIII.

In another embodiment, the metal organic framework is generated from a linking moiety that has a structure of Formula IX or X. In another embodiment, the metal organic framework is generated from linking moieties that have structures of Formula IX and X.

In a further embodiment, the metal organic framework is generated from a linking moiety comprising Formula I, II, III, IV, V, VI, VII, VIII, IX, and X:

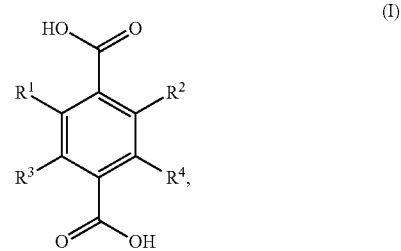

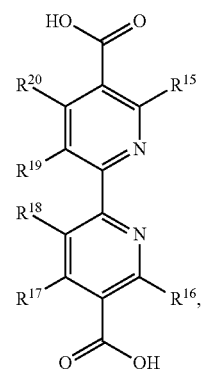 (II)
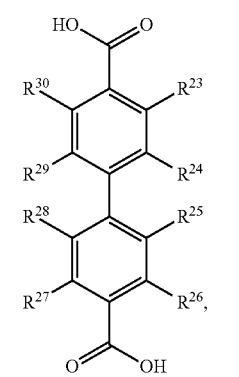 (III)
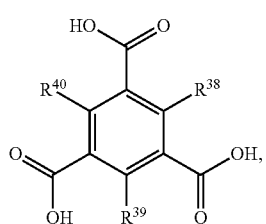 (IV)
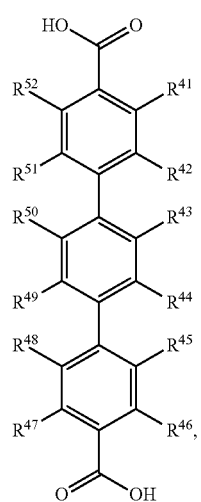 (V)
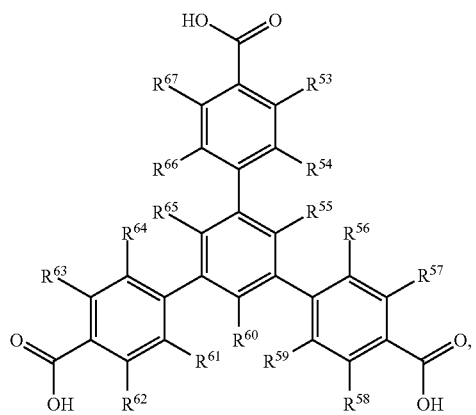 (VI)
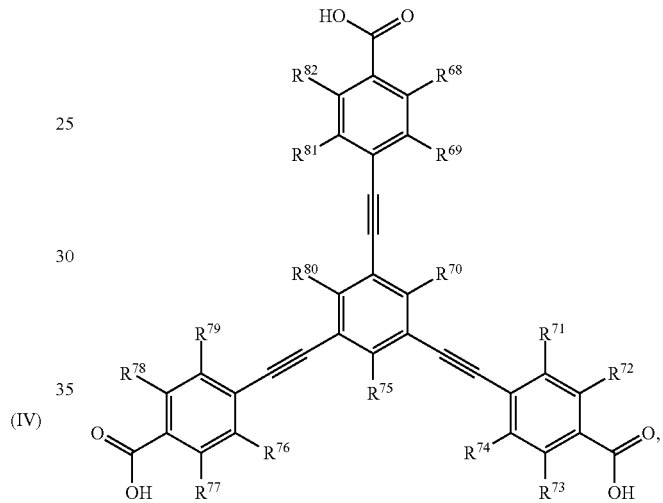 (VII)
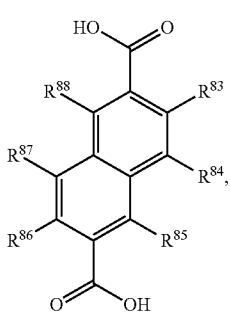 (VIII)
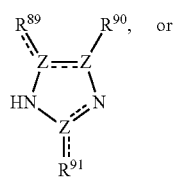 (IX)
or -continued

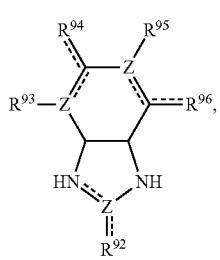

(X)

wherein:

R$^1$-R$^4$, R$^{15}$-R$^{20}$, R$^{23}$-R$^{30}$, R$^{38}$-R$^{96}$ are independently selected from the group comprising H, FG, (C$_1$-C$_6$)alkyl, substituted (C$_1$-C$_6$)alkyl, (C$_1$-C$_6$)alkenyl, substituted (C$_1$-C$_6$)alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, (C$_1$-C$_6$)cycloalkyl, substituted (C$_1$-C$_6$)cycloalkyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$,

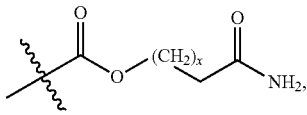

wherein R$^1$ and R$^3$ are linked together to form a substituted or unsubstituted ring selected from the group comprising cycloalkyl, aryl and heterocycle, wherein R$^2$ and R$^4$ are linked together to form a substituted or unsubstituted ring selected from the group comprising cycloalkyl, aryl and heterocycle, wherein R$^{18}$ and R$^{19}$ are linked together to form a substituted or unsubstituted ring selected from the group comprising cycloalkyl, aryl and heterocycle, wherein R$^{24}$ and R$^{25}$ are linked together to form a substituted or unsubstituted ring selected from the group comprising cycloalkyl, aryl and heterocycle, and wherein R$^{28}$ and R$^{29}$ are linked together to form a substituted or unsubstituted ring selected from the group comprising cycloalkyl, aryl and heterocycle;

R$^5$ is selected from the group comprising FG, (C$_1$-C$_6$)alkyl, (C$_1$-C$_6$)substituted alkyl, ((C$_1$-C$_6$)alkenyl, substituted (C$_1$-C$_6$)alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, hemiacetal, hemiketal, acetal, ketal, and orthoester;

R$_6$ is one or more substituted or unsubstituted rings selected from the group comprising cycloalkyl, aryl, and heterocycle; and X is a number from 0 to 3.

In a certain embodiment, the metal organic framework is generated from a linking moiety comprising structural Formula I:

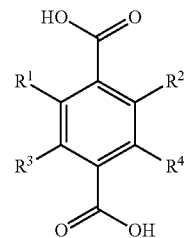

(I)

wherein:

R$^1$-R$^4$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$

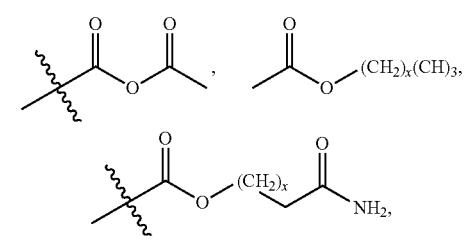

wherein R$^1$ and R$^3$ are linked together to form a substituted or unsubstituted ring selected from the group comprising cycloalkyl, aryl and heterocycle, and wherein R$^2$ and R$^4$ are linked together to form a substituted or unsubstituted ring selected from the group comprising cycloalkyl, aryl and heterocycle;

R$^5$ is selected from the group comprising hydroxyl, amine, thiol, cyano, carboxyl, (C$_1$-C$_6$)alkyl, (C$_1$-C$_6$)substituted alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, hemiacetal, hemiketal, acetal, ketal, and orthoester;

R$_6$ is one or more substituted or unsubstituted rings selected from the group comprising cycloalkyl, aryl, and heterocycle; and X is a number from 0 to 3.

In another embodiment, the metal organic framework is generated from a linking moiety selected from the group comprising:

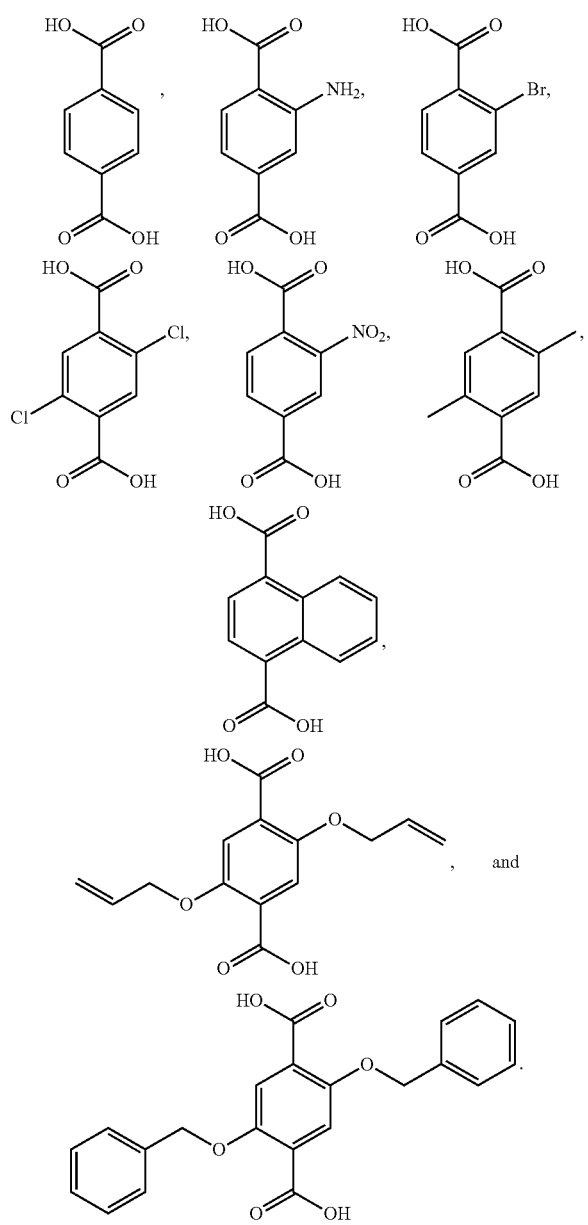

In yet another embodiment, the metal organic framework is generated from a linking moiety selected from the group comprising:

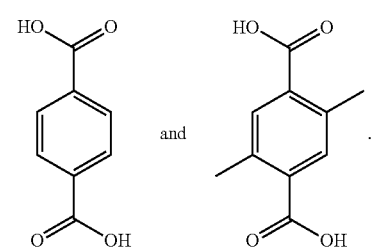

In yet another embodiment, the metal organic framework is generated from a linking moiety of:

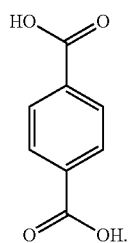

In yet another embodiment, the metal organic framework is generated from a linking moiety of:

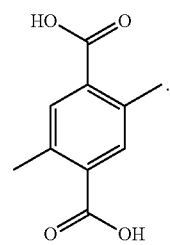

In a further embodiment, the linking moiety of structural Formula I wherein $R^2$ and $R^4$ are linked together to form a unsubstituted or substituted aryl comprising structural Formula I(a):

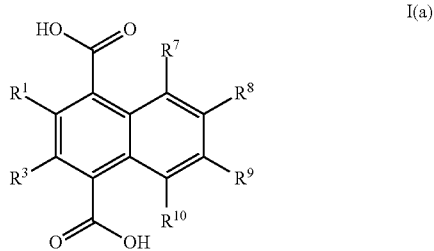

I(a)

wherein:

$R^1$, $R^3$, $R^7$-$R^{10}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$.

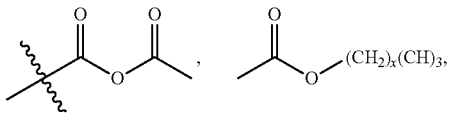

-continued

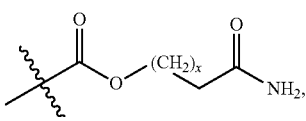

and wherein $R^1$ and $R^3$ are linked together to form a substituted or unsubstituted ring selected from the group comprising cycloalkyl, aryl and heterocycle;

$R^5$ is selected from the group comprising hydroxyl, amine, thiol, cyano, carboxyl, ($C_1$-$C_6$)alkyl, ($C_1$-$C_6$)substituted alkyl, ($C_1$-$C_6$)alkenyl, substituted ($C_2$-$C_6$)alkenyl, ($C_2$-$C_6$) alkynyl, substituted ($C_2$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_2$-$C_6$)alkenyl, hetero-($C_2$-$C_6$)alkynyl, substituted hetero-($C_2$-$C_6$)alkynyl, hemiacetal, hemiketal, acetal, ketal, and orthoester;

$R_6$ is one or more substituted or unsubstituted rings selected from the group comprising cycloalkyl, aryl, and heterocycle; and X is a number from 0 to 3.

In a yet further embodiment, the linking moiety of structural Formula I wherein $R^2$ and $R^4$ are linked together to form a unsubstituted or substituted aryl and wherein $R^1$ and $R^3$ are linked together to form a unsubstituted or substituted aryl, comprising structural Formula I(b):

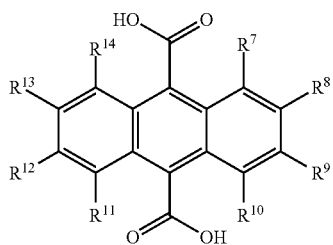

I(b)

wherein:

$R^7$-$R^{14}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, ($C_1$-$C_6$)alkyl, substituted ($C_1$-$C_6$)alkyl, ($C_1$-$C_6$)alkenyl, substituted ($C_2$-$C_6$)alkenyl, ($C_2$-$C_6$)alkynyl, substituted ($C_2$-$C_6$) alkynyl, hetero-($C_1$-$C_6$)alkyl, substituted hetero-($C_1$-$C_6$) alkyl, hetero-($C_1$-$C_6$)alkenyl, substituted hetero-($C_2$-$C_6$) alkenyl, hetero-($C_2$-$C_6$)alkynyl, substituted hetero-($C_2$-$C_6$) alkynyl, aryl, substituted aryl, heterocycle, substituted heterocycle, —C($R^5$)$_3$, —CH($R^5$)$_2$, —CH$_2R^5$, —C($R^6$)$_3$, —CH($R^6$)$_2$, —CH$_2R^6$, —OC($R^5$)$_3$, —OCH($R^5$)$_2$, —OCH$_2R^5$, —OC($R^6$)$_3$, —OCH($R^6$)$_2$, —OCH$_2R^6$,

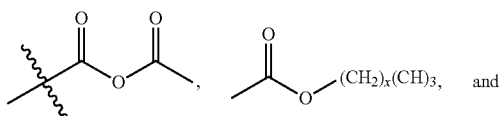 and

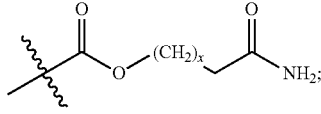

$R^5$ is selected from the group comprising hydroxyl, amine, thiol, cyano, carboxyl, ($C_1$-$C_6$)alkyl, ($C_1$-$C_6$)substituted alkyl, ($C_1$-$C_6$)alkenyl, substituted ($C_2$-$C_6$)alkenyl, ($C_2$-$C_6$) alkynyl, substituted ($C_2$-$C_6$)alkynyl, hetero-($C_1$-$C_6$)alkyl, substituted hetero-($C_1$-$C_6$)alkyl, hetero-($C_1$-$C_6$)alkenyl, substituted hetero-($C_2$-$C_6$)alkenyl, hetero-($C_2$-$C_6$)alkynyl, substituted hetero-($C_2$-$C_6$)alkynyl, hemiacetal, hemiketal, acetal, ketal, and orthoester;

$R_6$ is one or more substituted or unsubstituted rings selected from the group comprising cycloalkyl, aryl, and heterocycle; and X is a number from 0 to 3.

In one embodiment, the metal organic framework is generated from a linking moiety of Formula II:

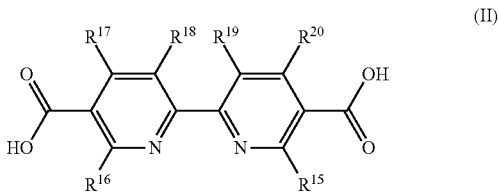

(II)

wherein:

$R^{15}$-$R^{20}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, ($C_1$-$C_6$)alkyl, substituted ($C_1$-$C_6$)alkyl, ($C_1$-$C_6$)alkenyl, substituted ($C_2$-$C_6$)alkenyl, ($C_2$-$C_6$)alkynyl, substituted ($C_2$-$C_6$) alkynyl, hetero-($C_1$-$C_6$)alkyl, substituted hetero-($C_1$-$C_6$) alkyl, hetero-($C_1$-$C_6$)alkenyl, substituted hetero-($C_2$-$C_6$) alkenyl, hetero-($C_2$-$C_6$)alkynyl, substituted hetero-($C_2$-$C_6$) alkynyl, aryl, substituted aryl, heterocycle, substituted heterocycle, —C($R^5$)$_3$, —CH($R^5$)$_2$, —CH$_2R^5$, —C($R^6$)$_3$, —CH($R^6$)$_2$, —CH$_2R^6$, —OC($R^5$)$_3$, —OCH($R^5$)$_2$, —OCH$_2R^5$, —OC($R^6$)$_3$, —OCH($R^6$)$_2$, —OCH$_2R^6$,

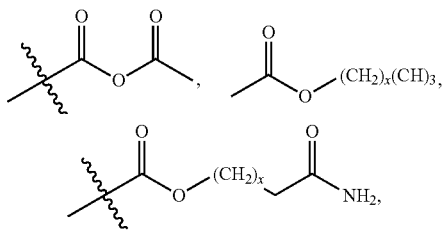

and wherein $R^{18}$ and $R^{19}$ are linked together to form a substituted or unsubstituted ring selected from the group comprising cycloalkyl, aryl and heterocycle;

$R^5$ is selected from the group comprising hydroxyl, amine, thiol, cyano, carboxyl, ($C_1$-$C_6$)alkyl, ($C_1$-$C_6$)substituted alkyl, ($C_1$-$C_6$)alkenyl, substituted ($C_2$-$C_6$)alkenyl, ($C_2$-$C_6$) alkynyl, substituted ($C_2$-$C_6$)alkynyl, hetero-($C_1$-$C_6$)alkyl, substituted hetero-($C_1$-$C_6$)alkyl, hetero-($C_1$-$C_6$)alkenyl, substituted hetero-$(C_2\text{-}C_6)$alkenyl, hetero-$(C_2\text{-}C_6)$alkynyl, substituted hetero-$(C_2\text{-}C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In an another embodiment, the linking moiety of structural Formula II wherein $R^{18}$ and $R^{19}$ are linked together to form a unsubstituted or substituted aryl comprising structural Formula II(a):

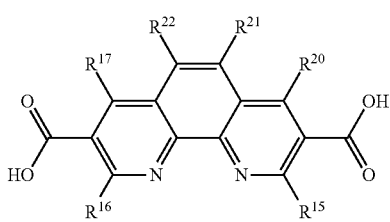

wherein:

$R^{15}$-$R^{17}$, $R^{20}$-$R^{22}$ are independently selected from the group H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1\text{-}C_6)$alkyl, substituted $(C_1\text{-}C_6)$alkyl, $(C_1\text{-}C_6)$alkenyl, substituted $(C_2\text{-}C_6)$alkenyl, $(C_2\text{-}C_6)$alkynyl, substituted $(C_2\text{-}C_6)$alkynyl, hetero-$(C_1\text{-}C_6)$alkyl, substituted hetero-$(C_1\text{-}C_6)$alkyl, hetero-$(C_1\text{-}C_6)$alkenyl, substituted hetero-$(C_2\text{-}C_6)$alkenyl, hetero-$(C_2\text{-}C_6)$alkynyl, substituted hetero-$(C_2\text{-}C_6)$alkynyl, aryl, substituted aryl, heterocycle, substituted heterocycle, $-C(R^5)_3$, $-CH(R^5)_2$, $-CH_2R^5$, $-C(R^6)_3$, $-CH(R^6)_2$, $-CH_2R^6$, $-OC(R^5)_3$, $-OCH(R^5)_2$, $-OCH_2R^5$, $-OC(R^6)_3$, $-OCH(R^6)_2$, $-OCH_2R^6$,

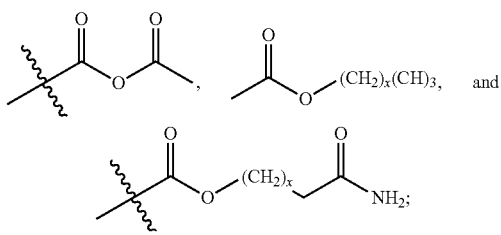

$R^5$ is selected from the group comprising hydroxyl, amine, thiol, cyano, carboxyl, $(C_1\text{-}C_6)$alkyl, $(C_1\text{-}C_6)$substituted alkyl, $(C_1\text{-}C_6)$alkenyl, substituted $(C_2\text{-}C_6)$alkenyl, $(C_2\text{-}C_6)$alkynyl, substituted $(C_2\text{-}C_6)$alkynyl, hetero-$(C_1\text{-}C_6)$alkyl, substituted hetero-$(C_1\text{-}C_6)$alkyl, hetero-$(C_1\text{-}C_6)$alkenyl, substituted hetero-$(C_2\text{-}C_6)$alkenyl, hetero-$(C_2\text{-}C_6)$alkynyl, substituted hetero-$(C_2\text{-}C_6)$alkynyl, hemiacetal, hemiketal, acetal, ketal, and orthoester;

$R_6$ is one or more substituted or unsubstituted rings selected from the group comprising cycloalkyl, aryl, and heterocycle; and X is a number from 0 to 3.

In an another embodiment, the metal organic framework is generated from a linking moiety of Formula III:

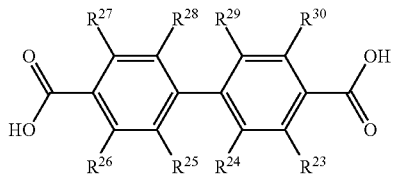

wherein:

$R^{23}$-$R^{30}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1\text{-}C_6)$alkyl, substituted $(C_1\text{-}C_6)$alkyl, $(C_1\text{-}C_6)$alkenyl, substituted $(C_2\text{-}C_6)$alkenyl, $(C_2\text{-}C_6)$alkynyl, substituted $(C_2\text{-}C_6)$alkynyl, hetero-$(C_1\text{-}C_6)$alkyl, substituted hetero-$(C_1\text{-}C_6)$alkyl, hetero-$(C_1\text{-}C_6)$alkenyl, substituted hetero-$(C_2\text{-}C_6)$alkenyl, hetero-$(C_2\text{-}C_6)$alkynyl, substituted hetero-$(C_2\text{-}C_6)$alkynyl, aryl, substituted aryl, heterocycle, substituted heterocycle, $-C(R^5)_3$, $-CH(R^5)_2$, $-CH_2R^5$, $-C(R^6)_3$, $-CH(R^6)_2$, $-CH_2R^6$, $-OC(R^5)_3$, $-OCH(R^5)_2$, $-OCH_2R^5$, $-OC(R^6)_3$, $-OCH(R^6)_2$, $-OCH_2R^6$,

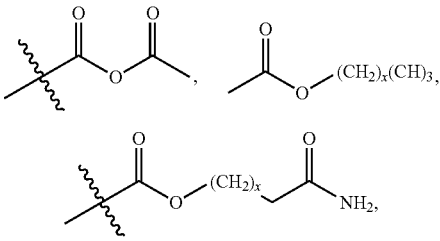

wherein $R^{24}$ and $R^{25}$ are linked together to form a substituted or unsubstituted ring selected from the group comprising cycloalkyl, aryl and heterocycle, and wherein $R^{28}$ and $R^{29}$ are linked together to form a substituted or unsubstituted ring selected from the group comprising cycloalkyl, aryl and heterocycle;

$R^5$ is selected from the group comprising hydroxyl, amine, thiol, cyano, carboxyl, $(C_1\text{-}C_6)$alkyl, $(C_1\text{-}C_6)$substituted alkyl, $(C_1\text{-}C_6)$alkenyl, substituted $(C_2\text{-}C_6)$alkenyl, $(C_2\text{-}C_6)$alkynyl, substituted $(C_2\text{-}C_6)$alkynyl, hetero-$(C_1\text{-}C_6)$alkyl, substituted hetero-$(C_1\text{-}C_6)$alkyl, hetero-$(C_1\text{-}C_6)$alkenyl, substituted hetero-$(C_2\text{-}C_6)$alkenyl, hetero-$(C_2\text{-}C_6)$alkynyl, substituted hetero-$(C_2\text{-}C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In a further embodiment, the linking moiety of structural Formula III wherein $R^{24}$ and $R^{25}$ are linked together to form a unsubstituted or substituted aryl, and wherein $R^{28}$ and $R^{29}$ are linked together to form a unsubstituted or substituted aryl to comprise structural Formula III(a):

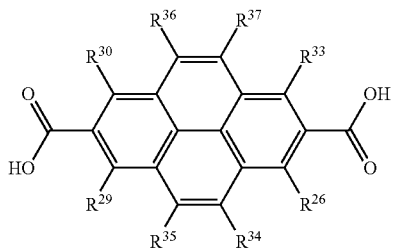

(III(a))

wherein:

$R^{26}$, $R^{29}$, $R^{30}$, $R^{33}$, $R^{34}$-$R^{37}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$,

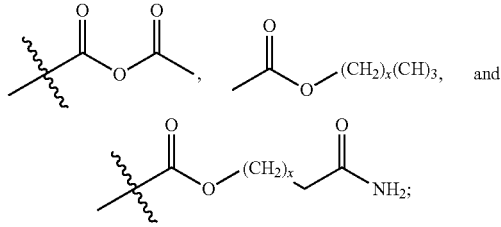

$R^5$ is selected from the group comprising hydroxyl, amine, thiol, cyano, carboxyl, (C$_1$-C$_6$)alkyl, (C$_1$-C$_6$)substituted alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In a yet further embodiment, the metal organic framework is generated from a linking moiety of Formula IV:

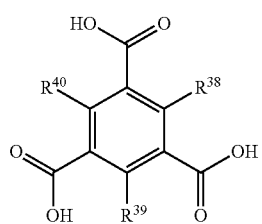

(IV)

wherein:

$R^{38}$-$R^{40}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$,

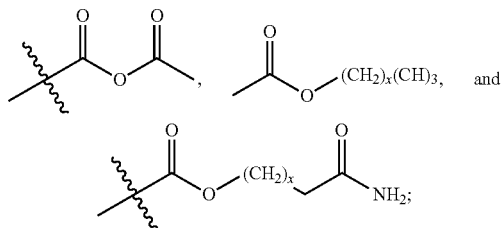

$R^5$ is selected from the group comprising hydroxyl, amine, thiol, cyano, carboxyl, (C$_1$-C$_6$)alkyl, (C$_1$-C$_6$)substituted alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In a certain embodiment, the metal organic framework is generated from a linking moiety of Formula V:

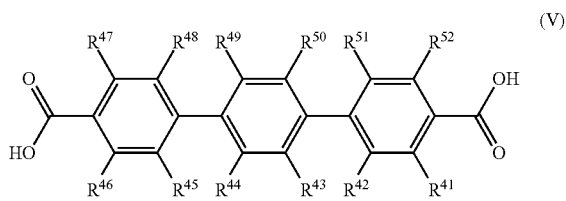

(V)

wherein:

$R^{41}$-$R^{52}$ are independently selected from the group comprising H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$

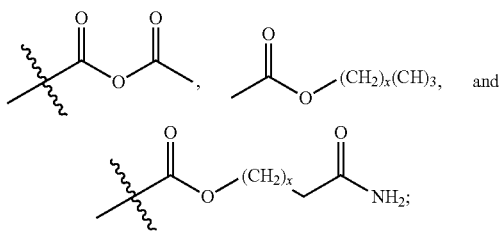

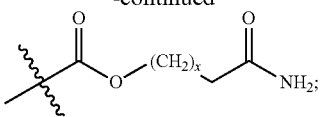

$R^5$ is selected from the group comprising hydroxyl, amine, thiol, cyano, carboxyl, $(C_1$-$C_6)$alkyl, $(C_1$-$C_6)$substituted alkyl, $(C_1$-$C_6)$alkenyl, substituted $(C_2$-$C_6)$alkenyl, $(C_2$-$C_6)$alkynyl, substituted $(C_2$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_2$-$C_6)$alkenyl, hetero-$(C_2$-$C_6)$alkynyl, substituted hetero-$(C_2$-$C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In an another embodiment, the metal organic framework is generated from a linking moiety of Formula VI:

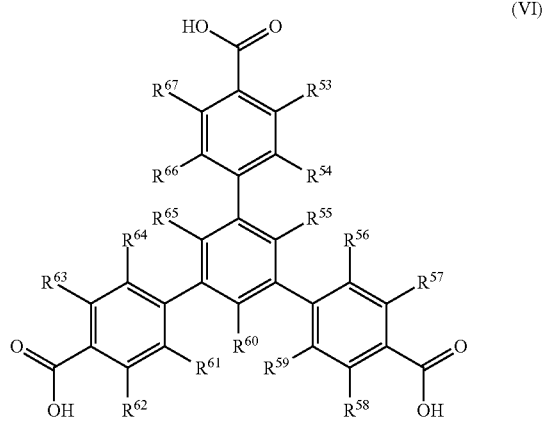

(VI)

wherein:

$R^{53}$-$R^{67}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1$-$C_6)$alkyl, substituted $(C_1$-$C_6)$alkyl, $(C_1$-$C_6)$alkenyl, substituted $(C_2$-$C_6)$alkenyl, $(C_2$-$C_6)$alkynyl, substituted $(C_2$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_2$-$C_6)$alkenyl, hetero-$(C_2$-$C_6)$alkynyl, substituted hetero-$(C_2$-$C_6)$alkynyl, aryl, substituted aryl, heterocycle, substituted heterocycle, —$C(R^5)_3$, —$CH(R^5)_2$, —$CH_2R^5$, —$C(R^6)_3$, —$CH(R^6)_2$, —$CH_2R^6$, —$OC(R^5)_3$, —$OCH(R^5)_2$, —$OCH_2R^5$, —$OC(R^6)_3$, —$OCH(R^6)_2$, —$OCH_2R^6$,

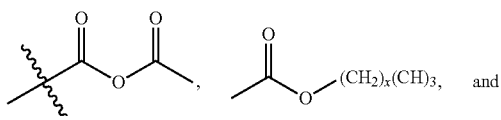

$R^5$ is selected from the group comprising hydroxyl, amine, thiol, cyano, carboxyl, $(C_1$-$C_6)$alkyl, $(C_1$-$C_6)$substituted alkyl, $(C_1$-$C_6)$alkenyl, substituted $(C_2$-$C_6)$alkenyl, $(C_2$-$C_6)$alkynyl, substituted $(C_2$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_2$-$C_6)$alkenyl, hetero-$(C_2$-$C_6)$alkynyl, substituted hetero-$(C_2$-$C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In an another embodiment, the metal organic framework is generated from a linking moiety of Formula VII:

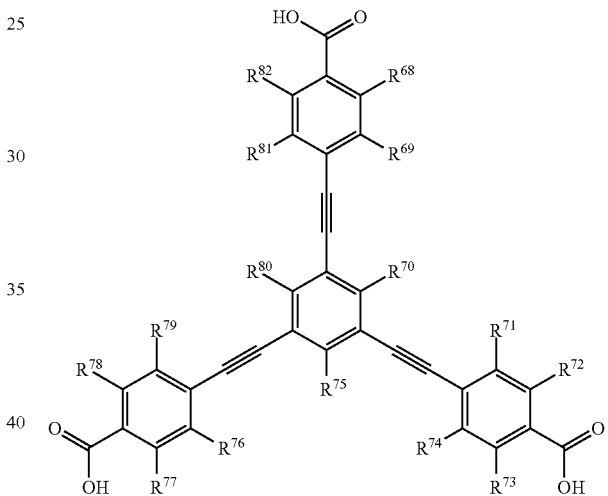

(VII)

wherein:

$R^{68}$-$R^{82}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1$-$C_6)$alkyl, substituted $(C_1$-$C_6)$alkyl, $(C_1$-$C_6)$alkenyl, substituted $(C_2$-$C_6)$alkenyl, $(C_2$-$C_6)$alkynyl, substituted $(C_2$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_2$-$C_6)$alkenyl, hetero-$(C_2$-$C_6)$alkynyl, substituted hetero-$(C_2$-$C_6)$alkynyl, aryl, substituted aryl, heterocycle, substituted heterocycle, —$C(R^5)_3$, —$CH(R^5)_2$, —$CH_2R^5$, —$C(R^6)_3$, —$CH(R^6)_2$, —$CH_2R^6$, —$OC(R^5)_3$, —$OCH(R^5)_2$, —$OCH_2R^5$, —$OC(R^6)_3$, —$OCH(R^6)_2$, —$OCH_2R^6$,

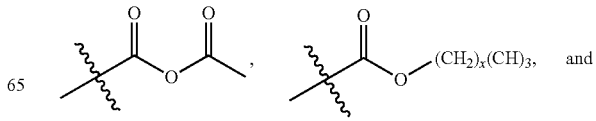

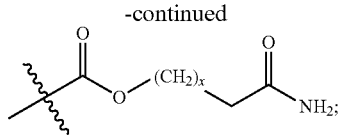

$R^5$ is selected from the group comprising hydroxyl, amine, thiol, cyano, carboxyl, $(C_1-C_6)$alkyl, $(C_1-C_6)$substituted alkyl, $(C_1-C_6)$alkenyl, substituted $(C_2-C_6)$alkenyl, $(C_2-C_6)$ alkynyl, substituted $(C_2-C_6)$alkynyl, hetero-$(C_1-C_6)$alkyl, substituted hetero-$(C_1-C_6)$alkyl, hetero-$(C_1-C_6)$alkenyl, substituted hetero-$(C_2-C_6)$alkenyl, hetero-$(C_2-C_6)$alkynyl, substituted hetero-$(C_2-C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In an another embodiment, the metal organic framework is generated from a linking moiety of Formula III:

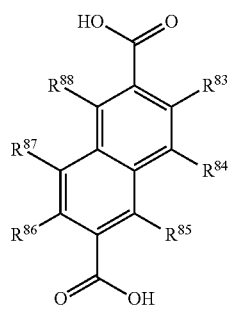

(VIII)

wherein:

$R^{83}$-$R^{88}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1-C_6)$alkyl, substituted $(C_1-C_6)$alkyl, $(C_1-C_6)$alkenyl, substituted $(C_2-C_6)$alkenyl, $(C_2-C_6)$alkynyl, substituted $(C_2-C_6)$ alkynyl, hetero-$(C_1-C_6)$alkyl, substituted hetero-$(C_1-C_6)$ alkyl, hetero-$(C_1-C_6)$alkenyl, substituted hetero-$(C_2-C_6)$ alkenyl, hetero-$(C_2-C_6)$alkynyl, substituted hetero-$(C_2-C_6)$ alkynyl, aryl, substituted aryl, heterocycle, substituted heterocycle, —$C(R^5)_3$, —$CH(R^5)_2$, —$CH_2R^5$, —$C(R^6)_3$, —$CH(R^6)_2$, —$CH_2R^6$, —$OC(R^5)_3$, $OCH(R^5)_2$, —$OCH_2R^5$, —$OC(R^6)_3$, —$OCH(R^6)_2$, —$OCH_2R^6$,

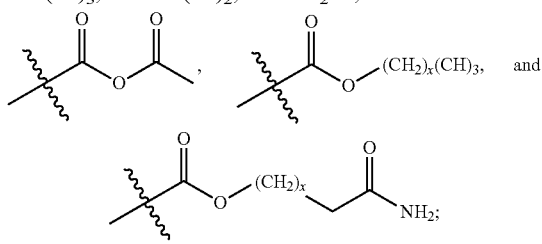

$R^5$ is selected from the group comprising hydroxyl, amine, thiol, cyano, carboxyl, $(C_1-C_6)$alkyl, $(C_1-C_6)$substituted alkyl, $(C_1-C_6)$alkenyl, substituted $(C_2-C_6)$alkenyl, $(C_2-C_6)$ alkynyl, substituted $(C_2-C_6)$alkynyl, hetero-$(C_1-C_6)$alkyl, substituted hetero-$(C_1-C_6)$alkyl, hetero-$(C_1-C_6)$alkenyl, substituted hetero-$(C_2-C_6)$alkenyl, hetero-$(C_2-C_6)$alkynyl, substituted hetero-$(C_2-C_6)$alkynyl, hemiacetal, hemiketal, acetal, ketal, and orthoester;

$R_6$ is a substituted or unsubstituted ring selected from the group comprising cycloalkyl, aryl, and heterocycle; and X is a number from 0 to 3.

In another embodiment, the metal organic framework is generated from a linking moiety of Formula IX:

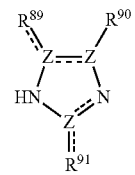

(IX)

wherein:

Z is either a C or N;

$R^{89}$-$R^{91}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1-C_6)$alkyl, substituted $(C_1-C_6)$alkyl, $(C_1-C_6)$alkenyl, substituted $(C_1-C_6)$alkenyl, $(C_1-C_6)$alkynyl, substituted $(C_1-C_6)$ alkynyl, hetero-$(C_1-C_6)$alkyl, substituted hetero-$(C_1-C_6)$ alkyl, hetero-$(C_1-C_6)$ alkenyl, substituted hetero-$(C_1-C_6)$ alkenyl, hetero-$(C_1-C_6)$alkynyl, substituted hetero-$(C_1-C_6)$ alkynyl, aryl, substituted aryl, heterocycle, substituted heterocycle, and are absent when Z is an N.

In yet another embodiment, the linking moiety of Formula IX is selected from the group comprising:

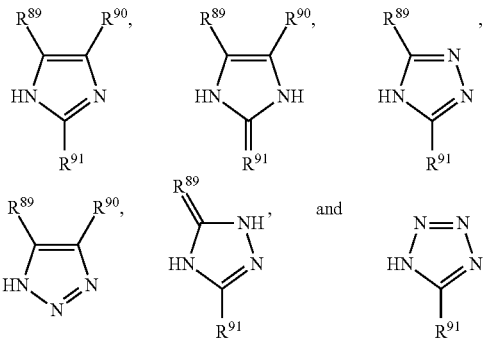

In another embodiment, the metal organic framework is generated from a linking moiety of Formula X:

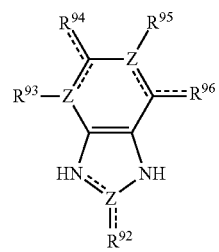

(X)

wherein:

Z is either a C or N;

$R^{92}$-$R^{96}$ are independently selected from the group comprising H, halo, amine, cyano, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $(C_1-C_6)$alkyl, substituted $(C_1-C_6)$alkyl, $(C_1-C_6)$alkenyl, substituted $(C_1-C_6)$alkenyl, $(C_1-C_6)$alkynyl, substituted $(C_1-C_6)$ alkynyl, hetero-($C_1$-$C_6$)alkyl, substituted hetero-($C_1$-$C_6$) alkyl, hetero-($C_1$-$C_6$) alkenyl, substituted hetero-($C_1$-$C_6$) alkenyl, hetero-($C_1$-$C_6$)alkynyl, substituted hetero-($C_1$-$C_6$) alkynyl, aryl, substituted aryl, heterocycle, substituted heterocycle, and are absent when Z is an N.

In yet another embodiment, the linking moiety of Formula X is selected from the group comprising:

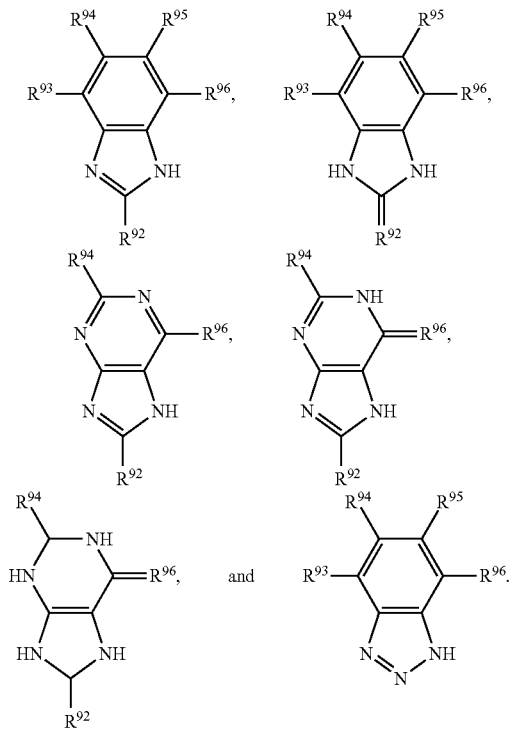

The preparation of the frameworks of the disclosure can be carried out in either an aqueous or non-aqueous solvent system. The solvent may be polar or non-polar, or a combination thereof, as the case may be. The reaction mixture or suspension comprises a solvent system, linking moiety or moieties, and a metal or a metal/salt complex. The reaction solution, mixture or suspension may further contain a templating agent, catalyst, or combination thereof. The reaction mixture may be heated at an elevated temperature or maintained at ambient temperature, depending on the reaction components.

Examples of non-aqueous solvents that can be used in the reaction to make the framework and/or used as non-aqueous solvent for a post synthesized framework reaction, include, but is not limited to: n-hydrocarbon based solvents, such as pentane, hexane, octadecane, and dodecane; branched and cyclo-hydrocarbon based solvents, such as cycloheptane, cyclohexane, methyl cyclohexane, cyclohexene, cyclopentane; aryl and substituted aryl based solvents, such as benzene, toluene, xylene, chlorobenzene, nitrobenzene, cyanobenzene, naphthalene, and aniline; mixed hydrocarbon and aryl based solvents, such as, mixed hexanes, mixed pentanes, naptha, and petroleum ether; alcohol based solvents, such as, methanol, ethanol, n-propanol, isopropanol, propylene glycol, 1,3-propanediol, n-butanol, isobutanol, 2-methyl-1-butanol, tert-butanol, 1,4-butanediol, 2-methyl-1-petanol, and 2-pentanol; amide based solvents, such as, dimethylacetamide, dimethylformamide (DMF), formamide, N-methylformamide, N-methylpyrrolidone, and 2-pyrrolidone; amine based solvents, such as, piperidine, pyrrolidine, collidine, pyridine, morpholine, quinoline, ethanolamine, ethylenediamine, and diethylenetriamine; ester based solvents, such as, butylacetate, sec-butyl acetate, tert-butyl acetate, diethyl carbonate, ethyl acetate, ethyl acetoacetate, ethyl lactate, ethylene carbonate, hexyl acetate, isobutyl acetate, isopropyl acetate, methyl acetate, propyl acetate, and propylene carbonate; ether based solvents, such as, di-tert-butyl ether, diethyl ether, diglyme, diisopropyl ether, 1,4-dioxane, 2-methyltetrahydrofuran, tetrahydrofuran (THF), and tetrahydropyran; glycol ether based solvents, such as, 2-butoxyethanol, dimethoxyethane, 2-ethoxyethanol, 2-(2-ethoxyethoxy)ethanol, and 2-methoxyethanol; halogenated based solvents, such as, carbon tetrachloride, cholorbenzene, chloroform, 1,1-dichloroethane, 1,2-dichloroethane, 1,2-dichloroethene, dichloromethane (DCM), diiodomethane, epichlorohydrin, hexachlorobutadiene, hexafluoro-2-propanol, perfluorodecalin, perfluorohexane, tetrabromomethane, 1,1,2,2-tetrchloroethane, tetrachloroethylene, 1,3,5-trichlorobenzene, 1,1,1-trichloroethane, 1,1,2-trichloroethane, trichloroethylene, 1,2,3-trichloropropane, trifluoroacetic acid, and 2,2,2-trifluoroethanol; inorganic based solvents, such as hydrogen chloride, ammonia, carbon disulfide, thionyl chloride, and phophorous tribromide; ketone based solvents, such as, acetone, butanone, ethylisopropyl ketone, isophorone, methyl isobutyl ketone, methyl isopropyl ketone, and 3-pentanone; nitro and nitrile based solvents, such as, nitroethane, acetonitrile, and nitromethane; sulfur based solvents, dimethyl sulfoxide (DMSO), methylsulfonylmethane, sulfolane, isocyanomethane, thiophene, and thiodiglycol; urea, lactone and carbonate based solvents, such as 1-3-dimethyl-3,4,5,6-tetrahydro-2(1H)-pyrimidinone (DMPU), 1-3-dimethyl-2-imidazolidinone, butyrolactone, cis-2,3-butylene carbonate, trans-2,3-butylene carbonate, 2,3-butylene carbonate; carboxylic acid based solvents, such as formic acid, acetic acid, chloracetic acid, trichloroacetic acid, trifluoroacetic acid, propanoic acid, butanoic acid, caproic acid, oxalic acid, and benzoic acid; boron and phosphorous based solvents, such as triethyl borate, triethyl phosphate, trimethyl borate, and trimethyl phosphate; deuterium containing solvents, such as deuterated acetone, deuterated benzene, deuterated chloroform, deuterated dichloromethane, deuterated DMF, deuterated DMSO, deuterated ethanol, deuterated methanol, and deuterated THF; and any appropriate mixtures thereof.

In another embodiment, the nonaqueous solvent used as the solvent system in synthesizing the framework has a pH less than 7. In a further embodiment, the solvent system used to synthesize the framework is an aqueous solution that has a pH less than 7. In yet a further embodiment, the solvent system used to synthesize the frameworks contains water. In another embodiment, the solvent system used to synthesize the frameworks contains water and hydrochloric acid.

Those skilled in the art will be readily able to determine an appropriate solvent or appropriate mixture of solvents based on the starting reactants and/or where the choice of a particular solvent(s) is not believed to be crucial in obtaining the materials of the disclosure.

Templating agents can be used in the methods of the disclosure. Templating agents employed in the disclosure are added to the reaction mixture for the purpose of occupying the pores in the resulting crystalline base frameworks. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

In certain embodiments templating agents are used with the methods disclosed herein, and in other embodiments templating agents are not used with the methods disclosed herein.

Crystallization of the frameworks can be carried out by maintaining the solution, mixture, or suspension at ambient temperature or by maintaining the solution, mixture, or suspension at an elevated temperature; adding a diluted base to the solution; diffusing the diluted base throughout the solution; and/or transferring the solution to a closed vessel and heating to a predetermined temperature.

In a certain embodiment, crystallization of the frameworks can be improved by adding an additive that promotes nucleation.

In a certain embodiment, the solution, mixture or suspension is maintained at ambient temperature to allow for crystallization. In another embodiment, the solution, mixture, or suspension is heated in isothermal oven for up to 300° C. to allow for crystallization. In yet another embodiment, activated frameworks can be generated by calcination. In a further embodiment, calcination of the frameworks can be achieved by heating the frameworks at 350° C. for at least 1 hour.

It is further contemplated that a framework of the disclosure may be generated by first utilizing a plurality of linking moieties having different functional groups, wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups in the organic framework.

After the frameworks are synthesized, the frameworks may be further modified by reacting with one or more post framework reactants that may or may not have denticity. In a certain embodiment, the frameworks as-synthesized are not reacted with a post framework reactant. In another embodiment, the frameworks as-synthesized are reacted with at least one post framework reactant. In yet another embodiment, the frameworks as-synthesized are reacted with at least two post framework reactants. In a further embodiment, the frameworks as-synthesized are reacted with at least one post framework reactant that will result in adding denticity to the framework.

It is contemplated by this disclosure that chemical reactions that modify, substitute, or eliminate a functional group post-synthesis of the framework with post framework reactant may use one or more similar or divergent chemical reaction mechanisms depending on the type of functional group and/or post framework reactant used in the reaction. Examples of chemical reaction mechanisms contemplated by this invention include, but is not limited to, radical-based, unimolecular nuclephilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericylic, electrocylic, rearrangement, carbene, carbenoid, cross coupling, and degradation.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, the post framework reactant is selected to have a property selected from the group comprising, binds a metal ion, increases the hydrophobicity of the framework, modifies the gas sorption of the framework, modifies the pore size of the framework, and tethers a catalyst to the framework.

In one embodiment, the post framework reactant can be a saturated or unsaturated heterocycle.

In another embodiment, the post framework reactant has 1-20 carbons with functional groups including atoms such as N, S, and O.

In yet another embodiment, the post framework reactant is selected to modulate the size of the pores in the framework.

In another embodiment, the post framework reactant is selected to increase the hydrophobicity of the framework.

In yet another embodiment, the post framework reactant is selected to modulate gas separation of the framework. In a certain embodiment, the post framework reactant creates an electric dipole moment on the surface of the framework when it chelates a metal ion.

In a further embodiment, the post framework reactant is selected to modulate the gas sorption properties of the framework. In another embodiment, the post framework reactant is selected to promote or increase hydrocarbon gas sorption of the framework.

In yet a further embodiment, the post framework reactant is selected to increase or add catalytic efficiency to the framework.

In another embodiment, a post framework reactant is selected so that organometallic complexes can be tethered to the framework. Such tethered organometallic complexes can be used, for example, as heterogeneous catalysts.

In one embodiment, the disclosure provides highly catalytically active heterogeneous metal-organic framework (MOF) catalysts $[V(O)(C_{10}H_8O_4)]$ and $[V(O)(C_8H_4O_4)]$ (MOF-V150 and MIL-47, respectively) for the direct, one-step oxidation of methane to acetic acid. These catalysts provide up to 70% yield (490 TON) and are very selective (100%). Both carbon atoms of the acetic acid are directly derived from methane molecules. The catalysts are reusable and easy to separate from the products. They are catalytically active for several recycling steps under mild conditions.

Two vanadium-based MOFs, MOF-V150 and MIL-47, were used as catalysts for methane activation. They were chosen, because their structures are similar to vanadium complexes already known to have activity for this reaction, but as homogeneous catalysts, e.g., Amavandin complexes or V(O)

Figure 2:
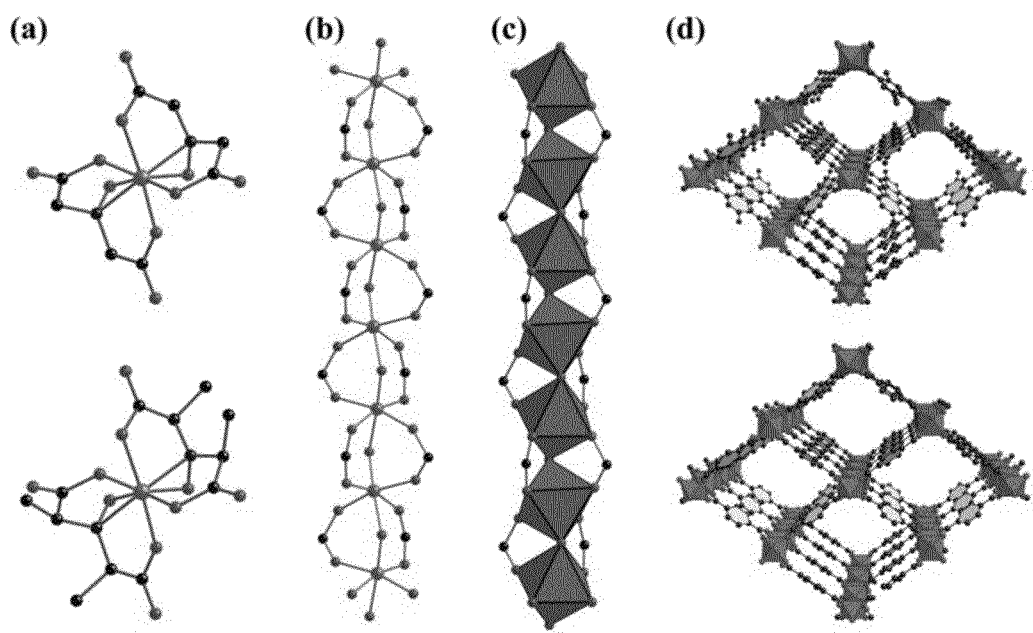
FIG. 2A-D depicts structures of the disclosure. (A) Amavandin complex structures are shown in a ball and stick presentation (V=larger light grey ball, O=light grey, N=dark grey balls connected to V, C=dark grey balls not connected to V). The inorganic SBUs of MOF-V150 and MIL-47 are chains of corner—sharing V octahedra ($VO_6$) that are shown in a ball and stick presentation (B) (V=larger ball light grey, O=light grey balls, N=dark grey balls connected to V, C=dark grey balls not connected to V). (C) The $VO_6$ of SBUs is shown in blue polyhedra. (D) Extended networks of MOF-150 (top) and MIL-47 (bottom). H atoms are omitted for clarity.

(acac)$_2$. (FIG. 2). The MOFs are thermally stable up to 400° C. and chemically stable under strong oxidizing conditions, thus making them promising catalysts for methane activation.

The vanadium MOFs have a secondary building unit (SBU) which is comprised of an infinite (—O—V—)$_\alpha$ rod (FIG. 2b) with carboxylate O atoms completing octahedral coordination around V (FIG. 1). The octahedra (VO$_6$) are linked into rods by corner-sharing. The benzene moieties link these rods into a three-dimensional orthorhombic framework containing a 1-D pore channel. (FIG. 2d) MIL-47 includes a benzendicarboxylic (bdc) as a linker, while MOF-V150 is built from the 2,5-dimethyl-benzendicarboxylic (mbdc) linker. (FIG. 1 and FIG. 2d) MOF-V150 was obtained by reacting mbdc and vanadium (IV) oxide (VO$_2$) in hydrochloric acid and water at 220° C. for 3 days. MIL-47 was obtained by reacting bdc with vanadium (III) chloride (VCI$_3$) in water at 200° C. for 3 days. Activated materials resulted from removing guest molecules in the pores by calcination of the as-synthesized samples at 350° C. in air for 8 hours. Type I nitrogen sorption of the activated MOFs reveals their microporous characteristics. Six different MOF samples were prepared: as-synthesized MOF-V150, partially acti- Reaction 2:

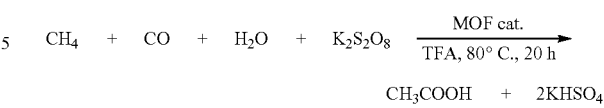

Reaction 3:

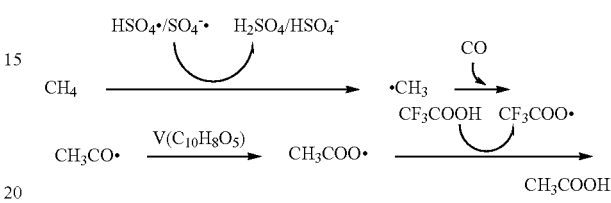

TABLE 1

Catalytic activity of heterogeneous MOF catalysts in the conversion of methane to acetic acid in the absence of CO.

| Catalyst [a] | Surface area (m$^2$g$^{-1}$) | AcOH (mM) | TM (mM) | Yield (%) AcOH [b] | TM [c] | Total [d] | TM select [e] (%) | TON [g] (AcOH) |
|---|---|---|---|---|---|---|---|---|
| MOF-V150-I | — | 0.36 | 0.07 | 36 | 1.8 | 38 | 17 | 89 |
| MOF-V150-II | 100 | 0.38 | 0.30 | 38 | 6.0 | 44 | 29 | 95 |
| MOF-V150-III | 200 | 0.48 | 0.30 | 48 | 7.5 | 56 | 38 | 121 |
| MIL-47-IV | — | 0.38 | 0.08 | 38 | 2.0 | 40 | 18 | 94 |
| MIL-47-V | 350 | 0.60 | 0.08 | 60 | 2.0 | 62 | 11 | 150 |
| MIL-47-VI | 500 | 0.70 | 0.07 | 70 | 1.8 | 72 | 9 | 175 |

[a] Reaction conditions: At ambient temperature, 10 bars of CH$_4$ pressure was introduced to a mixture containing, a MOF catalyst, K$_2$S$_2$O$_8$ (4 mmol), and TFA (7.5 ml). The mixture was then heated at 80° C. for 20 hrs.
[b] AcOH yield was calculated as {(4 × [CH$_3$CO$_2$H])/[K$_2$S$_2$O$_8$]}.
[c] TM yield was calculated as ([CF$_3$CO$_2$CH$_3$]/[K$_2$S$_2$O$_8$]).
[d] Total yield was calculated as {(4 × [CH$_3$CO$_2$H]) + [CF$_3$CO$_2$CH$_3$])/[K$_2$S$_2$O$_8$]} (excluding gaseous products).
[e] TM selectivity was calculated as the molar ratio of AcOH to the total molar yield of products excluding gaseous products.
[g] TON was calculated as the molar ratio of acetic acid to the metal content. A gaseous product is predominately CO$_2$, as determined by GC. With respect to surface area, a dash (—) indicate an as-synthesized sample.

vated MOF-V150 with a surface area of 100 m$^2$/g and 200 m$^2$/g, as-synthesized MIL-47, partially activated MIL-47 with a surface area of 350 m$^2$/g and 500 m$^2$/g. For the direct conversion of methane to acetic acid, each of these MOF samples were used as a catalyst and tested under the same reaction conditions.

It was found, in the absence of CO, that methane was converted to acetic acid in up to 70% yields, corresponding to up to 175 TON, in reactions where MOF-V150 and MIL-47 were the heterogeneous catalysts, KPS was the oxidant and TFA was the solvent. In the presence of CO, these MOFs give up to 49% yield corresponding to up to 490 TON (Reaction 1, 2 and Table 1, 2).

Reaction 1:

2CH$_4$ + H$_2$O + 4K$_2$S$_2$O$_8$ $\xrightarrow[\text{TFA, 80° C., 20 h}]{\text{MOF cat.}}$ CH$_3$COOH + 8H$^+$ + 8KHSO$_4$

TABLE 2

Catalytic activity of heterogeneous MOF catalysts in the conversion of methane to acetic acid in the presence of CO (100% selectivity towards acetic acid).

| Catalysts [a] | Surface area (m$^2$g$^{-1}$) | AcOH (mM) | Total yield(%) [b] | TON [d] (AcOH) |
|---|---|---|---|---|
| MOF-V150-I | — | 1.36 | 34 | 340 |
| MOF-V150-II | 100 | 1.75 | 44 | 440 |
| MOF-V150-III | 200 | 1.95 | 49 | 490 |
| MIL-47-IV | — | 0.95 | 24 | 240 |
| MIL-47-V | 350 | 1.16 | 29 | 290 |
| MIL-47-VI | 500 | 1.32 | 33 | 330 |
| VOSO$_4$ | — | 0.8 | 21 | 210 |

[a] Reaction conditions: At ambient temperature, 10 bars of CH$_4$ pressure (25° C.) and 10 bars of CO pressure were introduced to a mixture containing a MOF catalyst, K$_2$S$_2$O$_8$ (4 mmol), and TFA (7.5 ml). The mixture was then heated at 80° C. for 20 hrs.
[b] Total yield was calculated as ([CH$_3$CO$_2$H]/[K$_2$S$_2$O$_8$]) (excluding gaseous products).
[c] AcOH selectivity was calculated as the molar ratio of AcOH to the total molar yield of products excluding gaseous products.
[d] TON was calculated as the molar ratio of AcOH to the metal content. A gaseous product is predominately CO$_2$, as determined by GC. With respect to surface area, a dash (—) indicate an as-synthesized sample.

In the absence of CO, the major products are acetic acid together with the methyl ester of TFA (trifluoro methyl acetate, TM). Catalysts MIL-47 and MOF-V150 provide 70% and 48% acetic acid yield, respectively. (Table 1). When the catalytic reaction is performed using activated materials, the reaction yields more AcOH (72%) in comparison to the as-synthesized materials (40%). (Table 1, lines 6 and 4). The more open pores of the activated materials lead to a higher product yield, since there are more active centers exposed. Unexpectedly, although the coordination environment of vanadium is the same in both catalysts, MOF-V150 gives higher TM selectivity (38%) than MIL-47 (18%). (Table 1, lines 3 and 4). The presence of two methyl groups in the linker of MOF-V150 creates a more hydrophobic environment within the pores, which might facilitate the formation of the less polar products such as esters. The hydrophobic effect of MOF-V150 is more apparent when the frameworks are activated. The activated sample of MOF-V150 gives significantly higher ester selectivity (38%) compared to the as-synthesized sample (17%). (Table 1, lines 3 and 1). This behavior was not observed in MIL-47.

Reducing the amount of oxidant consumed would elevate the economic feasibility of the finding. Although the MOFs give a high yield of AcOH, the reaction consumes four moles of $K_2S_2O_8$ for one mole of AcOH. (Reaction 1). It was investigated whether the reaction in the presence of CO to attempt to reduce the required amount of oxidant. In the presence of CO the reaction requires only one mole of the oxidant per mole of acetic acid. (Reaction 2). Under otherwise unchanged conditions, the amount of acetic acid found in the reaction mixture increases significantly from 0.7 mmol to 2.0 mmol and TON increases from 199 to 488 at p(CO)=10 bars (table 2), suggesting CO acts as a carbonylation agent as reported. Now, MOF-V150 is more active compared to MIL-47. A reason for the greater activity can only be speculated. Assuming the reaction takes place at the external surface of the MOFs, MOF-V150 would have a larger amount of accessible active sites per weight because of its smaller particle size compared to MIL-47. This effect might contribute to the catalytic activity of MOF-V150. If the reaction takes place inside the pores, the pore size or the pore environment of MOF-V150 might happen to be more suitable for this reaction. MOF-V150 has a smaller pore size (9 Å) than MIL-47 (11 Å) and the additional methyl groups in MOF-V150 may increase the lipophilicity of the material. Notably, the reaction gives 100% selectivity toward acetic acid. (Table 2).

Figure 3:
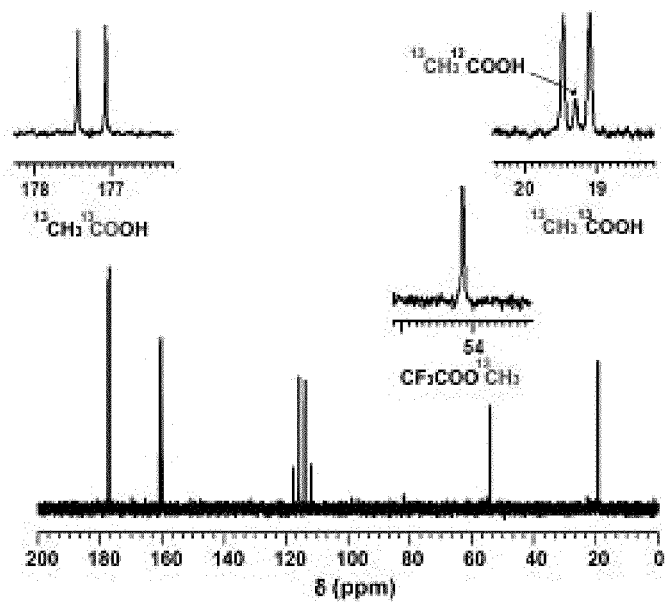
FIG. 3 shows $^{13}C$ NMR of the reaction mixture of $^{13}CH_4$ in the absence of CO.
Figure 4:
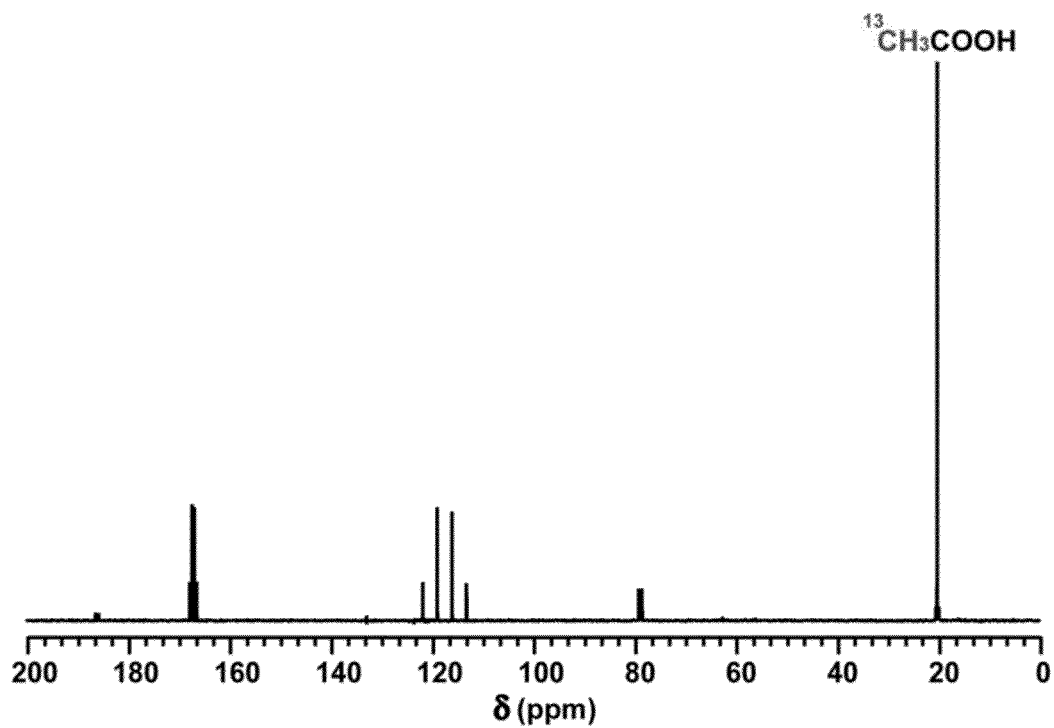
FIG. 4 shows $^{13}C$ NMR of the reaction mixture of $^{13}CH_4$ in the presence of CO.

To confirm the origins of the carbon atoms, the reaction was run with and without CO using >99% *$^{13}$C isotopically enriched methane. Without CO, 90% of the carbon atoms in the acetic acid product were derived from methane molecules. The $^{13}$C NMR spectrum of the crude reaction mixture from the reaction of $^{13}CH_4$ with the MOF catalysts in the absence of CO is shown in FIG. 3. The NMR shows a doublet at δ=19.5 ppm (13CH$_3$—), $^1J(^{13}C, ^{13}C)$=57.2 Hz and at δ=177.5 ppm (—$^{13}$CO), $^1J(^{13}C, ^{13}C)$=57.2 Hz. (FIG. 3). This confirmed that a large amount of acetic acid carbon atoms is derived exclusively from methane molecules. In addition, the spectrum shows a singlet at δ=19.3 ppm. (FIG. 3). This singlet indicates the presence of acetic acid product where 1 carbon is derived from methane and the other originates from TFA. The amount of this acetic acid in the reaction mixture was quantified by $^1H$ NMR to be about 10%. In contrast, with homogeneous vanadium catalysts in the absence of CO, only the methyl group in the acetic acid is derived from methane while the CO is reported to be from TFA. When conducting the reaction in the presence of CO the majority of the acetic acid has the methyl carbon derived from methane and the carbonyl carbon is derived from CO. The $^{13}$C NMR spectrum of the crude reaction mixture from this reaction is shown in FIG. 4. It shows a singlet at δ=20.0 ppm ($^{13}CH_3$—) and a doublet at δ=181 ppm (FIG. 4). The methyl group was found to have near quantitative amounts of $^{13}$C enrichment, while the coupling with the carbonyl group, having natural $^{13}$C abundance (ca. 1%), was not resolved in the spectrum. Vice versa, the $^{13}$C carbons in the carbonyl group always demonstrated coupling with $^{13}$C carbon from the methyl group. Therefore, this group is exclusively observed as a doublet corroborating that the acetic acid predominately formed in the reaction mixture has one carbon from methane and another from CO.

Figure 5:
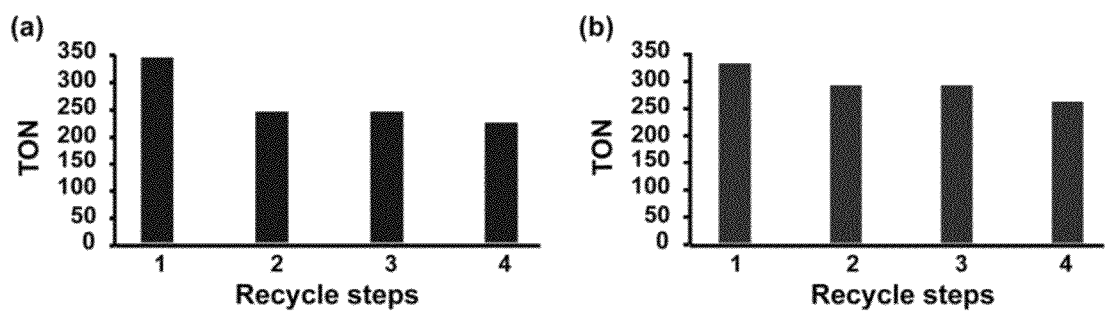
FIG. 5A-B shows catalytic activity of (a) MOF-V150 and (b) MIL-47 in the direct conversion of methane to acetic acid over four recycling steps.
Figure 6:
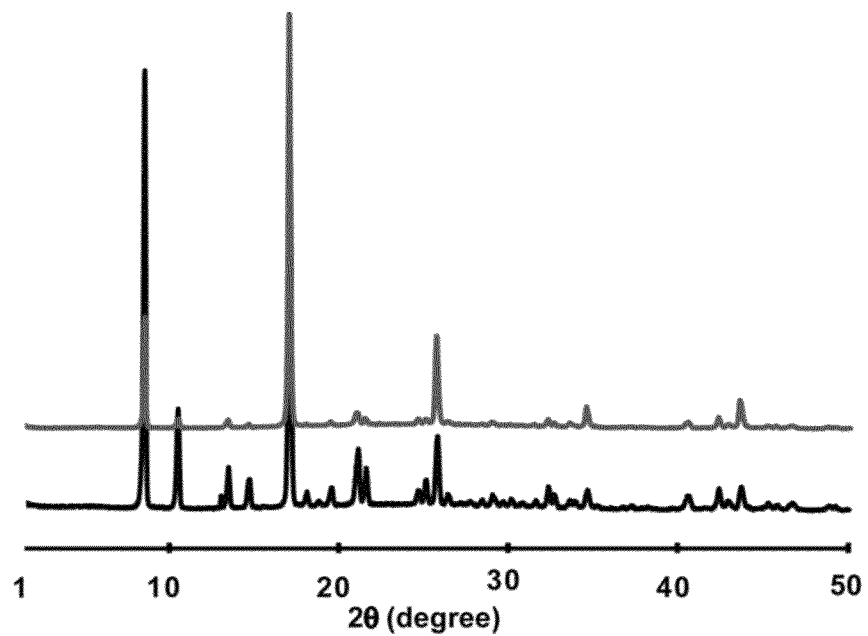
FIG. 6 shows PXRD patterns of MOF-150 before (black) and after (blue) the catalytic reaction.

The catalytic activities of the MOFs remain almost the same during the recycling experiments. There was no reactivation between the steps. The yield and TONs remain nearly constant during the last three recycling steps (FIG. 5). After an aliquot was taken out for $^1H$ NMR analysis, recycling experiments were performed by adding more methane, $K_2S_2O_8$ and TFA to a previous reaction mixture. In addition, it was unexpectedly found that acetic acid was not further oxidized during each additional reaction step. The partial oxidation products from methane are easily over-oxidized to $CO_2$. Therefore, stopping the oxidation at acetic acid requires a highly selective catalyst. (ref) Consequently, the MOF catalysts of the disclosure are highly selective catalysts. In addition, the MOFs maintain unexpectedly high structural integrity during the recycling, as evidenced by comparing the pxrd patterns between the fresh catalyst and the recycled catalyst (FIG. 6).

Filtration experiments confirmed the true heterogeneous nature of the catalytic reaction. After the initial experiment, the MOF catalyst was removed by filtration. Then, fresh $K_2S_2O_8$ and TFA were added to the filtrate. The reaction was then performed with the filtrate under the same reaction conditions as the initial experiment. No catalytic conversion was observed. This indicates that if there is any leaching of vanadium ions from the catalysts, the vanadium species resulting there from are not catalytically active.

When the experiments are run without a MOF-catalyst or without oxidants no acetic acid results, indicating that both the oxidant and the MOF-catalyst are required for a productive reaction. A control experiment has been carried out with the homogeneous catalyst $VOSO_4$, which gives 13% and 21% acetic acid yield in the absence and presence of CO, respectively. Therefore, the MOF catalysts of the disclosure are unexpectedly far more efficient at catalyzing alkane oxidations than similar catalysts known in the art (see Table 2).

Although the mechanism is still unknown, it is proposed that the oxidative activation of methane, with $K_2S_2O_8$ as the oxidizing agent, TFA as the solvent, and in the presence of vanadium catalysts, results from the formation of methyl radicals. These methyl radicals would in turn react with CO to form $CH_3CO$. radicals. $K_2S_2O_8$ in the acidic TFA solvent can exist in the protonated form $HS_2O_8^-$ or the un-protonated form $S_2O_8^{2-}$. Upon thermal decomposition, hydrosulfate or sulfate radicals ($HSO_4^-$., $SO_4^-$.) are formed. (Reaction 3). The formation of TM ester was reported to be the product of a $CH_3$. or $HSO_4$. radical reacting with $CF_3COOH$ to form a $CF_3COO$. radical. This $CF_3COO$. radical then reacts with $CH_3$. to form the TM ester.

The disclosure provides highly active heterogeneous MOF catalysts that can directly and selectively activate methane to yield acetic acid in a one-step reaction under mild conditions. The catalysts are stable under the applied catalytic conditions and are reusable for at least four recycling steps. Oxidation of other substrates such as ethane and propane are possible. Due to its regular pore structure, the activity of the MOF catalyst is not reduced by fixation. It may even introduce an additional positive aspect as suggested by the higher TON of the MOF catalyst over the homogeneous ones. The pore sizes and shapes of MOFs can act as a reaction vessel with tunable size and polarity. This can enhance selectivity and increase affinity for a particular substrate. This tunability can be employed to target a specific product as shown by comparison of MOF-V150 and MIL-47. Furthermore, MOFs provide a high density of accessible active sites. However, it should be kept in mind that crystal defects might create open vanadium metal sites which could be responsible for the catalytic activity.

Results for ethane oxidative reaction:

TABLE 3

Product yields for MOF-V150, MIL-47, and VOSO$_4$ in the absence of CO

| [a]Catalysts/ Yield (%) | Propanoic acid (P.A)[b] | Acetic acid (AcOH)[c] | Trifluoroethyl acetate (TM)[d] | Total yield[e] |
| --- | --- | --- | --- | --- |
| MOF-V150 | 4 | 43 | 14 | 61 |
| MIL-47 | 3 | 41 | 25 | 69 |
| VOSO$_4$ | 1 | 36 | 0 | 37 |

[a]Reaction conditions: At ambient temperature, 10 bars of C$_2$H$_6$ pressure was introduced to a mixture containing, a MOF catalyst, K$_2$S$_2$O$_8$ (4 mmol), and TFA (7.5 ml). The mixture was then heated at 80° C. for 20 hrs.
[b]P.A yield was calculate as [C$_2$H$_5$CO$_2$H]/[K$_2$S$_2$O$_8$].
[c]AcOH yield was calculate as [CH$_3$CO$_2$H]/[K$_2$S$_2$O$_8$].
[d]TM yield was calculated as ([CF$_3$CO$_2$CH$_3$]/[K$_2$S$_2$O$_8$]).
[e]Total yield was calculated as {[C$_2$H$_5$CO$_2$H] + [CH$_3$CO$_2$H]) + [CF$_3$CO$_2$CH$_3$]/[K$_2$S$_2$O$_8$]} (excluding gaseous product).

Results for ethane oxidative carbonylation reaction:

TABLE 4

Product yields for MOF-V150, MIL-47, and VOSO$_4$ in the presence of CO

| Catalysts/Yield (%)[a] | Propanoic acid (P.A)[b] | Acetic acid (AcOH)[c] | Trifluoroethyl acetate (TM)[d] | Total yield[e] |
| --- | --- | --- | --- | --- |
| MOF-V150 | 32 | 25 | 22 | 80 |
| MIL-47 | 63 | 14 | 3 | 78 |
| VOSO$_4$ | 62 | 10 | 0.5 | 72 |

[a]Reaction conditions: At ambient temperature, 10 bars of C$_2$H$_6$ pressure (25° C.) and 10 bars of CO pressure were introduced to a mixture containing, a MOF catalyst, K$_2$S$_2$O$_8$ (4 mmol), and TFA (7.5 ml). The mixture was then heated at 80° C. for 20 hrs.
[b]P.A yield was calculate as [C$_2$H$_5$CO$_2$H]/[K$_2$S$_2$O$_8$].
[c]AcOH yield was calculate as [CH$_3$CO$_2$H]/[K$_2$S$_2$O$_8$].
[d]TM yield was calculated as ([CF$_3$CO$_2$CH$_3$]/[K$_2$S$_2$O$_8$]).
[e]Total yield was calculated as {[C$_2$H$_5$CO$_2$H] + [CH$_3$CO$_2$H]) + [CF$_3$CO$_2$CH$_3$]/[K$_2$S$_2$O$_8$]} (excluding gaseous product).

TABLE 5

Total ester selectivity for MOFs in the presence of CO

| Catalysts | Ave ester selectivity (%) * |
| --- | --- |
| MOF-V150 | 69 |
| MIL-47 | 60 |

* TM selectivity was calculated as molar ratio of AcOH to total molar of products excluding gaseous product.

TABLE 6

Effect of pores on product distribution in the presence of CO

| MIL-47 | Less open pores | More open pores |
| --- | --- | --- |
| Ethyl acetate yield (ave %) | 0 | 17 |
| Trifluoroethyl acetate yield (ave %) | 28 | 35 |
| Ester selectivity (ave %) | 60 | 81 |
| Total yield (ave %) | 66 | 79 |

This disclosure describes the synthesis and use of vanadium containing frameworks for oxidizing and functionalizing alkanes. Although, MOFs with vanadium as part of the SBU are useful, post-synthesis metallated materials can also be used.

A number of embodiments of the invention have been described. Nevertheless, it will be understood that various modifications may be made without departing from the spirit and scope of the invention. Accordingly, other embodiments are within the scope of the following claims.

What is claimed is:

1. A method to convert an alkane to an alcohol or carboxylic acid by contacting the alkane with a catalytically active heterogeneous vanadium containing metal organic framework (MOF) in the presence of an oxidant, wherein the vanadium containing MOF comprises a plurality of repeating cores comprising vanadium or vanadium ion(s) that are linked together by organic linking moieties.

2. The method of claim 1, wherein the alkane is a linear (C$_1$-C$_{12}$)alkane.

3. The method of claim 1, wherein the method is carried out in the presence of CO.

4. The method of claim 1, wherein the oxidant is K$_2$S$_2$O$_8$.

5. The method of claim 1, wherein the alkane is converted to a carboxylic acid.

6. The method of claim 1, wherein the vanadium ion(s) is selected from the group consisting of V$^{5+}$, V$^{4+}$, V$^{3+}$, and V$^{2+}$.

7. The method of claim 1, wherein the metal organic framework comprises vanadium or vanadium ions with octahedral coordination spheres.

8. The method of claim 1, wherein the metal organic framework has a linking moiety with a parent chain selected from the group consisting of hydrocarbon, hetero-alkane, hetero-alkene, hetero-alkyne, and heterocycle; and wherein the parent chain is functionalized with at least one linking cluster.

9. The method of claim 1, wherein the metal organic framework is generated from a plurality of linking moieties comprising one or more of structural Formulae I, II, III, IV, V, VI, VII, VIII, IX and X:

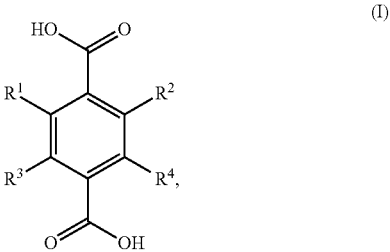

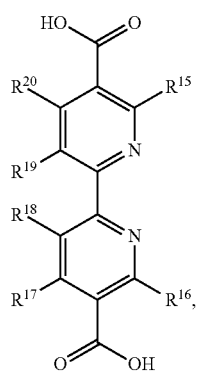 (II)
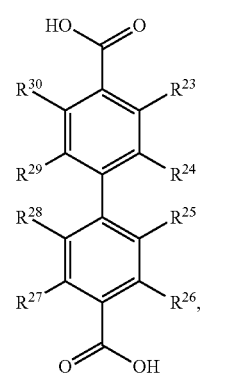 (III)
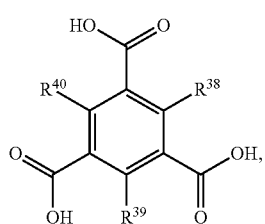 (IV)
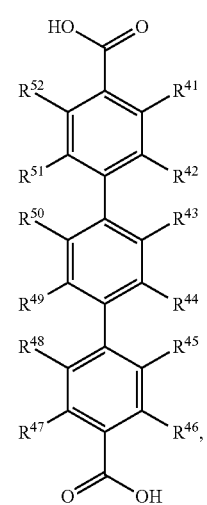 (V)
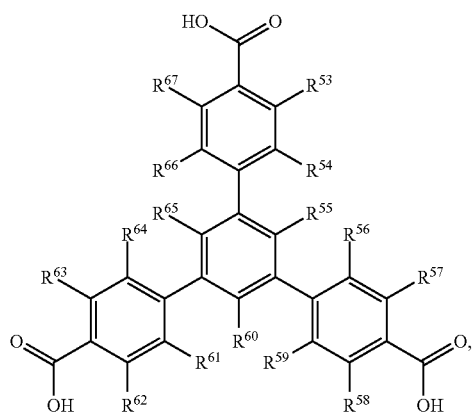 (VI)
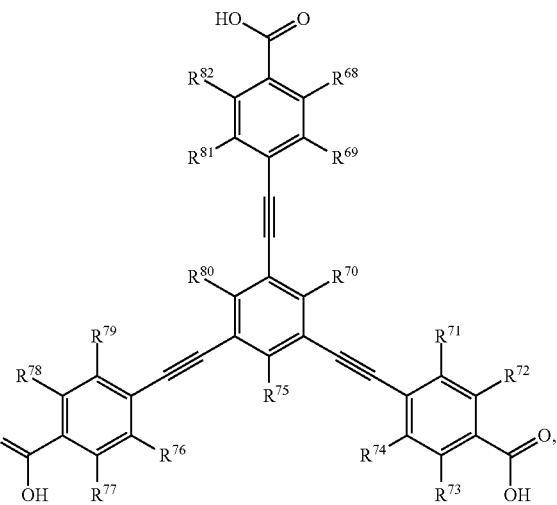 (VII)
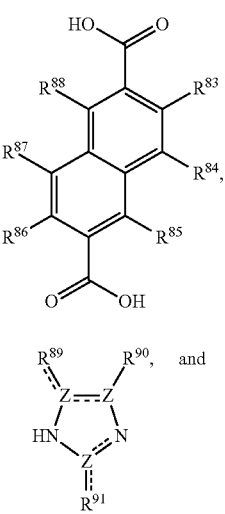 (VIII)
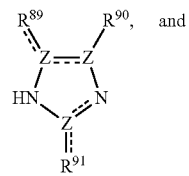 (IX)
and -continued

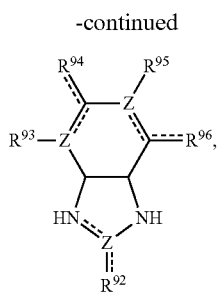

(X)

wherein:
R$^1$-R$^4$, R$^{16}$-R$^{20}$, R$^{23}$-R$^{30}$, R$^{38}$-R$^{96}$ are independently selected from the group consisting of H, functional group (FG), (C$_1$-C$_{20}$)alkyl, substituted (C$_1$-C$_{20}$)alkenyl, substituted (C$_1$-C$_{20}$)alkenyl, (C$_1$-C$_{20}$)alkynyl, substituted (C$_1$-C$_{20}$)alkynyl, hetero-(C$_1$-C$_{20}$)alkyl, substituted hetero-(C$_1$-C$_{20}$)alkyl, hetero-(C$_1$-C$_{20}$)alkenyl, substituted hetero-(C$_1$-C$_{20}$)alkenyl, hetero-(C$_1$-C$_{20}$)alkynyl, substituted hetero-(C$_1$-C$_{20}$)alkynyl, (C$_1$-C$_{20}$)cycloalkyl, substituted (C$_1$-C$_{20}$)cycloalkyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$, and

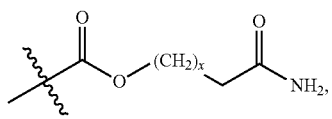

wherein R$^1$ and R$^3$ may be linked together to form a substituted or unsubstituted ring selected from the group consisting of cycloalkyl, aryl and heterocycle, wherein R$^2$ and R$^4$ may be linked together to form a substituted or unsubstituted ring selected from the group consisting of cycloalkyl, aryl and heterocycle, wherein R$^{18}$ and R$^{19}$ may be linked together to form a substituted or unsubstituted ring selected from the group consisting of cycloalkyl, aryl and heterocycle, wherein R$^{24}$ and R$^{25}$ may be linked together to form a substituted or unsubstituted ring selected from the group consisting of cycloalkyl, aryl and heterocycle, and/or wherein R$^{28}$ and R$^{29}$ may be linked together to form a substituted or unsubstituted ring selected from the group consisting of cycloalkyl, aryl and heterocycle;

R$^5$ is selected from the group consisting of FG, (C$_1$-C$_{20}$) alkyl, (C$_1$-C$_{20}$)substituted alkyl, (C$_1$-C$_{20}$)alkenyl, substituted (C$_1$-C$_{20}$)alkenyl, (C$_1$-C$_{20}$)alkynyl, substituted (C$_1$-C$_{20}$)alkynyl, hetero-(C$_1$-C$_{20}$)alkyl, substituted hetero-(C$_1$-C$_{20}$)alkyl, hetero-(C$_1$-C$_{20}$)alkenyl, substituted hetero-(C$_1$-C$_{20}$)alkenyl, hetero-(C$_1$-C$_{20}$) alkynyl, substituted hetero-(C$_1$-C$_{20}$)alkynyl, hemiacetal, hemiketal, acetal, ketal, and orthoester;

R$_6$ is one or more substituted or unsubstituted rings selected from the group consisting of cycloalkyl, aryl, and heterocycle;

Z is either a C or N; and

X is a number from 0 to 10.

10. The method of claim 1, wherein the metal organic framework is generated from a plurality of linking moieties comprising structural Formula I, II, III, IV, V, VI, VII, VIII, IX or X:

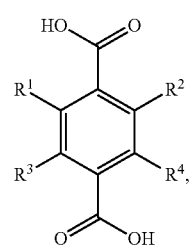

(I)

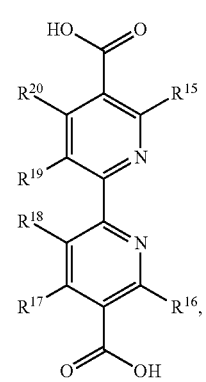

(II)

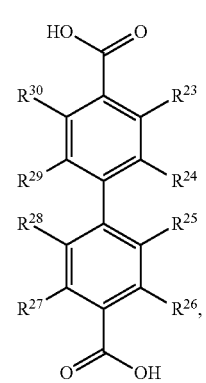

(III)

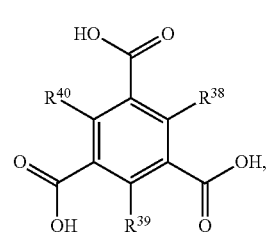

(IV)

(V)

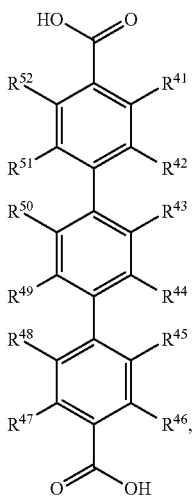

(VI)

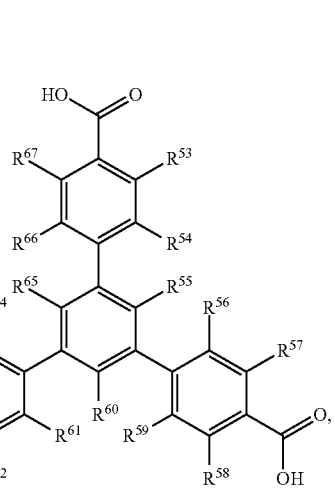

(VII)

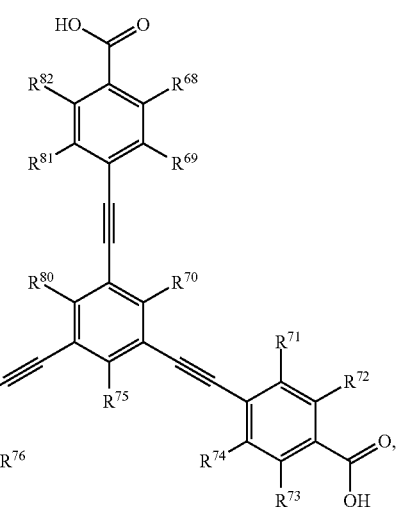

(VIII)

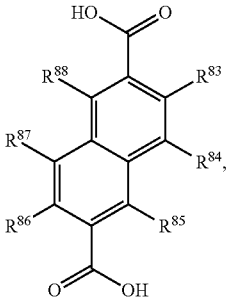

(IX)

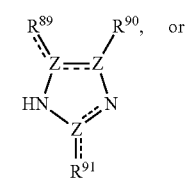

(X)

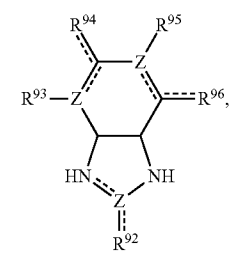

wherein:
$R^1$-$R^4$, $R^{15}$-$R^{20}$, $R^{23}$-$R^{30}$, $R^{38}$-$R^{96}$ are independently selected from the group consisting of H, functional group (FG), $(C_1$-$C_{20})$alkyl, substituted $(C_1$-$C_{20})$alkyl, $(C_1$-$C_{20})$alkenyl, substituted $(C_1$-$C_{20})$alkenyl, $(C_1$-$C_{20})$alkynyl, substituted $(C_1$-$C_{20})$alkynyl, hetero-$(C_1$-$C_{20})$alkyl, substituted hetero-$(C_1$-$C_{20})$alkyl, hetero-$(C_1$-$C_{20})$alkenyl, substituted hetero-$(C_1$-$C_{20})$alkenyl, hetero-$(C_1$-$C_{20})$alkynyl, substituted hetero-$(C_1$-$C_{20})$alkynyl, $(C_1$-$C_{20})$cycloalkyl, substituted $(C_1$-$C_{20})$cycloalkyl, aryl, substituted aryl, heterocycle, substituted heterocycle, —C$(R^5)_3$, —CH$(R^5)_2$, —CH$_2R^5$, —C$(R^6)_3$, —CH$(R^6)_2$, —CH$_2R^6$, —OC$(R^5)_3$, —OCH$(R^5)_2$, —OCH$_2R^5$, —OC$(R^6)_3$, —OCH$(R^6)_2$, —OCH$_2R^6$, and

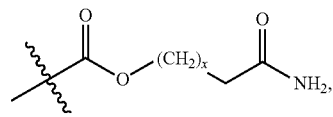

wherein $R^1$ and $R^3$ may be linked together to form a substituted or unsubstituted ring selected from the group consisting of cycloalkyl, aryl and heterocycle, wherein $R^2$ and $R^4$ may be linked together to form a substituted or unsubstituted ring selected from the group consisting of cycloalkyl, aryl and heterocycle, wherein $R^{18}$ and $R^{19}$ may be linked together to form a substituted or unsubstituted ring selected from the group consisting of cycloalkyl, aryl and heterocycle, wherein $R^{24}$ and $R^{25}$ may be linked together to form a substituted or unsubstituted ring selected from the group consisting of cycloalkyl, aryl and heterocycle, and/or wherein $R^{28}$ and $R^{29}$ may be linked together to form a substituted or unsubstituted ring selected from the group consisting of cycloalkyl, aryl and heterocycle;

$R^5$ is selected from the group consisting of FG, $(C_1-C_{20})$ alkyl, $(C_1-C_{20})$substituted alkyl, $(C_1-C_{20})$alkenyl, substituted $(C_1-C_{20})$alkenyl, $(C_1-C_{20})$alkynyl, substituted $(C_1-C_{20})$alkynyl, hetero-$(C_1-C_{20})$alkyl, substituted hetero-$(C_1-C_{20})$alkyl, hetero-$(C_1-C_{20})$alkenyl, substituted hetero-$(C_1-C_{20})$alkenyl, hetero-$(C_1-C_{20})$alkynyl, substituted hetero-$(C_1-C_{20})$alkynyl, hemiacetal, hemiketal, acetal, ketal, and orthoester;

$R^6$ is one or more substituted or unsubstituted rings selected from the group consisting of cycloalkyl, aryl, and heterocycle;

Z is either a C or N; and

X is a number from 0 to 10.

11. The method of claim 1, wherein the metal organic framework is generated from a plurality of linking moieties comprising one or more of structural Formulae I, II, III, IV, V, VI, VII, and VIII:

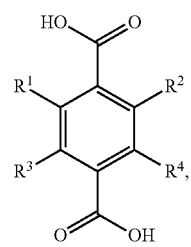
(I)

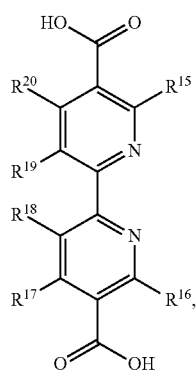
(II)

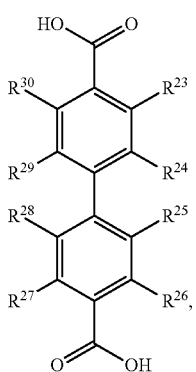
(III)

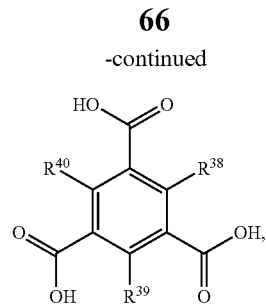
(IV)

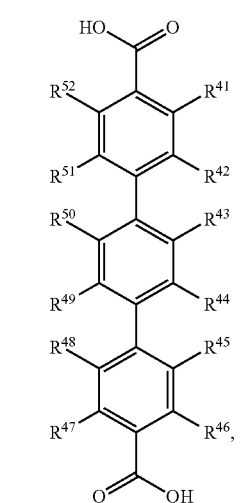
(V)

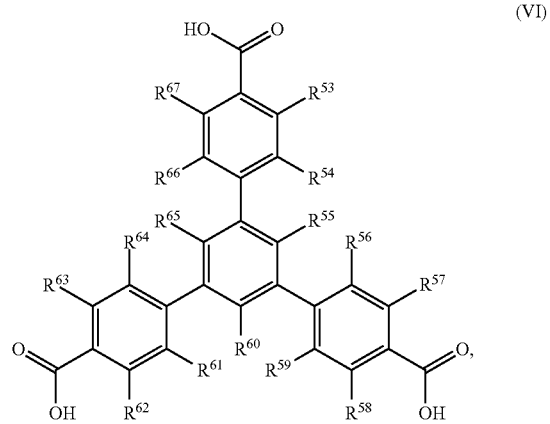
(VI)

(VII)

and

-continued

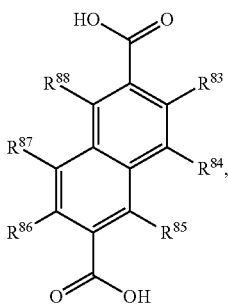

(VIII)

wherein:
R$^1$-R$^4$, R$^{15}$-R$^{20}$, R$^{23}$-R$^{30}$, R$^{38}$-R$^{88}$ are independently selected from the group consisting of H, functional group (FG), (C$_1$-C$_6$)alkyl, substituted (C$_1$-C$_6$)alkyl, (C$_1$-C$_6$)alkenyl, substituted (C$_1$-C$_6$)alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, (C$_1$-C$_6$)cycloalkyl, substituted (C$_1$-C$_6$)cycloalkyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$, and

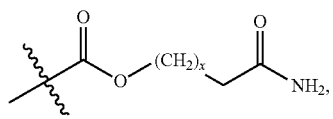

wherein R$^1$ and R$^3$ may be linked together to form a substituted or unsubstituted ring selected from the group consisting of cycloalkyl, aryl and heterocycle, wherein R$^2$ and R$^4$ may be linked together to form a substituted or unsubstituted ring selected from the group consisting of cycloalkyl, aryl and heterocycle, wherein R$^{18}$ and R$^{16}$ may be linked together to form a substituted or unsubstituted ring selected from the group consisting of cycloalkyl, aryl and heterocycle, wherein R$^{24}$ and R$^{25}$ may be linked together to form a substituted or unsubstituted ring selected from the group consisting of cycloalkyl, aryl and heterocycle, and/or wherein R$^{28}$ and R$^{29}$ may be linked together to form a substituted or unsubstituted ring selected from the group consisting of cycloalkyl, aryl and heterocycle;

R$^5$ is selected from the group consisting of FG, (C$_1$-C$_6$) alkyl, (C$_1$-C$_6$)substituted alkyl, (C$_1$-C$_6$)alkenyl, substituted (C$_1$-C$_6$)alkenyl, (C$_1$-C$_6$)alkynyl, substituted (C$_1$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_1$-C$_6$)alkenyl, hetero-(C$_1$-C$_6$)alkynyl, substituted hetero-(C$_1$-C$_6$)alkynyl, hemiacetal, hemiketal, acetal, ketal, and orthoester;

R$_6$ is one or more substituted or unsubstituted rings selected from the group consisting of cycloalkyl, aryl, and heterocycle; and X is a number from 0 to 3.

12. The method of claim 1, wherein the metal organic framework is generated from a plurality of linking moieties comprising one or more of structural Formulae I, II, III, IV, V, VI, VII, and VIII:

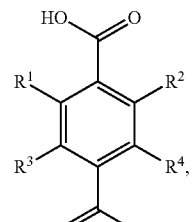

(I)

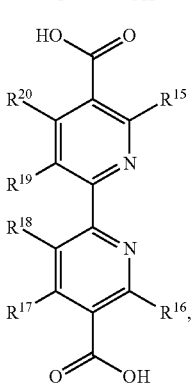

(II)

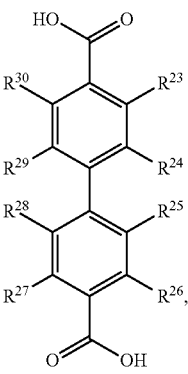

(III)

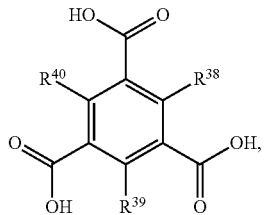

(IV)

-continued

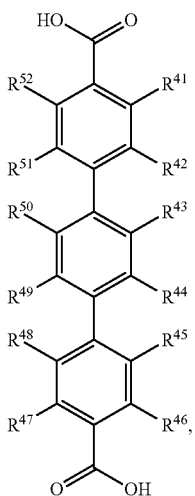

(V)

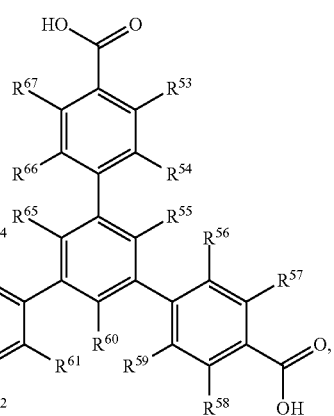

(VI)

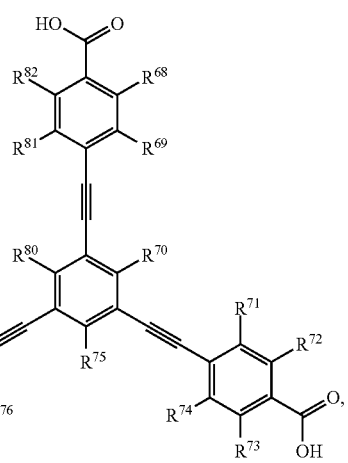

(VII)

-continued

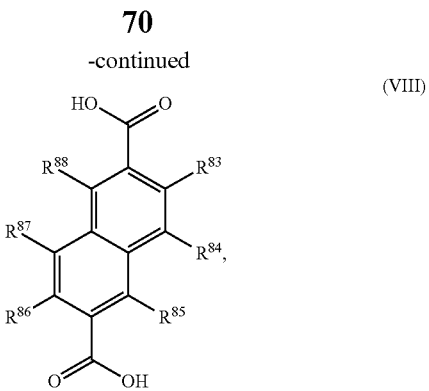

(VIII)

wherein:

$R^1$-$R^4$, $R^{15}$-$R^{20}$, $R^{23}$-$R^{30}$, $R^{38}$-$R^{88}$ are independently selected from the group consisting of H, functional group (FG), $(C_1$-$C_6)$alkyl, substituted $(C_1$-$C_6)$alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_1$-$C_6)$alkenyl, hetero-$(C_1$-$C_6)$alkynyl, substituted hetero-$(C_1$-$C_6)$alkynyl, $(C_1$-$C_6)$cycloalkyl, substituted $(C_1$-$C_6)$cycloalkyl, aryl, substituted aryl, heterocycle, substituted heterocycle, —$C(R^5)_3$, —$CH(R^5)_2$, —$CH_2R^5$, —$C(R^6)_3$, —$CH(R^6)_2$, —$CH_2R^6$, —$OC(R^5)_3$, —$OCH(R^5)_2$, —$OCH_2R^5$, —$OC(R^6)_3$, —$OCH(R^6)_2$, —$OCH_2R^6$, and

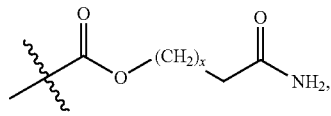

wherein $R^1$ and $R^3$ may be linked together to form a substituted or unsubstituted ring selected from the group consisting of cycloalkyl, aryl and heterocycle, wherein $R^2$ and $R^4$ may be linked together to form a substituted or unsubstituted ring selected from the group consisting of cycloalkyl, aryl and heterocycle, wherein $R^{18}$ and $R^{19}$ may be linked together to form a substituted or unsubstituted ring selected from the group consisting of cycloalkyl, aryl and heterocycle, wherein $R^{24}$ and $R^{25}$ may be linked together to form a substituted or unsubstituted ring selected from the group consisting of cycloalkyl, aryl and heterocycle, and/or wherein $R^{28}$ and $R^{29}$ may be linked together to form a substituted or unsubstituted ring selected from the group consisting of cycloalkyl, aryl and heterocycle;

$R^5$ is selected from the group consisting of FG, $(C_1$-$C_6)$alkyl, $(C_1$-$C_6)$substituted alkyl, $(C_1$-$C_6)$alkenyl, substituted $(C_1$-$C_6)$alkenyl, $(C_1$-$C_6)$alkynyl, substituted $(C_1$-$C_6)$alkynyl, hetero-$(C_1$-$C_6)$alkyl, substituted hetero-$(C_1$-$C_6)$alkyl, hetero-$(C_1$-$C_6)$alkenyl, substituted hetero-$(C_1$-$C_6)$alkenyl, hetero-$(C_1$-$C_6)$alkynyl, substituted hetero-$(C_1$-$C_6)$alkynyl, hemiacetal, hemiketal, acetal, ketal, and orthoester;

$R_6$ is one or more substituted or unsubstituted rings selected from the group consisting of cycloalkyl, aryl, and heterocycle; and X is a number from 0 to 3.

13. The method of claim 1, wherein the metal organic framework is generated from a linking moiety comprising structural Formula I:

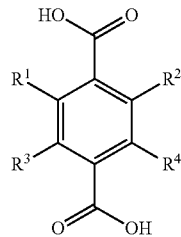

wherein:
R$^1$-R$^4$ are independently selected from the group consisting of H, halo, amine, cyano, Si(OH)$_3$, Ge(OH)$_3$, Sn(OH)$_3$, Si(SH)$_4$, Ge(SH)$_4$, AsO$_3$H, AsO$_4$H, P(SH)$_3$, As(SH)$_3$, CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, POSH, AsO$_3$H, AsO$_4$H, P(SH)$_3$, As(SH)$_3$, (C$_1$-C$_6$)alkyl, substituted (C$_1$-C$_6$)alkyl, (C$_1$-C$_6$)alkenyl, substituted (C$_2$-C$_6$)alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$)alkenyl, hetero-(C$_2$-C$_6$)alkynyl, substituted hetero-(C$_2$-C$_6$)alkynyl, aryl, substituted aryl, heterocycle, substituted heterocycle, —C(R$^5$)$_3$, —CH(R$^5$)$_2$, —CH$_2$R$^5$, —C(R$^6$)$_3$, —CH(R$^6$)$_2$, —CH$_2$R$^6$, —OC(R$^5$)$_3$, —OCH(R$^5$)$_2$, —OCH$_2$R$^5$, —OC(R$^6$)$_3$, —OCH(R$^6$)$_2$, —OCH$_2$R$^6$,

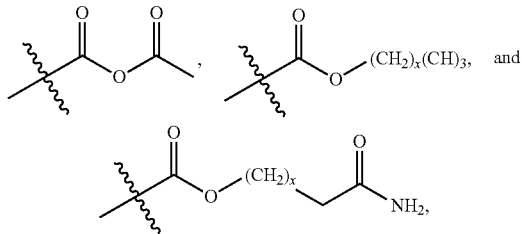

wherein R$^1$ and R$^3$ may be linked together to form a substituted or unsubstituted ring selected from the group consisting of cycloalkyl, aryl and heterocycle, and/or wherein R$^2$ and R$^4$ may be linked together to form a substituted or unsubstituted ring selected from the group consisting of cycloalkyl, aryl and heterocycle;
R$^5$ is selected from the group comprising hydroxyl, amine, thiol, cyano, carboxyl, (C$_1$-C$_6$)alkyl, (C$_1$-C$_6$) substituted alkyl, (C$_1$-C$_6$)alkenyl, substituted (C$_2$-C$_6$) alkenyl, (C$_2$-C$_6$)alkynyl, substituted (C$_2$-C$_6$)alkynyl, hetero-(C$_1$-C$_6$)alkyl, substituted hetero-(C$_1$-C$_6$)alkyl, hetero-(C$_1$-C$_6$)alkenyl, substituted hetero-(C$_2$-C$_6$) alkenyl, hetero-(C$_2$-C$_6$)alkynyl, substituted hetero-(C$_2$-C$_6$)alkynyl, hemiacetal, hemiketal, acetal, ketal, and orthoester;
R$^6$ is one or more substituted or unsubstituted rings selected from the group consisting of cycloalkyl, aryl, and heterocycle; and
X is a number from 0 to 3.

14. The method of claim 13, wherein the linking moiety is selected from the group consisting of

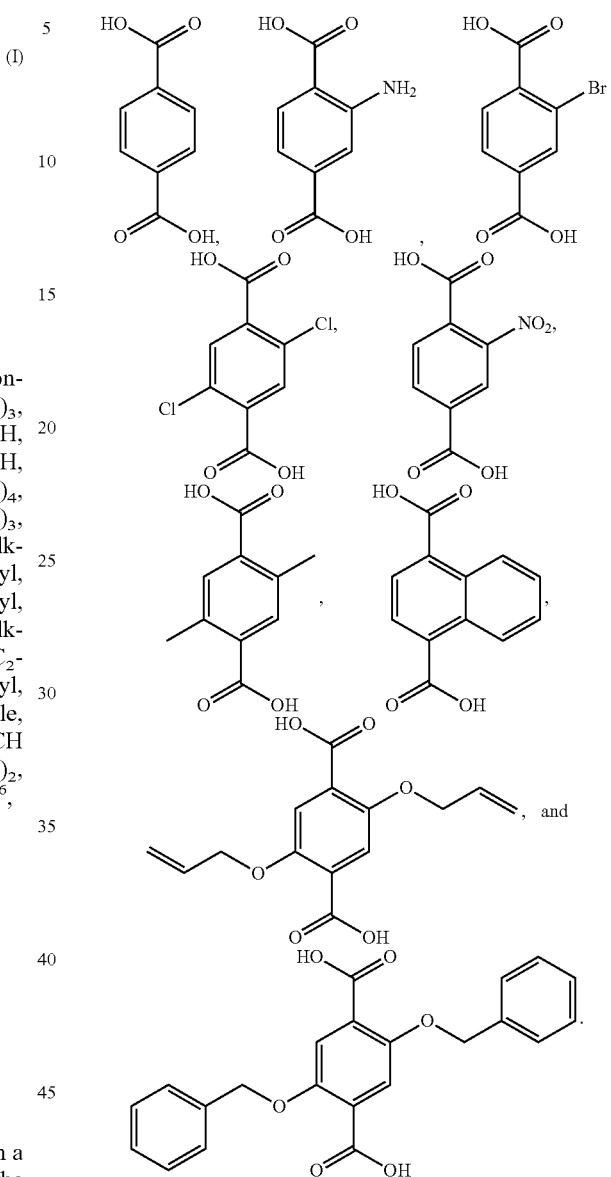

15. The method of claim 1, wherein at least one of the functional groups of the metal organic framework is further modified, substituted, or eliminated with a different functional group post-synthesis of the framework.

16. The method of claim 15, wherein the metal organic framework is further modified by adding a functional group post synthesis of the framework that has one or more properties selected from the group consisting of: binds a metal ion, increases the hydrophobicity of the framework, modifies the gas sorption of the framework, modifies the pore size of the framework, and tethers a catalyst to the framework.

17. The method of claim 1, wherein the metal organic framework comprises [V(O)(C$_{10}$H$_8$O$_4$)] or [V(O)(C$_8$H$_4$O$_4$)].

18. The method of claim 1, wherein the alkane is either methane or ethane.

19. The method of claim 1, wherein the method converts methane to acetic acid with up to a 70% yield.

20. The method of claim 1, wherein the method can be performed multiple times with the same MOF.

* * * * *